(12) United States Patent
Ignon et al.

(10) Patent No.: US 11,202,657 B2
(45) Date of Patent: *Dec. 21, 2021

(54) DEVICES, SYSTEMS AND METHODS FOR TREATING THE SKIN

(71) Applicant: EDGE SYSTEMS LLC, Long Beach, CA (US)

(72) Inventors: Roger Ignon, Redondo Beach, CA (US); Ed F. Nicolas, Wilmington, CA (US); Scott R. Mallett, Coto De Caza, CA (US)

(73) Assignee: EDGE SYSTEMS LLC, Long Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/163,237

(22) Filed: Jan. 29, 2021

(65) Prior Publication Data

US 2021/0145480 A1 May 20, 2021

Related U.S. Application Data

(63) Continuation of application No. 16/241,572, filed on Jan. 7, 2019, now Pat. No. 10,993,743, which is a
(Continued)

(51) Int. Cl.
*A61B 17/54* (2006.01)
*A61B 50/22* (2016.01)
(Continued)

(52) U.S. Cl.
CPC ............ *A61B 17/545* (2013.01); *A61B 17/54* (2013.01); *A61B 17/58* (2013.01); *A61B 50/20* (2016.02);
(Continued)

(58) Field of Classification Search
CPC ....... A61B 17/545; A61B 50/20; A61B 50/22; A61B 17/54; A61B 17/58; A61B 17/205;
(Continued)

(56) References Cited

U.S. PATENT DOCUMENTS 1,651,585 A 12/1927 Clair
2,608,032 A 8/1952 Garver
(Continued)

FOREIGN PATENT DOCUMENTS

AT 400 305 12/1995
AU 1 014 299 5/1999
(Continued)

OTHER PUBLICATIONS

File History of Reissue U.S. Appl. No. 11/027,590, filed Dec. 29, 2004 (Reissue of U.S. Pat. No. 6,500,183, issued Dec. 31, 2002).
(Continued)

*Primary Examiner* — Aaron F Roane
(74) *Attorney, Agent, or Firm* — Knobbe, Martens, Olson & Bear, LLP

(57) ABSTRACT

According to some embodiments, a method of treating a skin surface of a subject comprises heating a skin surface, abrading native skin tissue of a subject using a microdermabrasion device, wherein using the microdermabrasion device comprises moving the microdermabrasion device relative to the skin surface while simultaneously delivering at least one treatment fluid to the skin surface being treated and cooling the abraded skin surface.

21 Claims, 36 Drawing Sheets

Related U.S. Application Data continuation of application No. 14/774,641, filed as application No. PCT/US2014/024992 on Mar. 12, 2014, now Pat. No. 10,172,644.

(60) Provisional application No. 61/788,420, filed on Mar. 15, 2013, provisional application No. 61/791,157, filed on Mar. 15, 2013.

(51) Int. Cl.

| | | |
|---|---|---|
| *A61B 50/20* | (2016.01) | |
| *A61F 7/00* | (2006.01) | |
| *A61B 17/58* | (2006.01) | |
| *A61M 35/00* | (2006.01) | |
| A61B 18/00 | (2006.01) | |
| A61B 17/20 | (2006.01) | |
| A61B 18/14 | (2006.01) | |
| A61B 17/00 | (2006.01) | |
| A61B 18/18 | (2006.01) | |
| A61N 7/00 | (2006.01) | |

(52) U.S. Cl.
CPC .............. *A61B 50/22* (2016.02); *A61F 7/007* (2013.01); *A61M 35/003* (2013.01); *A61B 17/205* (2013.01); *A61B 18/14* (2013.01); *A61B 18/18* (2013.01); *A61B 2017/00747* (2013.01); *A61B 2017/00761* (2013.01); *A61B 2018/0047* (2013.01); *A61B 2018/00291* (2013.01); *A61B 2217/005* (2013.01); *A61B 2217/007* (2013.01); *A61F 2007/0075* (2013.01); *A61N 2007/0034* (2013.01)

(58) Field of Classification Search
CPC .................... A61B 18/14; A61B 18/18; A61B 2017/00747; A61B 2017/00761; A61B 2018/00291; A61B 2018/0047; A61B 2217/005; A61B 2217/007; A61B 2007/0075; A61F 7/007; A61F 2007/0075; A61M 35/003; A61N 2007/0034

See application file for complete search history.

(56) References Cited

U.S. PATENT DOCUMENTS

| | | | |
|---|---|---|---|
| 2,631,583 A | 3/1953 | Lavergne | |
| 2,701,559 A | 2/1955 | Cooper | |
| 2,712,823 A | 7/1955 | Kurtin | |
| 2,867,214 A | 1/1959 | Wilson | |
| 2,881,763 A | 4/1959 | Robbins | |
| 2,921,585 A | 1/1960 | Schumann | |
| 3,037,509 A | 6/1962 | Schutz | |
| 3,085,573 A | 4/1963 | Meyer et al. | |
| 3,214,869 A | 11/1965 | Stryker | |
| 3,468,079 A | 9/1969 | Kaufman | |
| 3,476,112 A | 11/1969 | Elstein | |
| 3,481,677 A | 12/1969 | Abrahamson | |
| 3,505,993 A | 4/1970 | Lewes et al. | |
| 3,560,100 A | 2/1971 | Spatz | |
| 3,574,239 A | 4/1971 | Sollerud | |
| 3,715,838 A | 2/1973 | Young et al. | |
| 3,865,352 A | 2/1975 | Nelson et al. | |
| 3,866,264 A | 2/1975 | Engquist | |
| 3,930,598 A | 1/1976 | Slagle | |
| 3,948,265 A | 4/1976 | Al Ani | |
| 3,964,212 A | 6/1976 | Karden | |
| 3,968,789 A | 7/1976 | Simoncini | |
| 3,977,084 A | 8/1976 | Sloan | |
| 4,121,388 A | 10/1978 | Wilson | |
| 4,155,721 A | 5/1979 | Fletcher | |
| 4,170,821 A | 10/1979 | Booth | |
| 4,182,329 A | 1/1980 | Smit et al. | |
| 4,203,431 A | 5/1980 | Abura et al. | |
| 4,216,233 A | 8/1980 | Stein | |
| 4,225,254 A | 9/1980 | Holberg et al. | |
| 4,289,158 A | 9/1981 | Nehring | |
| 4,299,219 A | 11/1981 | Norris, Jr. | |
| 4,342,522 A | 8/1982 | Mackles | |
| 4,378,804 A | 4/1983 | Cortese | |
| 4,500,222 A | 2/1985 | Clading-Boel | |
| 4,560,373 A | 12/1985 | Sugino et al. | |
| 4,646,480 A | 3/1987 | Williams | |
| 4,646,482 A | 3/1987 | Chitjian | |
| 4,655,743 A | 4/1987 | Hyde | |
| 4,676,749 A | 6/1987 | Mabille | |
| 4,706,676 A | 11/1987 | Peck | |
| 4,718,467 A | 1/1988 | Di Gianfilippo et al. | |
| 4,754,756 A | 7/1988 | Shelanski | |
| 4,757,814 A | 7/1988 | Wang et al. | |
| 4,764,362 A | 8/1988 | Barchas | |
| 4,795,421 A | 1/1989 | Blasius, Jr. et al. | |
| 4,811,734 A | 3/1989 | McGurk-Burleson et al. | |
| 4,836,192 A | 6/1989 | Abbate | |
| 4,875,287 A | 10/1989 | Creasy et al. | |
| 4,886,078 A | 12/1989 | Shiffman | |
| 4,887,994 A | 12/1989 | Bedford | |
| 4,900,316 A | 2/1990 | Yamamoto | |
| 4,917,086 A | 4/1990 | Feltovich et al. | |
| 4,925,450 A | 5/1990 | Imonti et al. | |
| 4,940,350 A | 7/1990 | Kim | |
| 4,957,747 A | 9/1990 | Stiefel | |
| 5,006,004 A | 4/1991 | Dirksing et al. | |
| 5,006,339 A | 4/1991 | Bargery et al. | |
| 5,012,797 A | 5/1991 | Clarke | |
| 5,035,089 A | 7/1991 | Tillman et al. | |
| 5,037,431 A | 8/1991 | Summers et al. | |
| 5,037,432 A | 8/1991 | Molinari | |
| 5,054,339 A | 10/1991 | Yacowitz | |
| 5,100,412 A | 3/1992 | Rosso | |
| 5,100,424 A | 3/1992 | Jang | |
| 5,119,839 A | 6/1992 | Rudolph | |
| 5,122,153 A | 6/1992 | Harrel | |
| 5,171,215 A | 12/1992 | Flanagan | |
| 5,192,269 A | 3/1993 | Poli et al. | |
| 5,207,234 A | 5/1993 | Rosso | |
| 5,222,956 A | 6/1993 | Waldron | |
| 5,242,433 A | 9/1993 | Smith et al. | |
| 5,254,109 A | 10/1993 | Smith et al. | |
| 5,368,581 A | 11/1994 | Smith et al. | |
| 5,387,215 A | 2/1995 | Fisher | |
| 5,391,151 A | 2/1995 | Wilmot | |
| 5,417,674 A | 5/1995 | Smith et al. | |
| 5,419,772 A | 5/1995 | Teitz et al. | |
| 5,441,490 A | 8/1995 | Svedman | |
| 5,460,620 A | 10/1995 | Smith et al. | |
| 5,470,323 A | 11/1995 | Smith et al. | |
| 5,484,427 A | 1/1996 | Gibbons | |
| 5,490,736 A | 2/1996 | Haber et al. | |
| 5,512,044 A | 4/1996 | Duer | |
| 5,562,642 A | 10/1996 | Smith et al. | |
| 5,562,643 A | 10/1996 | Johnson | |
| 5,611,687 A | 3/1997 | Wagner | |
| 5,612,797 A | 3/1997 | Clarke | |
| 5,674,235 A | 10/1997 | Parisi | |
| 5,676,643 A | 10/1997 | Cann et al. | |
| 5,676,648 A | 10/1997 | Henley | |
| 5,683,971 A | 11/1997 | Rose et al. | |
| 5,697,920 A | 12/1997 | Gibbons | |
| 5,707,383 A | 1/1998 | Bays | |
| 5,713,785 A | 2/1998 | Nishio | |
| 5,735,833 A | 4/1998 | Olson | |
| 5,759,185 A | 6/1998 | Grinberg | |
| 5,762,640 A | 6/1998 | Kajiwara et al. | |
| 5,779,519 A | 7/1998 | Oliver | |
| 5,800,446 A | 9/1998 | Banuchi | |
| 5,807,353 A | 9/1998 | Schmitz | |
| 5,810,842 A | 9/1998 | Di Fiore et al. | |
| 5,813,416 A | 9/1998 | Rudolph | |
| 5,817,050 A | 10/1998 | Klein | |
| 5,834,510 A | 11/1998 | Yu et al. | |

(56) References Cited

U.S. PATENT DOCUMENTS

| | | |
|---|---|---|
| 5,846,215 A | 12/1998 | Zygmont |
| 5,848,998 A | 12/1998 | Marasco, Jr. |
| 5,857,995 A | 1/1999 | Thomas et al. |
| 5,861,142 A | 1/1999 | Schick |
| 5,873,881 A | 2/1999 | McEwen et al. |
| 5,879,323 A | 3/1999 | Henley |
| 5,882,201 A | 3/1999 | Salem |
| 5,885,260 A | 3/1999 | Mehl, Sr. et al. |
| 5,908,401 A | 6/1999 | Henley |
| 5,919,152 A | 7/1999 | Zygmont |
| 5,954,730 A | 9/1999 | Bernabei |
| 5,971,999 A | 10/1999 | Naldoni |
| 5,980,555 A | 11/1999 | Barbut et al. |
| 6,019,749 A | 2/2000 | Fields et al. |
| 6,023,639 A | 2/2000 | Hakky et al. |
| 6,024,733 A | 2/2000 | Eggers et al. |
| 6,027,402 A | 2/2000 | Oliver |
| 6,039,745 A | 3/2000 | Di Fiore et al. |
| 6,042,552 A | 3/2000 | Cornier |
| 6,080,165 A | 6/2000 | DeJacma |
| 6,080,166 A | 6/2000 | McEwen et al. |
| 6,090,085 A | 7/2000 | Mehl, Sr. et al. |
| 6,120,512 A | 9/2000 | Bernabei |
| 6,129,701 A | 10/2000 | Cimino |
| 6,136,008 A | 10/2000 | Becker et al. |
| 6,139,553 A | 10/2000 | Dotan |
| 6,139,554 A | 10/2000 | Karkar et al. |
| 6,142,155 A | 11/2000 | Rudolph |
| 6,149,634 A | 11/2000 | Bernabei |
| 6,159,226 A | 12/2000 | Kim |
| 6,162,218 A | 12/2000 | Elbrecht et al. |
| 6,162,232 A | 12/2000 | Shadduck |
| 6,165,059 A | 12/2000 | Parkin et al. |
| 6,183,451 B1 | 2/2001 | Mehl, Sr. et al. |
| 6,183,483 B1 | 2/2001 | Chang |
| 6,193,589 B1 | 2/2001 | Khalaj |
| 6,196,982 B1 | 3/2001 | Ball |
| 6,231,593 B1 | 5/2001 | Meserol |
| 6,235,039 B1 | 5/2001 | Parkin et al. |
| 6,238,275 B1 | 5/2001 | Metcalf et al. |
| 6,241,739 B1 | 6/2001 | Waldron |
| 6,264,666 B1 | 7/2001 | Coleman et al. |
| 6,277,128 B1 | 8/2001 | Muldner |
| 6,283,978 B1 | 9/2001 | Cheski et al. |
| 6,299,620 B1 | 10/2001 | Shadduck |
| 6,306,119 B1 | 10/2001 | Weber et al. |
| 6,306,147 B1 | 10/2001 | Bernabei et al. |
| 6,322,548 B1 | 11/2001 | Payne et al. |
| 6,322,568 B1 | 11/2001 | Bernabe et al. |
| 6,332,886 B1 | 12/2001 | Green et al. |
| 6,368,333 B2 | 4/2002 | Bernabei et al. |
| 6,387,103 B2 | 5/2002 | Shadduck |
| 6,401,289 B1 | 6/2002 | Herbert |
| 6,409,736 B1 | 6/2002 | Bernabei |
| 6,410,599 B1 | 6/2002 | Johnson |
| RE37,796 E | 7/2002 | Henley |
| 6,414,032 B1 | 7/2002 | Johnson |
| 6,420,431 B1 | 7/2002 | Johnson |
| 6,423,078 B1 | 7/2002 | Bays et al. |
| 6,423,750 B1 | 7/2002 | Johnson |
| 6,432,113 B1 | 8/2002 | Parkin et al. |
| 6,432,114 B1 | 8/2002 | Rosso |
| 6,471,712 B2 | 10/2002 | Burres |
| 6,477,410 B1 | 11/2002 | Henley et al. |
| 6,482,212 B1 | 11/2002 | Bernabei et al. |
| 6,488,646 B1 | 12/2002 | Zygmont |
| 6,494,856 B1 | 12/2002 | Zygmont |
| 6,500,183 B1 | 12/2002 | Waldron |
| 6,503,256 B2 | 1/2003 | Parkin et al. |
| 6,508,813 B1 | 1/2003 | Altshuler |
| 6,511,486 B2 | 1/2003 | Mercier et al. |
| 6,514,262 B1 | 2/2003 | Di Fiore et al. |
| 6,527,783 B1 | 3/2003 | Ignon |
| 6,535,761 B2 | 3/2003 | Bernabei |
| 6,537,242 B1 | 3/2003 | Palmer |
| 6,540,757 B1 | 4/2003 | Hruska et al. |
| 6,562,013 B1 | 5/2003 | Marasco, Jr. |
| 6,562,050 B1 | 5/2003 | Owen |
| 6,564,093 B1 | 5/2003 | Ostrow et al. |
| 6,565,535 B2 | 5/2003 | Zaias et al. |
| 6,582,442 B2 | 6/2003 | Simon et al. |
| 6,589,218 B1 | 7/2003 | Garcia |
| 6,592,595 B1 | 7/2003 | Mallett et al. |
| 6,626,445 B2 | 9/2003 | Murphy et al. |
| 6,629,927 B1 | 10/2003 | Mesaros et al. |
| 6,629,983 B1 | 10/2003 | Ignon |
| 6,641,591 B1 | 11/2003 | Shadduck |
| 6,645,184 B1 | 11/2003 | Zelickson et al. |
| 6,652,888 B2 | 11/2003 | Rhoades |
| 6,666,874 B2 | 12/2003 | Heitzmann et al. |
| 6,673,081 B1 | 1/2004 | Tavger et al. |
| 6,673,082 B2 | 1/2004 | Mallett et al. |
| D486,915 S | 2/2004 | Warschewske et al. |
| 6,685,853 B1 | 2/2004 | Angelopoulous et al. |
| 6,687,537 B2 | 2/2004 | Bernabei |
| 6,695,853 B2 | 2/2004 | Karasiuk |
| 6,735,470 B2 | 5/2004 | Henley et al. |
| 6,743,211 B1 | 6/2004 | Prausnitz et al. |
| 6,743,215 B2 | 6/2004 | Bernabei |
| 6,764,493 B1 | 7/2004 | Weber et al. |
| D496,101 S | 9/2004 | Davison |
| 6,800,083 B2 | 10/2004 | Hiblar et al. |
| 6,869,611 B1 | 3/2005 | Kligman et al. |
| 6,905,487 B2 | 6/2005 | Zimmerman |
| 6,911,031 B2 | 6/2005 | Muldner |
| 6,926,681 B1 | 8/2005 | Ramey et al. |
| 6,938,805 B2 | 9/2005 | Brincat |
| 6,942,649 B2 | 9/2005 | Ignon et al. |
| 6,960,206 B2 | 11/2005 | Keane |
| 7,001,355 B2 | 2/2006 | Nunomura et al. |
| 7,004,933 B2 | 2/2006 | McDaniel |
| 7,044,938 B2 | 5/2006 | La Bianco et al. |
| 7,051,907 B2 | 5/2006 | Brincat |
| 7,052,503 B2 | 5/2006 | Bernabei |
| D522,360 S | 6/2006 | Caserta et al. |
| 7,069,073 B2 | 6/2006 | Henley et al. |
| 7,070,488 B2 | 7/2006 | Suissa et al. |
| 7,083,580 B2 | 8/2006 | Bernabei |
| 7,087,063 B2 | 8/2006 | Carson et al. |
| 7,094,252 B2 | 8/2006 | Koop |
| 7,115,275 B2 | 10/2006 | Clarot et al. |
| 7,135,011 B2 | 11/2006 | Powers et al. |
| 7,153,311 B2 | 12/2006 | Chung |
| 7,166,086 B2 | 1/2007 | Haider et al. |
| 7,197,359 B1 | 3/2007 | Tokudome et al. |
| 7,198,623 B2 | 4/2007 | Fischer et al. |
| 7,232,444 B2 | 6/2007 | Chang |
| 7,241,208 B2 | 7/2007 | Suissa et al. |
| D553,005 S | 10/2007 | Py et al. |
| 7,276,051 B1 | 10/2007 | Henley et al. |
| 7,293,930 B2 | 11/2007 | Chuang |
| 7,314,326 B2 | 1/2008 | Rosenberg |
| 7,316,657 B2 | 1/2008 | Kleinhenz et al. |
| 7,316,671 B2 | 1/2008 | Lastovich et al. |
| 7,318,828 B1 | 1/2008 | Revivo |
| 7,320,691 B2 | 1/2008 | Pilcher et al. |
| 7,320,801 B2 | 1/2008 | Kelly |
| 7,354,423 B2 | 4/2008 | Zelickson et al. |
| 7,364,565 B2 | 4/2008 | Freeman |
| 7,384,405 B2 | 6/2008 | Rhoades |
| 7,422,567 B2 | 9/2008 | Lastovich et al. |
| 7,427,273 B2 | 9/2008 | Mitsui |
| 7,458,944 B2 | 12/2008 | Liste et al. |
| D584,151 S | 1/2009 | Murphy |
| 7,476,205 B2 | 1/2009 | Erdmann |
| 7,477,938 B2 | 1/2009 | Sun et al. |
| 7,482,314 B2 | 1/2009 | Grimes et al. |
| 7,485,125 B2 | 2/2009 | Sjostrom |
| 7,489,989 B2 | 2/2009 | Sukhanov et al. |
| 7,507,228 B2 | 3/2009 | Sun et al. |
| 7,582,067 B2 | 9/2009 | Van Acker |
| 7,597,900 B2 | 10/2009 | Zimmer et al. |
| 7,597,901 B2 | 10/2009 | Clarot et al. |
| 7,658,742 B2 | 2/2010 | Karasiuk |

(56) References Cited

U.S. PATENT DOCUMENTS

| | | |
|---|---|---|
| 7,678,120 B2 | 3/2010 | Shadduck |
| 7,744,582 B2 | 6/2010 | Sadowski et al. |
| 7,789,886 B2 | 9/2010 | Shadduck |
| 7,837,695 B2 | 11/2010 | Hart et al. |
| 7,857,806 B2 | 12/2010 | Karpowicz et al. |
| 7,901,373 B2 | 3/2011 | Tavger |
| 7,951,156 B2 | 5/2011 | Karasiuk |
| 7,993,333 B2 | 8/2011 | Oral et al. |
| 8,025,669 B1 | 9/2011 | David et al. |
| RE42,960 E | 11/2011 | Waldron |
| 8,048,089 B2 | 11/2011 | Ignon et al. |
| 8,066,716 B2 | 11/2011 | Shadduck |
| 8,088,085 B2 | 1/2012 | Thiebaut et al. |
| 8,105,295 B2 | 1/2012 | Blott et al. |
| 8,128,638 B2 | 3/2012 | Karasiuk et al. |
| D664,254 S | 7/2012 | Yokoyama et al. |
| 8,221,437 B2 | 7/2012 | Waldron et al. |
| 8,231,292 B2 | 7/2012 | Rabe et al. |
| 8,236,008 B2 | 8/2012 | Boone, III et al. |
| 8,277,287 B2 | 10/2012 | Hart |
| 8,337,513 B2 | 12/2012 | Shadduck |
| 8,343,116 B2 | 1/2013 | Ignon et al. |
| D678,783 S | 3/2013 | Wilcox et al. |
| 8,475,507 B2 | 7/2013 | Dewey et al. |
| 8,573,874 B2 | 11/2013 | Neuner |
| 8,579,916 B2 | 11/2013 | Cheney |
| 8,721,662 B2 | 5/2014 | Karasiuk |
| D709,617 S | 7/2014 | Iliesco de Grimaldi et al. |
| 8,814,836 B2 | 8/2014 | Ignon et al. |
| 8,858,570 B2 | 10/2014 | Chang |
| 8,939,669 B2 | 1/2015 | Le et al. |
| D722,172 S | 2/2015 | Amemiya et al. |
| 8,945,104 B2 | 2/2015 | Boone, III et al. |
| 9,050,133 B1 | 6/2015 | Boone, III et al. |
| 9,056,193 B2 | 6/2015 | Ignon et al. |
| 9,072,533 B2 | 7/2015 | Liu et al. |
| D743,558 S | 11/2015 | Kim et al. |
| 9,468,464 B2 | 10/2016 | Shadduck |
| 9,474,886 B2 | 10/2016 | Ignon et al. |
| 9,486,615 B2 | 11/2016 | Ignon et al. |
| 9,498,610 B2 | 11/2016 | Ignon et al. |
| 9,517,085 B2 | 12/2016 | Karasiuk |
| 9,550,052 B2 | 1/2017 | Ignon et al. |
| 9,566,088 B2 | 2/2017 | Ignon et al. |
| D787,054 S | 5/2017 | Rini et al. |
| 9,642,997 B2 | 5/2017 | Ignon et al. |
| 9,662,482 B2 | 5/2017 | Ignon et al. |
| 9,700,684 B2 | 7/2017 | Vlodaver et al. |
| 9,731,053 B2 | 8/2017 | Alai |
| 9,775,645 B2 | 10/2017 | Boone, III |
| 9,775,646 B2 | 10/2017 | Shadduck |
| 9,814,868 B2 | 11/2017 | Ignon et al. |
| 9,833,261 B2 | 12/2017 | Boone, III et al. |
| 9,861,442 B2 | 1/2018 | Tankovich et al. |
| D811,381 S | 2/2018 | Morohoshi et al. |
| 9,918,727 B1 | 3/2018 | Boone, III et al. |
| 9,949,552 B2 | 4/2018 | Rabe et al. |
| 9,950,147 B2 | 4/2018 | Mehta |
| 9,955,769 B2 | 5/2018 | Rabe et al. |
| D822,845 S | 7/2018 | Shimobayashi et al. |
| 10,035,007 B2 | 7/2018 | Ignon et al. |
| D825,763 S | 8/2018 | Lim et al. |
| 10,076,646 B2 | 9/2018 | Casasanta, III et al. |
| 10,130,390 B1 | 11/2018 | Hart et al. |
| D836,781 S | 12/2018 | Meurer et al. |
| 10,172,644 B2 | 1/2019 | Ignon et al. |
| 10,179,229 B2 | 1/2019 | Ignon et al. |
| 10,188,193 B2 | 1/2019 | Rabe et al. |
| 10,206,743 B2 | 2/2019 | Tankovich et al. |
| 10,220,122 B2 | 3/2019 | Clark, III et al. |
| 10,238,812 B2 | 3/2019 | Ignon |
| 10,251,675 B2 | 4/2019 | Ignon et al. |
| D851,759 S | 6/2019 | Jones et al. |
| 10,314,378 B2 | 6/2019 | Rabe et al. |
| D852,962 S | 7/2019 | Chang |
| 10,357,641 B2 | 7/2019 | Ignon et al. |
| 10,357,642 B2 | 7/2019 | Ignon et al. |
| 10,334,933 B2 | 8/2019 | Rosario et al. |
| 10,369,073 B2 | 8/2019 | Rosario et al. |
| D861,913 S | 10/2019 | Stamm et al. |
| 10,456,321 B2 | 10/2019 | Shadduck |
| 10,456,567 B2 | 10/2019 | Streeter |
| D867,587 S | 11/2019 | Holtz |
| 10,485,983 B1 | 11/2019 | Boone, III et al. |
| D868,981 S | 12/2019 | Salamon et al. |
| 10,524,835 B2 | 1/2020 | Shadduck et al. |
| 10,556,096 B2 | 2/2020 | Ignon et al. |
| 10,556,097 B2 | 2/2020 | Ignon et al. |
| 10,667,985 B2 | 6/2020 | Decaux et al. |
| D893,024 S | 8/2020 | Whiteside |
| 10,737,080 B2 | 8/2020 | Patterson |
| 10,758,261 B2 | 9/2020 | Richardson |
| 10,918,190 B2 | 2/2021 | Laudati |
| 10,946,191 B2 | 3/2021 | Cazares Delgadillo |
| 10,993,743 B2 | 5/2021 | Ignon et al. |
| 11,020,577 B2 | 6/2021 | Ignon et al. |
| 2001/0023351 A1 | 9/2001 | Eilers |
| 2001/0037118 A1 | 11/2001 | Shadduck |
| 2001/0049511 A1 | 12/2001 | Coleman et al. |
| 2002/0016601 A1 | 2/2002 | Shadduck |
| 2002/0041891 A1 | 4/2002 | Cheski |
| 2002/0058952 A1 | 5/2002 | Weber et al. |
| 2002/0107527 A1 | 8/2002 | Burres |
| 2002/0128663 A1 | 9/2002 | Mercier et al. |
| 2002/0133110 A1 | 9/2002 | Citow |
| 2002/0133176 A1 | 9/2002 | Parkin et al. |
| 2002/0151826 A1 | 10/2002 | Ramey et al. |
| 2002/0151908 A1 | 10/2002 | Mallett, Sr. et al. |
| 2002/0162863 A1 | 11/2002 | Brincat |
| 2002/0188261 A1 | 12/2002 | Hruska |
| 2003/0012415 A1 | 1/2003 | Cossel |
| 2003/0018252 A1 | 1/2003 | Duchon et al. |
| 2003/0060834 A1 | 3/2003 | Muldner |
| 2003/0093040 A1 | 5/2003 | Mikszta et al. |
| 2003/0093089 A1 | 5/2003 | Greenberg |
| 2003/0097139 A1 | 5/2003 | Karasiuk |
| 2003/0167032 A1 | 9/2003 | Ignon |
| 2003/0187462 A1 | 10/2003 | Chang |
| 2003/0208159 A1 | 11/2003 | Ignon et al. |
| 2003/0212127 A1 | 11/2003 | Glassman et al. |
| 2003/0212415 A1 | 11/2003 | Karasiuk |
| 2004/0010222 A1 | 1/2004 | Nunomura et al. |
| 2004/0010269 A1 | 1/2004 | Grimes et al. |
| 2004/0015139 A1 | 1/2004 | La Bianco |
| 2004/0087972 A1 | 5/2004 | Mulholland et al. |
| 2004/0092895 A1 | 5/2004 | Harmon |
| 2004/0092959 A1 | 5/2004 | Bernaz |
| 2004/0097967 A1 | 5/2004 | Ignon |
| 2004/0122447 A1 | 6/2004 | Harmon et al. |
| 2004/0127914 A1 | 7/2004 | Chung |
| 2004/0138680 A1 | 7/2004 | Twitchell et al. |
| 2004/0143274 A1 | 7/2004 | Shadduck |
| 2004/0162565 A1 | 8/2004 | Carson et al. |
| 2004/0166172 A1 | 8/2004 | Rosati et al. |
| 2004/0219179 A1 | 11/2004 | McDaniel |
| 2004/0236291 A1 | 11/2004 | Zelickson et al. |
| 2004/0243149 A1 | 12/2004 | Lee, Jr. |
| 2004/0254587 A1 | 12/2004 | Park |
| 2004/0267285 A1 | 12/2004 | Chang |
| 2005/0037034 A1 | 2/2005 | Rhoades |
| 2005/0038448 A1 | 2/2005 | Chung |
| 2005/0059940 A1 | 3/2005 | Weber et al. |
| 2005/0084509 A1 | 4/2005 | Bernstein |
| 2005/0148958 A1 | 7/2005 | Rucinski |
| 2005/0203111 A1 | 9/2005 | David |
| 2005/0209611 A1 | 9/2005 | Greenberg |
| 2005/0283176 A1 | 12/2005 | Law |
| 2006/0002960 A1 | 1/2006 | Zoeteweij et al. |
| 2006/0116674 A1 | 6/2006 | Goble et al. |
| 2006/0161178 A1 | 7/2006 | Lee |
| 2006/0189964 A1 | 8/2006 | Anderson |
| 2006/0191562 A1 | 8/2006 | Numomura |
| 2006/0200099 A1 | 9/2006 | La Bianco et al. |
| 2006/0200172 A1 | 9/2006 | Shadduck |

(56) References Cited

U.S. PATENT DOCUMENTS

| | | |
|---|---|---|
| 2006/0200173 A1 | 9/2006 | Shadduck |
| 2006/0212029 A1 | 9/2006 | Villacampa et al. |
| 2006/0222445 A1 | 10/2006 | Chuang |
| 2006/0253125 A1 | 11/2006 | Ignon |
| 2006/0264893 A1 | 11/2006 | Sage, Jr. et al. |
| 2006/0269580 A1 | 11/2006 | Cole et al. |
| 2007/0005078 A1 | 1/2007 | Hart et al. |
| 2007/0043382 A1 | 2/2007 | Cheney |
| 2007/0065515 A1 | 3/2007 | Key |
| 2007/0088371 A1 | 4/2007 | Karasiuk |
| 2007/0123808 A1 | 5/2007 | Rhoades |
| 2007/0139630 A1 | 6/2007 | Kiernan et al. |
| 2007/0154502 A1 | 7/2007 | Hattendorf et al. |
| 2007/0156124 A1 | 7/2007 | Ignon et al. |
| 2007/0178121 A1 | 8/2007 | First et al. |
| 2007/0198031 A1 | 8/2007 | Kellogg |
| 2007/0208353 A1 | 9/2007 | Shadduck |
| 2007/0239173 A1 | 10/2007 | Khalaj |
| 2008/0027328 A1 | 1/2008 | Klopotek et al. |
| 2008/0091179 A1 | 4/2008 | Durkin et al. |
| 2008/0103563 A1 | 5/2008 | Powell |
| 2008/0119781 A1 | 5/2008 | King |
| 2008/0132914 A1 | 6/2008 | Bossard et al. |
| 2008/0139974 A1 | 6/2008 | Da Silva |
| 2008/0154161 A1 | 6/2008 | Abbott |
| 2008/0193493 A1 | 8/2008 | Rhoades |
| 2008/0200861 A1 | 8/2008 | Shalev et al. |
| 2008/0208146 A1 | 8/2008 | Brandwein et al. |
| 2008/0214987 A1 | 9/2008 | Xu |
| 2008/0215068 A1 | 9/2008 | Hart et al. |
| 2008/0221548 A1 | 9/2008 | Danenberg et al. |
| 2008/0243039 A1 | 10/2008 | Rhoades |
| 2008/0287864 A1 | 11/2008 | Rosenberg |
| 2008/0300529 A1 | 12/2008 | Reinstein |
| 2008/0300552 A1 | 12/2008 | Cichocki et al. |
| 2009/0048557 A1 | 2/2009 | Yeshurun et al. |
| 2009/0053390 A1 | 2/2009 | Sakou et al. |
| 2009/0062815 A1 | 3/2009 | Karasiuk et al. |
| 2009/0099091 A1 | 4/2009 | Hantash |
| 2009/0099093 A1 | 4/2009 | Hantash |
| 2009/0124985 A1 | 5/2009 | Hasenoehrl et al. |
| 2009/0138026 A1 | 5/2009 | Wu |
| 2009/0177171 A1 | 7/2009 | Ignon et al. |
| 2009/0192442 A1* | 7/2009 | Ignon .......... A61M 35/003 604/22 |
| 2009/0222023 A1 | 9/2009 | Boone, III et al. |
| 2010/0023003 A1 | 1/2010 | Mulholland |
| 2010/0045427 A1 | 2/2010 | Boone, III et al. |
| 2010/0049177 A1 | 2/2010 | Boone, III et al. |
| 2010/0049210 A1 | 2/2010 | Boone, III et al. |
| 2010/0217357 A1 | 8/2010 | Da Silva |
| 2010/0305495 A1 | 12/2010 | Anderson et al. |
| 2011/0054490 A1 | 3/2011 | Hart |
| 2011/0066162 A1 | 3/2011 | Cohen |
| 2011/0082415 A1 | 4/2011 | Ignon et al. |
| 2011/0295273 A1 | 12/2011 | Waldron et al. |
| 2012/0022435 A1 | 1/2012 | Ignon et al. |
| 2012/0041338 A1 | 2/2012 | Chickering, III et al. |
| 2012/0136374 A1 | 5/2012 | Karasiuk |
| 2013/0004230 A1 | 1/2013 | Kirk, III et al. |
| 2013/0018317 A1 | 1/2013 | Bobroff et al. |
| 2013/0066336 A1 | 3/2013 | Boone, III et al. |
| 2013/0096577 A1 | 4/2013 | Shadduck |
| 2013/0102978 A1 | 4/2013 | Ignon et al. |
| 2013/0144207 A1 | 6/2013 | Gonon |
| 2013/0144280 A1 | 6/2013 | Eckhouse et al. |
| 2013/0158547 A1 | 6/2013 | David |
| 2014/0079686 A1 | 3/2014 | Barman et al. |
| 2014/0234004 A1 | 8/2014 | Thorpe et al. |
| 2014/0343481 A1 | 11/2014 | Ignon |
| 2014/0343574 A1 | 11/2014 | Ignon et al. |
| 2014/0378887 A1 | 12/2014 | Chang et al. |
| 2015/0032047 A1 | 1/2015 | Ignon et al. |
| 2015/0230824 A1 | 8/2015 | Shadduck |
| 2015/0230825 A1 | 8/2015 | Shadduck |
| 2015/0231379 A1 | 8/2015 | Ignon et al. |
| 2015/0265822 A1 | 9/2015 | Ignon et al. |
| 2015/0272632 A1 | 10/2015 | Seelig |
| 2015/0290442 A1 | 10/2015 | Ignon et al. |
| 2016/0018100 A1 | 1/2016 | Batt et al. |
| 2016/0038183 A1 | 2/2016 | Ignon et al. |
| 2016/0235257 A1 | 8/2016 | Daffer |
| 2016/0250415 A1 | 9/2016 | Yagi et al. |
| 2017/0036002 A1 | 2/2017 | Ignon et al. |
| 2017/0043150 A1 | 2/2017 | Kim |
| 2017/0065801 A1 | 3/2017 | Ignon et al. |
| 2017/0209894 A1 | 7/2017 | Sporrer |
| 2018/0140329 A1 | 5/2018 | Beijens et al. |
| 2018/0185675 A1 | 7/2018 | Kern et al. |
| 2018/0318568 A1 | 11/2018 | Ignon et al. |
| 2019/0070069 A1 | 3/2019 | Gertner et al. |
| 2019/0133642 A1 | 5/2019 | Ignon et al. |
| 2019/0143089 A1 | 5/2019 | Ignon et al. |
| 2019/0151637 A1 | 5/2019 | Groop et al. |
| 2019/0223914 A1 | 7/2019 | Ignon et al. |
| 2019/0336740 A1 | 11/2019 | Ignon et al. |
| 2020/0009007 A1 | 1/2020 | Shadduck |
| 2020/0016342 A1 | 1/2020 | Ignon |
| 2020/0171288 A1 | 6/2020 | Ignon et al. |
| 2020/0171289 A1 | 6/2020 | Ignon et al. |
| 2020/0179220 A1 | 6/2020 | Jablow |
| 2020/0289161 A1 | 9/2020 | Scooros |
| 2020/0316270 A1 | 10/2020 | Dijkstra et al. |
| 2020/0338586 A1 | 10/2020 | Park |
| 2020/0390468 A1 | 12/2020 | Alexander |
| 2021/0085367 A1 | 3/2021 | Shadduck et al. |
| 2021/0145481 A1 | 5/2021 | Ignon et al. |
| 2021/0154453 A1 | 5/2021 | Ignon et al. |
| 2021/0154454 A1 | 5/2021 | Ignon et al. |
| 2021/0154455 A1 | 5/2021 | Ignon et al. |
| 2021/0177463 A1 | 6/2021 | Ignon et al. |

FOREIGN PATENT DOCUMENTS

| | | |
|---|---|---|
| CA | 2 340 154 | 9/2002 |
| CN | 107920948 | 4/2018 |
| DE | 59 95 21 | 7/1934 |
| DE | 24 15 633 | 10/1975 |
| DE | 33 38 057 | 8/1984 |
| DE | 34 21 390 | 12/1985 |
| DE | 234 608 | 4/1986 |
| DE | 35 03 343 | 8/1986 |
| DE | 83 30 191 | 6/1987 |
| DE | 37 40 902 | 12/1988 |
| DE | 42 37 940 | 5/1993 |
| DE | 298 08 395 | 8/1998 |
| DE | 10 2004 015815 | 11/2005 |
| EP | 0 258 901 | 9/1987 |
| EP | 0 564 392 | 3/1993 |
| EP | 0 784 997 | 7/1997 |
| EP | 1238643 | 4/2000 |
| EP | 1 453 558 | 9/2004 |
| EP | 2544563 | 9/2015 |
| EP | 2 106 780 | 3/2016 |
| EP | 3 217 899 | 5/2016 |
| EP | 2240099 | 2/2018 |
| EP | 3 302 319 | 4/2018 |
| EP | 2967633 | 4/2018 |
| EP | 3319573 | 5/2018 |
| EP | 3 340 908 | 7/2018 |
| EP | 2451367 | 1/2020 |
| EP | 3388006 | 3/2020 |
| EP | 2618797 | 4/2020 |
| EP | 3237055 | 8/2020 |
| EP | 3795204 | 3/2021 |
| EP | 3437575 | 4/2021 |
| ES | 1 037 776 | 4/1998 |
| FR | 2 712 172 | 5/1995 |
| FR | 2 773 461 | 7/1999 |
| GB | 1 372 609 | 10/1974 |
| GB | 2306351 | 5/1997 |
| IT | 553 076 | 12/1956 |
| IT | 118 49 22 | 3/1985 |
| JP | S55-034863 | 8/1963 |

(56) References Cited

FOREIGN PATENT DOCUMENTS

| | | |
|---|---|---|
| JP | H05-042060 | 2/1993 |
| JP | 1993-088552 | 12/1993 |
| JP | 1997-294747 | 11/1997 |
| JP | 2003-534881 | 11/2003 |
| JP | 2003-339713 | 12/2003 |
| JP | 2004-275721 | 10/2004 |
| JP | 2006-503627 | 2/2006 |
| JP | 2006-204767 | 10/2006 |
| JP | 2010/042243 | 2/2010 |
| JP | 2012527967 | 11/2012 |
| JP | 5508285 | 3/2014 |
| JP | 2018-527052 | 9/2018 |
| KR | 20-0280320 | 7/2002 |
| KR | 10-20070070173 | 7/2007 |
| KR | 10-2018-0030607 | 3/2018 |
| KR | 10-1836310 | 3/2018 |
| WO | WO 1994/024980 | 11/1994 |
| WO | WO 1997/011650 | 3/1997 |
| WO | WO 2000/015300 | 3/2000 |
| WO | WO 00/79540 | 12/2000 |
| WO | WO 2001/93931 | 12/2001 |
| WO | WO 2003/073917 | 9/2003 |
| WO | WO 2004/037098 | 5/2004 |
| WO | WO 2005/070313 | 8/2005 |
| WO | WO 2006/018731 | 2/2006 |
| WO | WO 2006/031413 | 3/2006 |
| WO | WO 2007/114904 | 10/2007 |
| WO | WO 2009/088884 | 7/2009 |
| WO | WO 2009/097451 | 8/2009 |
| WO | WO 2011/006009 | 1/2011 |
| WO | WO 2011/110840 | 9/2011 |
| WO | WO 2012/145667 | 10/2012 |
| WO | WO 2014/091035 | 6/2014 |
| WO | WO 2014/151104 | 9/2014 |
| WO | WO 2016/106396 | 6/2016 |
| WO | WO 2017/007939 | 1/2017 |
| WO | WO 2021/018765 | 2/2021 |

OTHER PUBLICATIONS

File History of Reexamination No. 90/007,683 (Reexamination of U.S. Pat. No. 6,241,739, issued Jun. 5, 2001).

File History of Reexamination No. 90/013,284, filed Jul. 2, 2014 (Reexamination of U.S. Pat. No. 6,241,739, issued Jun. 5, 2001).

Cox III et al., Decreased Splatter in Dermabrasion, Arch Facial Plastic Surgery, Jan.-Mar. 2000, vol. 2, pp. 23-26.

Ditre et al., Effect of α-hydroxy acids on photoaged skin: A pilot clinical, histologic, and ultrastructural study, Journal of American Academy of Dermatology, Feb. 1996, vol. 34, No. 2, Part 1, pp. 187-195.

Harris et al., Combining Manual Dermasanding with Low Strength Trichloroacetic Acid to Improve Antinically Injured Skin, The Journal of Dermatologic Surgery and Oncology, Jul. 1994, vol. 20, No. 7, pp. 436-442.

HYDRAFACIAL® TOWER—User guide. Edge Systems. Revised Jun. 23, 2016. p. 16.

Microdermabrader Pepita Instruction Manual, Mattioli Engineering S.R.L., PEP_USA2.doc Rev 1.1, Sep. 29, 1997.

International Search Report and Written Opinion for related PCT appl. PCT/US14/24992 dated Jul. 21, 2014.

* cited by examiner

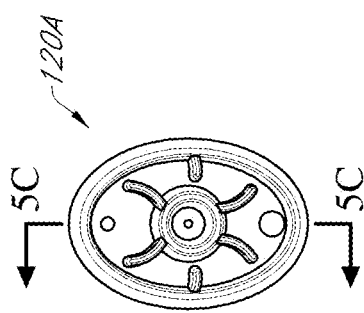
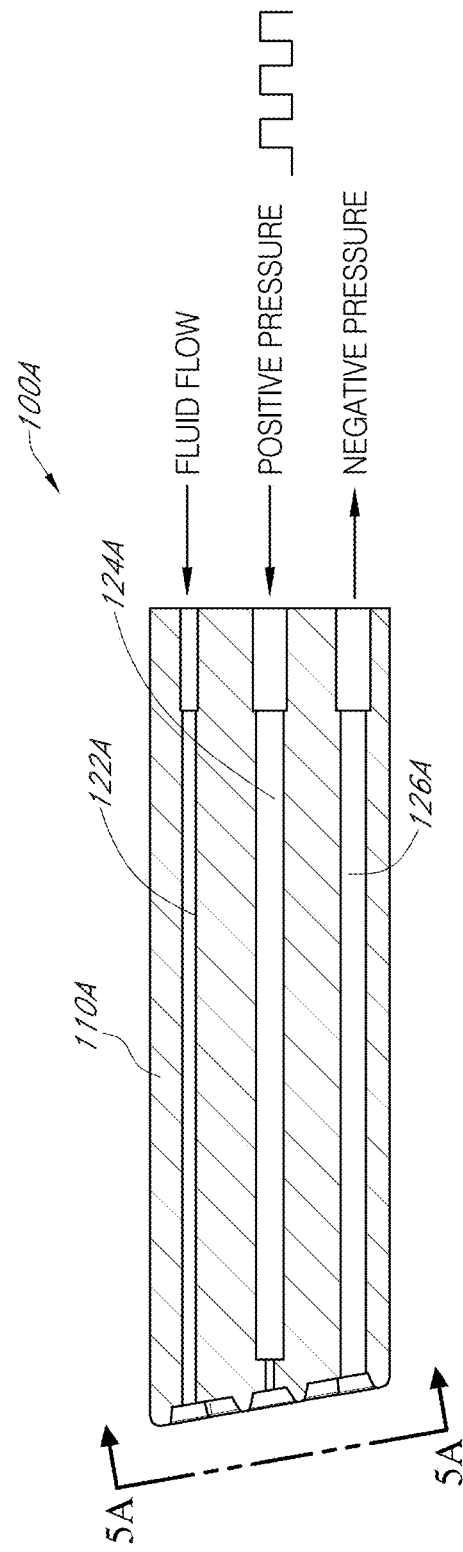

DEVICES, SYSTEMS AND METHODS FOR TREATING THE SKIN

CROSS-REFERENCE TO RELATED APPLICATIONS & INCORPORATION BY REFERENCE

This application is a continuation application of U.S. patent application Ser. No. 16/241,572 filed Jan. 7, 2019, which is a continuation application of U.S. patent application Ser. No. 14/774,641 filed Sep. 10, 2015 and issued as U.S. Pat. No. 10,172,644 on Jan. 8, 2019, which is the U.S. National Phase under 35 U.S.C. § 371 of International Application PCT/US2014/024992 filed Mar. 12, 2014, titled Devices, Systems and Methods for Treating the Skin, which claims the priority benefit under 35 U.S.C. § 119(e) of U.S. Provisional Application No. 61/791,157 filed Mar. 15, 2013, and U.S. Provisional Application No. 61/788,420 filed Mar. 15, 2013. Further, the entireties of U.S. patent application Ser. No. 12/346,582 filed Dec. 30, 2008 and issued on Jan. 1, 2013 as U.S. Pat. No. 8,343,116, and U.S. patent application Ser. No. 11/392,348 filed Mar. 29, 2006 and issued on Nov. 1, 2011 as U.S. Pat. No. 8,048,089, are hereby incorporated by reference herein and made a part of the present specification. The entireties of all of the foregoing are hereby incorporated by reference herein.

BACKGROUND

Field

This application relates generally to skin treatment, and more specifically, to apparatuses, systems and methods for treating a person's skin.

Description of the Related Art

Abrasion of the outer layer or epidermis of the skin is desirable to smooth or blend scars, blemishes, or other skin conditions that may be caused by, for example, acne, sun exposure, and aging. Standard techniques used to abrade the skin have generally been separated into two fields referred to as dermabrasion and microdermabrasion. Both techniques remove portions of the epidermis called the stratum corneum, which the body interprets as a mild injury. The body then replaces the lost skin cells, resulting in a new outer layer of skin. Additionally, despite the mild edema and erythema associated with the procedures, the skin looks and feels smoother because of the new outer layer of skin.

SUMMARY

According to some embodiments, a skin treatment system comprises a handheld device comprising a main body and a tip, wherein the tip is positioned along a distal end of the handheld device, a fluid delivery conduit positioned at least partially within an interior of the main body, the fluid delivery conduit placing the tip in fluid communication with a fluid source, a suction conduit positioned at least partially within an interior of the main body, the suction conduit placing the tip in fluid communication with a vacuum source, an air delivery conduit positioned at least partially within an interior of the main body, the air delivery conduit being configured to deliver air to the tip, wherein the tip comprises an outer ridge configured to contact a skin surface during a treatment procedure, wherein the tip further comprises an inner ridge, the inner ridge being completely surrounded by the outer ridge, wherein the outer ring and the inner ring define an annular region along the tip, wherein each of the fluid delivery conduit and the suction conduit include at least one port, the ports located within the annular region along the tip, and wherein the air delivery conduit is in fluid communication with an air delivery port, the air delivery port being located within an area surrounded by the inner ridge.

According to some embodiments, the air delivery conduit is configured to delivery air to the tip in a pulsed pattern, wherein air delivery to the tip enhances the passage of liquids through a subject's skin during use. In other embodiments, the air delivery conduit is configured to delivery air to the tip in a non-pulsed pattern. In some embodiments, the pulsed pattern of air delivery comprises alternating between a high pressure and a low pressure air flow. In some embodiments, both the high and low pressure air flows are above atmospheric pressure. In one embodiment, the low pressure air flow is a negative pressure relative to atmospheric pressure.

According to some embodiments, the pulsed air pattern comprises a step-like pattern. In some embodiments, the pulsed pattern does not comprise a step-like pattern (e.g., it comprises a sinusoidal, irregular, other pattern, etc.). In some embodiments, the system further comprises at least one additional suction port terminating at or near the inner ridge, the at least one additional suction port being configured to ensure that the inner ridge remains in contact with the subject's skin surface when the system is activated. According to some embodiments, a duty cycle of air delivered in a pulsed pattern is between 20 and 60% (between 25 and 40%). In one embodiment, a frequency of air delivered in a pulsed pattern is between 2 and 15 Hz.

According to some embodiments, the system further comprises a needle assembly located along the tip, the needle assembly comprising a plurality of needles configured to selectively penetrate a subject's skin during use. In some embodiments, the needle assembly is movable between a retracted position and expanded position. In one embodiment, the needle assembly is spring-biased in a retracted position. In one embodiment, the needle assembly is moved from a retracted position to an expanded position pneumatically, mechanically or by some other non-manual device or method. In some embodiments, a distal end of the needle assembly is located within an interior of the inner ridge.

According to some embodiments, one or more needles of a needle assembly are hollow. According to some embodiments, one or more needles of a needle assembly are solid. In some embodiments, the diameter of the needles is 0.001-0.005 inches (e.g., 0.010 inches). In some embodiments, a longitudinal position or orientation of the needles is adjustable. In some embodiments, a length of the needles is 0.05-5 mm (0.5-2.5 mm). In some embodiments, at least one of the needles is thermally conditioned (e.g., heated or cooled).

According to some embodiments, the tip comprises at least one abrasive member or portion configured to abrade skin tissue when the handheld device is moved relative to a subject's skin. In some embodiments, the abrasive member comprises a post, a spiral, a roughened surface and/or any other feature or member. In some embodiments, the abrasive member comprises a sharp edge or surface.

According to some embodiments, the fluid source comprises a cartridge, the cartridge being configured for attachment to the main body of the handheld device. In some embodiments, the fluid source comprises a manifold system that is in fluid communication with the fluid delivery conduit.

According to some embodiments, a method of treating skin comprises moving a tip of a handheld device along a targeted skin surface of a subject, wherein at least one suction region of the tip is configured to form a suction seal with the subject's skin during use, activating a suction source to engage at least a portion of the tip with the subject's skin, wherein activating a suction source draws a volume of at least one treatment media to the skin surface being treated along the at least one suction region of the tip, providing air to a skin surface of the subject through the tip while maintaining a suction seal between the tip and the subject's skin surface along the at least one suction region.

According to some embodiments, air is delivered in a pulsed pattern. In some embodiments, the pulsed air pattern comprises alternating between a high pressure and a low pressure air flow. In one embodiment, both the high and low pressure air flows are above atmospheric pressure. In one embodiment, the low pressure air flow is a negative pressure relative to atmospheric pressure.

According to some embodiments, the method further comprises abrading skin, wherein the tip comprises at least one abrading member, the at least one abrading member being configured to abrade skin when moved relative to a skin surface.

According to some embodiments, the method further comprises at least partially penetrating a skin surface of a subject using a plurality of needles. In one embodiment, the needles are positioned on a movable needle assembly, the movable needle assembly being located along the tip of the handheld device.

According to some embodiments, the method further comprises preparing the skin surface of the subject prior to moving the tip of the handheld device along the skin surface. In some embodiments, preparing the skin comprising heating or cooling the skin surface.

According to some embodiments, a method of treating a skin surface of a subject comprises heating a skin surface, abrading native skin tissue of a subject using a microdermabrasion device, wherein using the microdermabrasion device comprises moving the microdermabrasion device relative to the skin surface while simultaneously delivering at least one treatment fluid to the skin surface being treated and cooling the abraded skin surface.

According to some embodiments, heating and cooling the skin surface is performed using a thermal conditioning handheld assembly. In one embodiment, the thermal conditioning handheld assembly is configured to be selectively heated or cooled conductively (e.g., using at least one thermoelectric device) within a thermal recharging station. In some embodiments, the at least one treatment fluid is delivered to the skin surface using and through the microdermabrasion device. The method further comprising exposing the skin surface to at least one additional treatment (e.g., exposure to a source of energy, such as, radiofrequency, ultrasound, microwave, laser, etc.).

According to some embodiments, a skin surface of a subject comprising abrading native skin tissue of a subject using a microdermabrasion device, wherein using the microdermabrasion device comprises moving the microdermabrasion device relative to the skin surface while simultaneously delivering at least one treatment fluid to the skin surface being treated and exposing the skin surface to at least one additional treatment procedure.

According to some embodiments, the at least one additional treatment procedure comprises exposing the skin surface to an energy source. In one embodiment, the energy source comprises at least one of radiofrequency, ultrasound, microwave, laser and/or the like. In some embodiments, the at least one additional treatment procedure comprises delivering air to the skin surface. In some embodiments, air is delivered to the skin surface by and through the microdermabrasion device. In one embodiment, the at least one additional treatment procedure comprises exposing the skin surface to light. In some embodiments, the at least one additional treatment procedure comprises heating or cooling the skin surface.

According to some embodiments, a microdermabrasion device for treating skin comprises a handpiece assembly having a distal end and a proximal end. The handpiece assembly includes at least one delivery conduit and at least one waste conduit. The microdermabrasion device additionally comprises a tip configured to be positioned along the distal end of the handpiece assembly, wherein the tip is adapted to contact skin surface. According to some embodiments, the microdermabrasion device further includes a flow control device or feature included within the handpiece assembly to regulate the flow of fluids through the delivery conduit. In several embodiments, the tip comprises a lip, a first opening in fluid communication with the fluid delivery conduit and a second opening in fluid communication with the waste conduit. In one embodiment, the device includes one or more abrasive elements positioned along a distal end of the tip, wherein the abrasive elements are configured to selectively remove skin as the tip is moved relative to a skin surface. In some embodiments, the first opening, the second opening and the abrasive elements of the tip are positioned within an interior of an outer periphery formed by the lip. In some embodiments, the waste conduit is in fluid communication with a vacuum source to selectively remove debris away from the tip. In one embodiment, the delivery conduit is in fluid communication with the at least one waste conduit and the vacuum source when the lip contacts a skin surface. In some embodiments, the delivery conduit is configured to selectively deliver at least one time-release material to the skin surface being treated.

According to some embodiments, the flow control device comprises a valve (e.g., a needle valve). In some embodiments, the abrasive element comprises a protruding member, a spiral ridge or an abrasive surface. In other embodiments, the abrasive element comprises an abrasive disc, an abrasive surface and/or any other member that is configured to be separated from the tip or that is configured to be permanently attached to the tip. In one embodiment, the tip is removable from the handpiece assembly. In other embodiments, the time-release material comprises a plurality of microcapsules, capsules or other enclosures configured to release their internal contents at various times following delivery to the skin surface. In some embodiments, the time-release material comprises salicylic acid. In other embodiments, the time-release material comprises one or more other active and/or non-active ingredients (e.g., azelaic acid, topical retinoids, benzoyl peroxide, topical antibiotics, other anti-acne materials, saline, other dilutants or fluids, soaps, hardening agents, gels, other binders, lotions, moisturizers, peptides, amino acids, UVA and/or UVB sunblocks, other sunblocking agents, skin tightening agents, hyaluronic acid (HA), other hydration agents, hair removal or hair growth suppression agents, medicaments and pharmaceuticals, etc.), either alone or in combination with one another.

In one embodiment, the time-release material is impregnated along at least a portion of the tip. In other embodiments, the time-release material is initially contained within a cartridge or other container that is in fluid communication with the delivery conduit when the cartridge or other container is secured to the handpiece assembly. In other embodiments, the time release material is delivered to the tip of the handpiece without any prior dilution or premixing. In some embodiments, the handpiece assembly comprises a recess configured to removably receive a cartridge, wherein an internal content of the cartridge is placed in fluid communication with the delivery conduit when the cartridge is secured within the recess of the handpiece assembly. In some embodiments, the cartridge or container comprises a movable piston therein, wherein the movable piston configured to urge an internal content of the cartridge toward an outlet of the cartridge. In some embodiments, the cartridge or container comprises an airless pump design or configuration. In one embodiment, the time-release material is configured to treat a skin disorder or condition (e.g., acne, oily or dry skin, etc.).

According to certain arrangements, a device for treating a skin surface includes a handpiece assembly having a distal end and a proximal end such that the handpiece assembly comprises at least one delivery conduit and at least one waste conduit. The device additionally comprises a tip configured to be positioned along the distal end of the handpiece assembly, such that the tip is adapted to contact the skin surface being treated. According to certain embodiments, the tip comprises a peripheral lip, a first opening in fluid communication with the fluid delivery conduit and a second opening in fluid communication with the waste conduit and an abrasive element or surface positioned along a distal end of the tip, said abrasive element or surface configured to remove skin. In one embodiment, the first opening, the second opening and the abrasive element of the disc are positioned along an interior of the peripheral lip. In another arrangement, one or more waste conduits are configured to be in fluid communication with a vacuum to selectively remove debris away from the tip. In other configurations, a delivery conduit is placed in fluid communication with the waste conduit and the vacuum when the peripheral lip contacts a skin surface. In yet other embodiments, one or more time-release materials are configured to be delivered to the skin surface being treated.

In some embodiments, the handpiece assembly comprises a housing having a clamshell design. In one embodiment, a housing of the handpiece assembly comprises two or more portions that are configured to removably or permanently attach to each other (e.g., using screws, other fasteners, snap fit or friction fit connections, adhesives, welds and/or any other connection method or device). In some embodiments, the two or more portions of the housing are configured to be manufactured using an injection molding procedure or any other molding or manufacturing process (e.g., compression molding, thermoforming, extrusion, etc.). In one embodiment, the two portions or more portions of the housing comprise a plastic, metal, alloy and/or any other synthetic or natural material.

According to other embodiments, the device additionally includes a valve configured to control a flowrate of a fluid being delivered through the fluid delivery conduit to the tip. In another arrangement, the abrasive element or structure comprises one or more protruding members, spiral ridges and/or abrasive surfaces. In certain embodiments, the time-release material comprises a plurality of microcapsules or capsules configured to release their internal contents at various times following delivery to the skin surface. In one embodiment, the time-release materials comprise one or more of the following: peptides, amino acids, UVA and/or UVB sunblocks, other sunblocking agents, skin tightening agents, hyaluronic acid (HA), other hydration agents, hair removal or hair growth suppression agents, medicaments and pharmaceuticals, combinations thereof and/or any other substance. In other arrangements, time-release materials are impregnated along at least a portion of the tip. In yet other embodiments, the cartridge or other container is in fluid communication with the handpiece assembly. In certain embodiments, the time-release materials are configured to be released to the skin surface after contact with water or another dilutant. In other arrangements, the time-release materials are configured to treat acne or another skin disorder.

According to certain embodiments of the present application, a handpiece assembly for treating a skin surface comprises a recess configured to receive a cartridge or other container. The cartridge or other container comprises one or more treatment materials, such as, for example, human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, acids, anesthetics, medicants, other non-active or active compounds, other fluids or materials, combination or mixtures thereof and/or any other substance. In one embodiment, the handpiece assembly comprises a valve or other flow control device or feature to enable a user to selectively regulate a flowrate of a treatment material through the handpiece assembly. In other embodiments, the cartridge or other container comprises an inlet configured to be in fluid communication with water, saline, another dilutant or dissolvent or another fluid. The water, saline, another dilutant or dissolvent or another fluid is configured to be delivered through the inlet and to an interior of the cartridge so as to mix or combine with a treatment material contained therein. In some embodiments, the treatment material contained within the cartridge or container is a liquid, solid, gel, granulated material or concentrated solution. In some embodiments, one or more treatment fluids are conveyed from an outlet of the cartridge or container to a tip attached to a distal end of the handpiece assembly.

According to certain arrangements, treatment materials that are provided to the skin interface during a dermabrasion procedure are configured to be released or otherwise made available to a user's skin over a pre-selected, relatively extended time period. Such time release materials can be provided in the form of microcapsules, other capsules or enclosures and/or the like.

Regardless of the form in which they are provided (e.g., within microcapsules or other enclosures), time-release products or materials can be delivered to a skin surface directly through a cartridge or other container. Such a cartridge can be positioned within a handpiece assembly, such as, for example, those illustrated in FIGS. 1-4F, 13A-16B and 18B herein. Cartridges or other containers containing such time-release materials can be provided in various locations of a handpiece assembly, including, without limitation, a recess of the main portion, underneath or near a removable tip and/or the like. In certain embodiments, a cartridge or other container containing one or more time-release materials is separate from the handpiece assembly.

For example, as illustrated in FIG. 18A, such a cartridge or other container can be placed along a delivery line, which selectively supplies fluids and/or other materials through the cartridge to a handpiece assembly. In other arrangements, such as, for example, those illustrated in FIGS. 6B, 7, 17 and 20A-23B herein, time-release materials can be provided to the handpiece assembly from one or more upstream containers or other sources via a delivery line. By way of example, in accordance with the configuration depicted herein in FIGS. 7 and 17, time-release and/or other products and substances can be placed within one or more containers of a manifold system. Such materials can be subsequently delivered through a handpiece assembly using one or more conduits to the skin area being treated.

In yet other arrangements, time-release materials are advantageously provided, either alone or in combination with one or more other substances, within a recess, cavity or other opening or a tip or other portion of a skin treatment system. For example, such recesses can be provided along a distal surface of the tip, as illustrated in FIGS. 12A-12C and discussed in greater detail herein. In certain embodiments, one or more time-release materials are embedded, impregnated, placed, stored and/or otherwise disposed on one or more surfaces or areas of the tip or other portion or component of the skin treatment system (e.g., the foam pads of FIG. 19A-20B). Such time-release materials, which may be provided alone or in combination with any other materials, can comprise microcapsules, other capsules, solids, semisolids, other dried substances, gels, concentrated solutions and/or the like. In some arrangements, time-release materials and/or other substances are provided in capsules (e.g., microcapsules), caps, loose form (e.g., positioned on or within a recess, other portion of the tip, within a cartridge or other container, adhered to one or more surfaces, etc.), as a tablet, pill, disc or other dissolvable solid, saturated within a foam pad or other sponge-like material and/or the like.

Regardless of where the time-release materials are positioned relative to the handpiece assembly (e.g., within a cartridge or other container, within or outside of a handpiece assembly, in a recess or other opening of a tip or other portion of a handpiece assembly, within a foam pad, on a surface of a tip or other portion of a handpiece assembly, etc.), water (e.g., distilled, tap water, filtered, etc.), saline, other dilutants and/or other fluids can be used to selectively dissolve, liquefy, melt, soften, dilute or otherwise prepare the time-release and/or any other materials. Accordingly, the desired salicylic acid, other anti-acne materials, human growth factors, cytokines, soluble collagen, antioxidants, matrix proteins, serums, water, saline, other dilutants or dissolvents, vitamins, chemical exfoliation agents, lotions, soothing agents, brightening or lightening agents, peptides, amino acids, other acids, anesthetics, UVA and/or UVB sunblocks, other sunblocking agents, skin tightening agents, hyaluronic acid (HA), other hydration agents, hair removal or hair growth suppression agents, medicaments and pharmaceuticals, other non-active or active compounds, other fluids or materials, combination or mixtures thereof and/or any other substance can be advantageously provided to the skin surface being treated, as desired or required.

According to certain embodiments, time-release materials include one or more active ingredients that target specific skin conditions or types. For instance, a time-release product used to help control skin acne can include salicylic acid. The salicylic acid can be provided alone or in combination with one or more other active and/or non-active ingredients (e.g., azelaic acid, topical retinoids, benzoyl peroxide, topical antibiotics, other anti-acne materials, saline, other dilutants or fluids, soaps, hardening agents, gels, other binders, lotions, moisturizers, peptides, amino acids, UVA and/or UVB sunblocks, other sunblocking agents, skin tightening agents, hyaluronic acid (HA), other hydration agents, hair removal or hair growth suppression agents, medicaments and pharmaceuticals, etc.).

Time-release salicylic acid capsules (e.g., microcapsules) and/or any other active or non-active ingredients included in a skin treatment material can be encapsulated within a solid binder, such as, for example, soap or gel. Thus, when water or another fluid is added to the material, the treatment material can at least partially dissolve, advantageously releasing capsules onto the skin surface. The capsules can be configured to release their internal contents at different time intervals after being deposited on or near a person's skin.

Alternatively, as discussed in greater detail herein, such microcapsules or other time-release materials can be provided within a cartridge, another container, a recess or other opening and/or the like. According to certain embodiments, the microcapsules or other time-release materials are included within a binder or are provided in loose form (e.g., as a solid, within a liquid, gel, other fluid or other medium, etc.). Thus, time-release materials can be selectively delivered to the skin (or be initially present at a tip-skin interface) in one or more different forms. Regardless of the exact manner in which they are provided to a person's skin, such time-release materials can help target certain skin ailments or conditions (e.g., acne, eczema, psoriasis, etc.), conditions (e.g., dry skin, oily skin, etc.) and/or the like.

In some embodiments, microcapsules and/or other time-release products delivered to the skin surface are configured to be released or otherwise become available to the skin at different times from each other. For example, microcapsules can be adapted to release salicylic acid and/or any other active or non-active ingredients contained therein in various time intervals (e.g., quarter-hour, half-hour, one-hour, two-hour, three-hour, etc.). Accordingly, the desired materials can be provided to a target skin surface to have an effect on such a surface over a longer period of time. This can facilitate a particular treatment procedure by effectively prolonging the overall treatment time-period. For example, in some embodiments, an acne treatment is more effective if salicylic acid is released over a targeted skin surface during a longer time period (e.g., less than 30 minutes, 1 hour, 2 hours, 4 hours, 6 hours, 8 hours, 10 hours, 12 hours, 24 hours, 36 hours, 48 hours, more than 48 hours, etc.).

In one embodiment, time-release materials are provided to a dermabrasion system which is adapted to treat skin having acne or another skin condition. A handpiece assembly having an abrasive distal end, such as, for example, a tip in accordance with any of the arrangements illustrated or otherwise disclosed herein, or equivalents thereof, can be used to treat a skin surface of a patient. As the tip is moved across the target skin area, exfoliated skin, infected waste and/or other materials can be advantageously removed. In addition, the treatment system can be configured to selectively deposit time-release product onto the treated skin before, after and/or contemporaneously with the exfoliation process. As discussed in greater detail herein, the time-release product can be delivered from a cartridge or other container located either within a handpiece assembly or separate from it. In some arrangements, water, saline and/or other dilutants are required to at least partially dissolve or otherwise release such substances (e.g., from a binder, gel, solid, etc.). Salicylic acid and/or any other materials contained within the time-release product (e.g., microcapsules, other capsules, caps, etc.) and/or other materials delivered to the patient's skin can be advantageously released over a longer time-period so as to help prevent or reduce the likelihood of bacterial infection, pain or discomfort, sensitivity to sunlight or other light sources and/or the like.

According to certain arrangements, time-release capsules or other materials containing salicylic acid and/or other skin solutions can be embedded on or near a surface of a tip using a binder. For example, glycerin soap or other base materials or hardening agents can be used to bind the time-release materials. As water, saline or other dilutants or fluids are selectively delivered to the bound materials, time-release materials can dissolve, allowing salicylic acid capsules to be released to a target area of the skin. In one configuration, the time-release materials comprise approximately 30% of the bound mixture by volume, while the soap or other base material and/or hardening agent comprises the remaining approximately 70%. In other embodiments, the volumetric ratio of time-release materials to base materials and hardening agents can be greater or less than 3:7, as required or desired (e.g., less than approximately 1:9, approximately 1:4, 2:3, 1:1, 3:2, 7:3, 4:1, more than approximately 4:1, etc.).

According to certain arrangements, a disc, plate or other member having diamonds or any other abrasive element is removably positioned within an interior region of the tip (e.g., generally between the tip and adjustable distal portion or any other component of the handpiece assembly). Such a disc, which is configured to contact and abrade skin through one or more openings of the tip, can be conveniently removed for cleaning, replacement and/or any other purpose.

According to other embodiments, a treatment material disposed on or near the tip of the handpiece assembly is configured to be mixed or combined with water, saline or another fluid being delivered through the handpiece assembly to create a treatment fluid. In certain embodiments, the treatment material is provided as a solid, semi-solid, gel, granulated material or concentrated fluid or solution. In some arrangements, the treatment material is positioned within a recess of the tip, between the tip and a main body portion of the handpiece assembly or within the main body portion of the handpiece assembly. In some embodiments, water, saline, treatment fluid or other fluid being conveyed through the handpiece assembly is configured to be heated.

According to certain embodiments of the present application, a device for treating a skin surface comprises a handpiece assembly having a distal end and a proximal end. The handpiece assembly comprises at least one delivery conduit and at least one waste conduit. The handpiece assembly further comprising a recess or other opening configured to receive a cartridge or other container having an interior cavity. In one embodiment, the interior cavity of the cartridge is placed in fluid communication with the fluid delivery conduit when the cartridge is secured within the recess. The device additionally includes a tip positioned along the distal end of the handpiece assembly, such that the tip is configured to contact the skin surface. In certain embodiments, the tip comprises a peripheral lip, a first opening in fluid communication with the fluid delivery conduit and a second opening in fluid communication with the waste conduit and an abrasive element. The first opening, the second opening and the abrasive element are generally positioned along an interior of the peripheral lip. In one embodiment, the waste conduit is configured to be in fluid communication with a vacuum to selectively remove debris away from the tip. In other arrangements, the delivery conduit is placed in fluid communication with the waste conduit and the vacuum when the peripheral lip contacts a skin surface.

In certain arrangements, the device further includes a valve generally positioned between the interior cavity of the cartridge and the fluid delivery conduit. The valve can be adapted to control the flowrate of a fluid being conveyed from the interior cavity of the cartridge to the tip. In other embodiments, the handpiece assembly comprises an adjustable intermediate space positioned generally between the interior cavity of the cartridge and the fluid delivery conduit. In one arrangement, a volume of the adjustable intermediate space can be selectively modified by moving an actuator on the handpiece assembly. In other configurations, the handpiece assembly comprises a stem in fluid communication with the fluid delivery conduit. The stem can be adapted to extend into the interior cavity of a cartridge when the cartridge is positioned with the recess of the handpiece assembly. In other embodiments, the tip is selectively removable from the handpiece assembly. In one arrangement, the abrasive element comprises a plurality of posts, other protruding members, a spiral-shaped ridge, an abrasive surface, a foam pad, another type of pad and/or the like. In some arrangements, the device further includes a heating element configured to selectively heat a fluid being conveyed through the delivery conduit, another interior passage or conduit of the handpiece assembly, the tip, an inlet line and/or the like. In other embodiments, the cartridge comprises an inlet configured to be placed in fluid communication with a delivery source.

According to other arrangements, a skin treatment system includes a handpiece assembly having a distal end and a proximal end. The handpiece assembly comprises a fluid delivery conduit. In one embodiment, the handpiece assembly comprises a first portion and a second portion, with the first portion being selectively movable relative to the second portion. The skin treatment system further includes a tip adapted to contact skin and positioned on the distal end of the handpiece assembly. In one embodiment, the tip comprises a first opening, which is in fluid communication with the fluid delivery conduit, and an abrasive element. The system further comprises an intermediate space generally defined between the first and second portions of the handpiece assembly. Movement of the first portion with respect to the second portion can modify the volume of the intermediate space and generally control the flowrate of a fluid being conveyed through the fluid delivery conduit. In some embodiments, the system further includes an actuator on the handpiece assembly for moving the first portion relative to the second portion.

According to other embodiments, movement of the first portion with respect to the second portion is produced by rotating the second portion relative to the first portion. In some arrangements, the tip is selectively removable from the second portion. In another adaptation, the tip comprises a plurality of posts or protruding members configured to treat skin. In other arrangements, the tip comprises one or more ridges (e.g., spiral-shaped ridges), abrasive surfaces or elements and/or other features or components configured to treat skin. In certain embodiments, the handpiece assembly further comprises a waste channel in fluid communication with a second opening in the tip. In another embodiment, the handpiece assembly includes a recessed area configured to receive a cartridge comprising at least one treatment fluid or material. In other arrangements, the cartridge includes an interior portion which is at least partially defined by a membrane. The membrane can be configured to be pierced by a hollow spike of the first portion of the handpiece assembly when the cartridge is properly inserted within the recessed area, so that the hollow spike is placed in fluid communication with the delivery channel. In certain configurations, the interior portion of the cartridge comprises human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, acids, anesthetics, medicants, other non-active or active compounds, other fluids or materials, combination or mixtures thereof and/or any other substance. In other arrangements, the device comprises a heater configured to selectively heat a fluid being conveyed through the fluid delivery conduit toward the tip.

According to certain embodiments, a method of providing a treatment fluid to a skin surface while treating said skin surface with a handpiece device includes providing at least one treatment material on or within a handpiece device. In one arrangement, a tip is configured to be removably positioned along a distal end of a main body portion of the handpiece assembly. The tip can be adapted to abrade or otherwise treat skin when moved relative to a skin surface. The treatment method additionally includes directing a first fluid through a delivery passage of the handpiece assembly so that said delivery passage generally contacts at least one treatment material of the tip. In some arrangements, the treatment material is configured to at least partially dissolve, dilute or combine with the first fluid so as to create a desired treatment fluid. Further, the treatment fluid can be configured to be provided to the tip and to the skin surface being treated while a distal end of the tip is being translated over said skin surface.

In some arrangements, the treatment material comprises a solid, granular material, gel or concentrated solution and/or any other material. In other embodiments, the first fluid comprises water (e.g., sterile, tap, distilled, filtered, etc.), saline, other dilutants or dissolvents and/or any other fluid. In other arrangements, the treatment fluid comprises human growth factors, cytokines, soluble collagen, antioxidants or matrix proteins. In another embodiment, the treatment material is positioned in or near the tip, such as, for example, within a post, other protruding member, other recess, underneath the tip and/or like. In other arrangements, the treatment material comprises a disc, tablet, capsule, granular material, gel and/or the like. In one embodiment, the treatment material is configured to be positioned within a cage or other porous container. In other arrangements, the disc, table, capsule or other treatment material is configured to be secured generally between the main body portion and the tip of the handpiece assembly. In one configuration, the method further includes regulating a flowrate of the first fluid by selectively controlling a valve on the handpiece assembly. In another arrangement, the method additionally includes selectively heating the first fluid using a heating member positioned in thermal communication with the delivery passage of the handpiece assembly. In some embodiments, the treatment material is positioned within a cartridge which is configured to be removably secured to a receiving area of the handpiece assembly.

According to some embodiments disclosed in the present application, a device for treating the skin comprises a handpiece assembly having a distal end and a proximal end, a cartridge comprising an interior cavity and a tip on the distal end of the handpiece assembly. The handpiece assembly includes a fluid delivery conduit and a waste conduit. In addition, the cartridge is coupled to the handpiece assembly, with the interior cavity of the cartridge being in fluid communication with the fluid delivery conduit. Further, the tip is configured to contact the skin. The tip comprises a peripheral lip, a first opening in fluid communication with the fluid delivery conduit, a second opening in fluid communication with the waste conduit and an abrasive element. The first opening, the second opening and the abrasive element of the tip are generally positioned within the peripheral lip.

In some embodiments, the device further comprises a valve positioned between the interior cavity of the cartridge and the fluid delivery conduit. In one embodiment, the handpiece assembly comprises an adjustable intermediate space positioned generally between the interior cavity of the cartridge and the fluid delivery conduit. In another arrangement, a volume of the adjustable intermediate space can be selectively modified by moving an actuator on the handpiece assembly. In other embodiments, the handpiece assembly comprises a recessed area configured to receive the cartridge.

According to other embodiments, the handpiece assembly comprises a stem that is in fluid communication with the fluid delivery conduit as the stem is configured to extend into the interior cavity of a cartridge when the cartridge is coupled to the handpiece assembly. In another embodiment, the tip is selectively removable from the handpiece assembly. In some arrangements, the abrasive element comprises a plurality of protruding members. In other embodiments, the tip comprises an abrasive edge.

According to another embodiment, a system for treating the skin comprises a handpiece assembly having a distal end and a proximal end and a tip on the distal end of the handpiece assembly configured to contact the skin. The handpiece assembly includes a fluid delivery conduit and first and second portions. Further, the tip includes a first opening in fluid communication with the fluid delivery conduit and an abrasive element. An intermediate space generally defined between the first and second portions of the handpiece assembly is in fluid communication with the fluid delivery conduit. In one embodiment, movement of the first portion with respect to the second portion modifies the volume of the intermediate space to control a flowrate through the fluid delivery conduit. The system further comprises an actuator on the handpiece assembly for actuating movement between the first portion and the second portion.

In some embodiments, movement of the first portion with respect to the second portion is produced by rotating the second portion relative to the first portion. In other embodiments, the tip is selectively removable from the second portion. In still other arrangements, the tip comprises a plurality of protruding members configured to treat skin. In another embodiment, the tip comprises an abrasive surface configured to treat skin.

According to some embodiments, the handpiece assembly further comprises a waste channel in fluid communication with a second opening in the tip. In another arrangement, the handpiece assembly includes a recessed area configured to receive a cartridge comprising at least one treatment fluid or material. In other embodiments, the cartridge includes an interior portion at least partially defined by a membrane. The membrane is configured to be pierced by a hollow spike of the first portion of the handpiece assembly. Further, the hollow spike is in fluid communication with the delivery channel. In one embodiment, the interior portion of the cartridge comprises human growth factors, cytokines, soluble collagen, antioxidants and/or matrix proteins.

According to other embodiments, the present application discloses a method for treating the skin of a patient with a skin treatment device having a working end that includes an abrading structure configured to engage and abrade skin. The method includes placing the working end of the skin treatment device against the skin of the patient, translating the working end over the skin to abrade a skin surface, providing a treatment fluid to the skin through an opening in the working end and aspirating skin debris from the skin surface through an aspiration opening in the working end of the skin treatment device. In some embodiments, the treatment fluid comprises human growth factors, cytokines, soluble collagen, antioxidants and/or matrix proteins.

According to some embodiments disclosed in the present application, a device for treating the skin comprises a handpiece assembly having a distal end and a proximal end. The handpiece assembly includes a fluid delivery conduit and a waste conduit. In addition, the handpiece assembly is adapted to receive a cartridge having an interior cavity. Further, the device includes a tip attached to the distal end of the handpiece assembly and comprising a surface configured to treat skin. The waste conduit is configured to be in fluid communication with a vacuum source and the fluid delivery conduit is configured to be in fluid communication with an interior cavity of a cartridge when a cartridge is secured to the handpiece assembly.

In some embodiments, the handpiece assembly comprises a flow control feature configured to selectively regulate a flowrate through the fluid delivery conduit. In another arrangement, the handpiece assembly includes a main body portion and an adjustable portion attached to the main body portion. The flow control feature can comprise an adjustable intermediate space generally located between the main body portion and the adjustable portion. In other embodiments, a volume of the adjustable intermediate space can be selectively modified by moving the main body portion relative to the adjustable portion of the handpiece assembly.

In one embodiment, the handpiece assembly comprises a recessed area configured to secure a cartridge. In another arrangement, the handpiece assembly comprises a stem adapted to access an interior cavity of a cartridge when a cartridge is secured to the handpiece assembly. According to some embodiments, the tip is selectively removable from the handpiece assembly. In other embodiments, the tip comprises a plurality of protruding members configured to treat skin. In still other arrangements, the tip comprises an abrasive surface configured to treat skin.

According to another embodiment, a system for treating the skin includes a handpiece assembly. The handpiece assembly comprises a tip configured to treat skin, a first portion and a second portion. The first portion includes a delivery conduit, which has a first longitudinal axis, and is configured to be in fluid communication with at least one fluid source. Further, the second portion includes a distal end and a proximal end, with the proximal end being attached to the main body portion and the distal end being attached to the tip. The second portion includes a delivery channel having a second longitudinal axis and being in fluid communication with the tip and the delivery conduit. In addition, the second portion further comprises a removal channel being in fluid communication with the tip and a suction source. In some embodiments, an intermediate space is generally defined between the first and second portions of the handpiece assembly. Such an intermediate space is in fluid communication with the delivery conduit of the first portion and the delivery channel of the second portion. Further, a volume of the intermediate space is configured to be adjusted by selectively modifying a separation distance between the first portion and the second portion. Accordingly, a flowrate from a fluid source to the tip can be selectively controlled by modifying the separation distance between the first portion and the second portion.

In some embodiments, the separation distance between the first portion and the second portion is modified by rotating the second portion relative to the first portion. In other arrangements, the first longitudinal axis of the delivery conduit is generally offset with the second longitudinal axis of the delivery channel. In one embodiment, the tip is selectively removable from the second portion.

According to some embodiments, the tip comprises a plurality of protruding members configured to treat skin. In other embodiments, the tip comprises an abrasive surface configured to treat skin. In one embodiment, the first portion further comprises a waste channel in fluid communication with the removal channel of the second portion. In another arrangement, the first portion includes a recessed area configured to receive a cartridge comprising at least one treatment fluid or material. In some embodiments, the cartridge includes an interior portion at least partially defined by a membrane which is configured to be pierced by a hollow spike of the first portion of the handpiece assembly. The hollow spike is in fluid communication with the delivery channel. According to other embodiments, the cartridge the interior portion of the cartridge comprises human growth factors, cytokines, soluble collagen, antioxidants or matrix proteins.

According to other embodiments disclosed in the present application, a method of treating the skin comprises providing a handpiece assembly comprising a body and a tip having a distal end. The handpiece assembly includes a delivery conduit and a waste conduit that are in fluid communication with the distal end of the tip. The method further includes placing the delivery conduit of the handpiece assembly in fluid communication with a fluid source for providing at least one treatment fluid to the distal end of the tip and placing the waste conduit of the handpiece assembly in fluid communication with a suction source for removing waste materials from the distal end of the tip. In addition, the method comprises moving the handpiece assembly along a person's skin and activating the suction source to remove a volume of waste materials from the distal end of the tip and to simultaneously deliver a volume of the treatment fluid to the distal end of the tip. In one embodiment, the flowrate at which treatment fluids and/or other materials are delivered to the tip can be varied by a valve or other flow control feature of the handpiece assembly. In some embodiments, the treatment fluid comprises human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents (e.g., kojic acid), peptides, acids, anesthetics, medicants, other non-active or active compounds, other fluids or materials, combination or mixtures thereof and/or any other substance.

According to some embodiments disclosed in the present application, a device for treating the skin comprises a handpiece assembly having a distal end and a proximal end. The handpiece assembly further comprises a main body portion and a tip on the distal end of the main body portion.

In some embodiments, the handpiece assembly includes one or more fluid delivery conduits, one or more waste conduits and/or one or more energy conduits. In some embodiments, the handpiece assembly comprises a cartridge comprising an inner cavity. In addition, the cartridge is coupled to the handpiece assembly with the inner cavity of the cartridge being in fluid communication with the fluid delivery conduit. In some embodiments, the main body portion comprises an interior volume in which one or more of the conduits can be located. Further, the tip is configured to contact the skin.

In some embodiments, the tip is configured to be removable from the main body portion. In some embodiments, the main body portion and tip are a single unitary piece. The tip comprises a plurality of needles, a base member, and a peripheral lip, ridge, outer peripheral member or the like and. The tip can also comprise one or more openings in fluid communication with a waste conduit, one or more openings in communication with a fluid delivery conduit and/or one or more energy contact points in electrical communication with an energy source. In some embodiments the tip comprises one or more hollow needles, the hollow needles in fluid communication with a fluid delivery conduit. In some embodiments, one or more of the needles in the tip is in electrical communication with an energy conduit. In some embodiments, the handpiece assembly includes a source of pressure (e.g. pneumatic pressure) configured to move the plurality of needles and/or the base member with respect to the peripheral lip of the tip.

According to some embodiments disclosed in the present application, a method of treating the skin includes providing a handpiece assembly comprising a body and a tip having a distal end. The handpiece assembly includes a waste conduit and a fluid delivery conduit that are in fluid communication with the distal end of the tip. The tip comprises a peripheral lip and a plurality of needles. The method further includes placing the delivery conduit of the handpiece assembly in fluid communication with a fluid source for delivering at least one treatment fluid to the distal end of the tip and placing the waste conduit of the handpiece assembly in fluid communication with a suction source for removing waste materials from the distal end of the tip. In addition, the method comprises placing the peripheral lip the tip in contact with a person's skin. The method further comprises activating the suction source and causing the plurality of needles to penetrate the person's skin. The method also comprises delivering a treatment fluid to the distal end of the tip. In some embodiments, the treatment fluid comprises human growth factors, cytokines, soluble collagen, antioxidants, matrix proteins, serums, water, saline and/or any other fluids or materials, either alone or in combination.

According to other embodiments disclosed in the present application, a method of treating the skin comprises providing a handpiece assembly comprising a body and a tip having a distal end. The tip comprises a peripheral lip and a plurality of hollow needles. The handpiece assembly includes a waste conduit in fluid communication with the distal end of the tip and a delivery conduit in communication with the plurality of hollow needles. In addition, the method comprises placing the peripheral lip of the tip in contact with a person's skin. The method further comprises activating the suction source and causing the plurality of needles to penetrate the person's skin. The method also comprises delivering a treatment fluid to the plurality of hollow needles. In some embodiments, the treatment fluid comprises human growth factors, cytokines, soluble collagen, antioxidants, matrix proteins, serums, water, saline, dermal fillers, hot or cold vapors and/or gases and/or any other fluids or materials, either alone or in combination.

According to other embodiments disclosed in the present application, a method of treating the skin comprises providing a handpiece assembly comprising a body and a tip having a distal end. The tip comprises a peripheral lip and a plurality of needles. The handpiece assembly includes a waste conduit in fluid communication with the distal end of the tip and an energy conduit in communication with the plurality of needles. In addition, the method comprises placing the peripheral lip the tip in contact with a person's skin. The method further comprises activating the suction source and causing the plurality of needles to penetrate the person's skin. The method also comprises delivering energy to the plurality of needles, thus causing damage to the skin. In some embodiments, the energy source comprises radio frequency (e.g. RF energy), ultrasound, and/or microwave energy.

According to the embodiments disclosed in the present application, a method of treating the skin can further include using pneumatic or other appropriate force to move the plurality of needles and/or the base member with respect to the peripheral lip of the tip. The plurality of needles and/or the base member can be moved in this manner to a predetermined depth in the patient's skin. According to the embodiments disclosed in the present application, the methods of using needles to treat the skin as described above can be utilized in conjunction with other microdermabrasion treatments. The use of needles could occur before, during, after or in lieu of other microdermabrasion treatments.

The methods summarized above and set forth in further detail below describe certain actions taken by a user (e.g., a professional in some instances); however, it should be understood that they can also include the instruction of those actions by another party. Thus, actions such as "moving a handpiece" or "delivering a fluid" include "instructing moving a handpiece" and "instructing delivering a fluid."

BRIEF DESCRIPTION OF THE DRAWINGS

These and other features, aspects and advantages of the present application are described with reference to drawings of certain embodiments, which are intended to illustrate, but not to limit, the present inventions. It is to be understood that these drawings are for the purpose of illustrating the various concepts disclosed herein and may not be to scale.

FIGS. 5A-5C illustrate various views of the handpiece assembly of FIG. 4;

DETAILED DESCRIPTION

Although the various embodiments of a handpiece assembly have specific relevance to a skin treatment system, the features, advantages and other characteristics disclosed herein may have direct or indirect applicability in other applications, such as, for example, medical devices, mechanical devices and/or the like.

Figure 1:
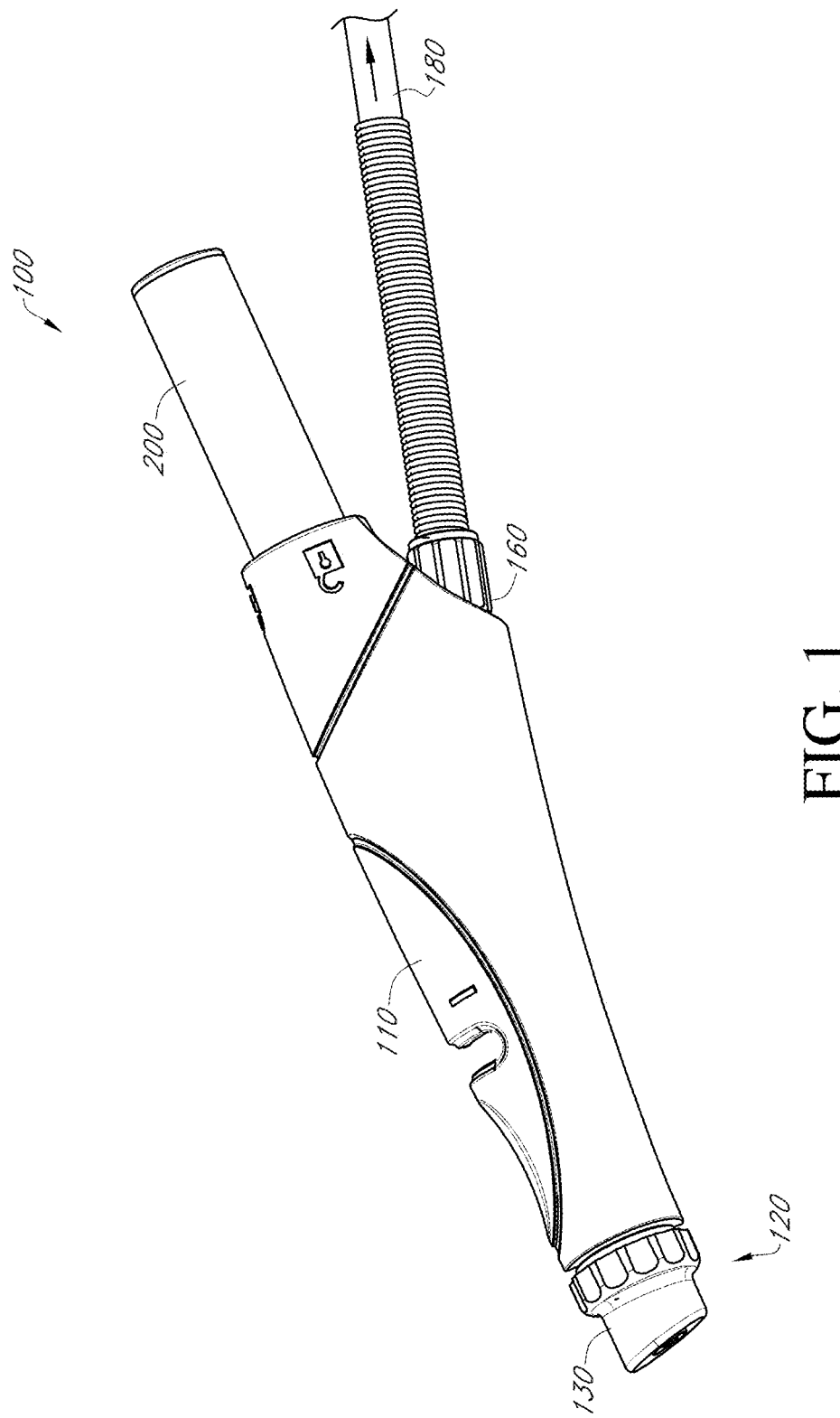
FIG. 1 illustrates a perspective view of a handpiece assembly configured for use with a skin treatment system according to one embodiment.

FIG. 1 illustrates one embodiment of a handpiece assembly 100 configured for use with a skin treatment system. As shown in FIG. 1, a handpiece assembly 100 can include a main body portion 110 configured to receive a tip 130 along its distal end 120. In some embodiments, the tip 130 is removably attached to the distal end of the main body portion 110. Alternatively, however, the tip can be permanently attached to the main body portion 110, as desired or required. The tip can include one or more abrasive features, surfaces and/or the like that are configured to selectively abrade skin when the handpiece assembly 100 is moved relative to a subject's skin. Therefore, the tip can be configured to conduct the microdermabrasion of the targeted skin surface. Additional details regarding possible tip options that can be incorporated into any of the embodiments disclosed herein are provided in U.S. patent application Ser. No. 11/392,348, filed on Mar. 29, 2006 and issued as U.S. Pat. No. 8,048,089 on Nov. 1, 2011, the entirety of which is incorporated by reference herein and made a part of the present application.

Figure 2:
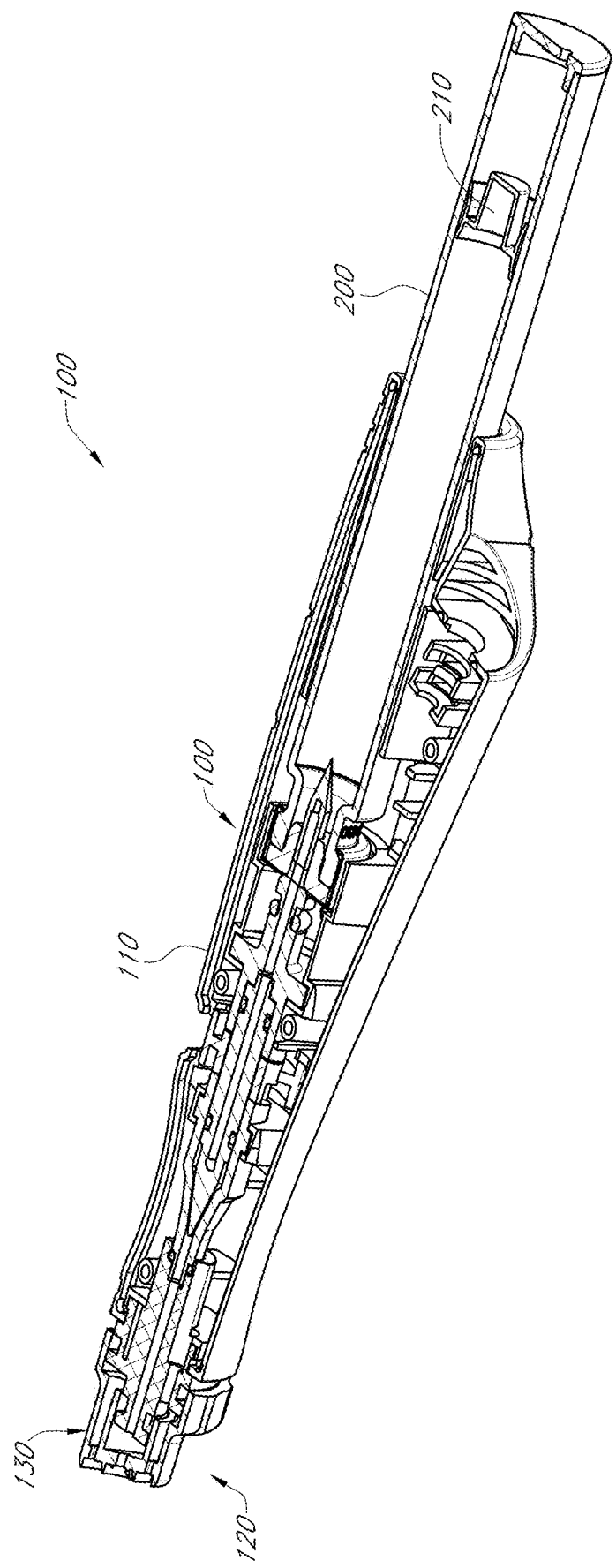
FIG. 2 illustrates a cross-sectional view of the handpiece assembly of FIG. 1.

With continued reference to FIGS. 1 and 2, the handpiece assembly 100 can be sized, shaped and otherwise configured to receive one or more vials or cartridges 200. For example, as shown, the handpiece assembly can include a recess or other opening into which a vial 200 can be placed and secured. Such vials or other containers 200 can include one or more fluids and/or other materials that can be selectively delivered to the subject's skin surface during use.

In some embodiments, the vial or cartridge 200 comprises one or more of the following: skin tightening agents, platelet-rich plasma (PRP), exfoliation agents, peptides, bleaching agents, anti-acne agents, human growth factors, cytokines, soluble collagen, antioxidants, matrix proteins, serums, salicylic acid, other anti-acne acids and materials, microcapsules, capsules, other time-release products and substances (e.g., capsules, microcapsules, etc.), water (e.g., distilled, tap water, filtered, etc.), saline, other dilutants or dissolvents, vitamins, chemical exfoliation agents, lotions, soothing agents, brightening or lightening agents (e.g., kojic acid), numbing agents, peptides, acids, anesthetics (e.g., Lidocaine), medicants, other non-active or active compounds, other fluids or materials, combination or mixtures thereof and/or any other substance. Such materials contained in the vial 200 can be selectively delivered to a user's skin while the handpiece assembly 100 is being used. In some embodiments, the handpiece assembly 100 includes an adjustable valve or other flow control feature to enable a user to regulate the rate of delivery of such fluids or other materials to the treatment surface.

In some embodiments, one or more materials can be strategically embedded, impregnated, placed, stored and/or otherwise disposed on one or more surfaces or areas of the tip or other portion or component of the skin treatment system. Such materials can comprise solids, semi-solids, other dried substances, gels, concentrated solutions and/or the like. For example, such materials can be provided in loose form (e.g., positioned on or within a recess, other portion of the tip, within a cartridge or other container, adhered to one or more surfaces, etc.), as a tablet, capsule, pill, disc or other dissolvable solid, saturated within a foam pad or other sponge-like material and/or the like. Thus, in certain arrangements, water (e.g., distilled, tap water, filtered, etc.), saline, other dilutants and/or other fluids which are delivered to the tip can selectively dissolve, liquefy, melt, soften, dilute or otherwise prepare the materials embedded, impregnated and/or otherwise positioned on the tip, within a cartridge or other container and/or on or within another portion or component of a skin treatment system (e.g., handpiece assembly, fluid line upstream of the handpiece assembly, etc.). Accordingly, the desired human growth factors, cytokines, soluble collagen, antioxidants, matrix proteins, serums, salicylic acid, other anti-acne acids and materials, microcapsules, capsules, other time-release products and substances, peptides, amino acids, UVA and/or UVB sunblocks, other sunblocking agents, skin tightening agents, hyaluronic acid (HA), other hydration agents, hair removal or hair growth suppression agents, medicaments and pharmaceuticals, water, saline, other dilutants or dissolvents, vitamins, chemical exfoliation agents, lotions, soothing agents, skin brightening or lightening agents, other acids, anesthetics, medicants, other non-active or active compounds, other fluids or materials, combination or mixtures thereof and/or any other substance can be advantageously provided to the skin surface being treated, as desired or required.

In addition, as illustrated in FIG. 1, the handpiece assembly 100 can be connected to a vacuum. For example, the waste conduit 180 of the handpiece assembly can be placed in fluid communication with a suction or vacuum source (not shown) in order to remove exfoliated skin, spent fluids, waste materials and/or other substances away from the treatment surface. As noted above, the handpiece assembly 100 can be configured to receive one or more removable tips 130, which may be selected based upon the specific procedure being performed, the desired result and/or any other considerations. The distal portion 120 of the handpiece assembly 100 can include one or more O-rings 138 or other sealing members to prevent undesirable leaks between the main body portion 110 and the tip 130. Additional details regarding removable tips are provided in U.S. patent application Ser. No. 12/832,663, filed on Jul. 8, 2010 and published as U.S. Publ. No. 2011/0082415 on Apr. 7, 2011, the entirety of which is hereby incorporated by reference herein (see, for example and without limitation, FIGS. 5B and 8A through 16B of the referenced application).

With continued reference to FIGS. 1 and 2, the handpiece assembly 100 can be configured to receive one or more types of vials or cartridges 200. For example, a vial 200 can include, without limitation, a standard or non-standard vial, ampoule or any other container. In some embodiments, serums, salicylic acid, other anti-acne acids and materials, microcapsules, capsules, other time-release products and substances, other fluids and/or other materials contained within the cartridge 200 can be drawn toward the tip 130 using one or more suction sources (e.g., the vacuum source configured to remove waste materials from the tip). In other embodiments, the fluids and/or other materials contained within the cartridge gravity flow toward the tip 130 or are conveyed with the help of a fluid transfer device. The cartridge 200 can be selectively removed from the handpiece assembly 100 when a desired volume or other amount of serum or other material has been delivered to the tip 130.

In other arrangements, two or more different cartridges 200 can be used during a skin treatment procedure. For example, a particular procedure may require the contents (e.g., skin tightening agents, platelet-rich plasma (PRP), exfoliation agents, peptides, bleaching agents, anti-acne agents, human growth factors, serums, salicylic acid, other anti-acne acids and materials, microcapsules, capsules, other time-release products and substances, proteins, brightening or lightening agents, peptides, other fluids or substances, etc.) of two or more different cartridges 200. Thus, a user can load and/or unload a combination of cartridges 200 or other containers within a handpiece assembly 100 during a treatment procedure, either at the same time or sequentially (e.g., one after another).

According to some embodiments, as illustrated in FIG. 2, a vial or cartridge 200 can include an internal piston 210 or other movable member. In some embodiments, the piston 210 can urge the internal contents of the vial 200 (e.g., serum, other treatment fluids or materials, etc.) toward the distal end of the vial. The use of such an airless pump design can eliminate or reduce the likelihood that air or other gases will interfere with the consistent delivery of such fluids and/or other materials to the handpiece assembly. Such an airless pump configuration can be used in any of the embodiments disclosed herein.

In such embodiments, the internal volume of the cartridge or vial containing the fluid and/or other material to be selectively delivered to the handpiece assembly can be reduced as fluid and/or other material is expelled from the cartridge. This can help ensure that the internal portion of the cartridge that contains the serum, other liquid and/or other material to be delivered to the handpiece assembly does not include air or other gases. Thus, the treatment media can be consistently and reliably maintained at the distal end of the cartridge interior (e.g., toward the cartridge outlet) during a treatment procedure, regardless if and how a user tilts or otherwise maneuvers the handpiece assembly.

The vial or cartridge 200 can include a main cylindrical portion and a nozzle portion. In some arrangements, the nozzle portion comprises a septum, membrane or other member that can be pierced, punctured or otherwise compromised to access the interior contents of the vial 200 (e.g., serum, other liquids or materials, etc.). The septum can include one or more flexible, rigid and/or semi-rigid materials, such as, for example, rubber, plastic, paper and/or the like.

In some embodiments, a vial or other fluid container 200 can be sized, shaped and otherwise configured to snugly or generally snugly fit within the main body portion 110 of the handpiece assembly 100. Therefore, in some arrangements, the vial or cartridge 200 is secured to the handpiece assembly 100 by friction or by the generally tight tolerances of the recess of the handpiece assembly.

As noted above, the waste conduit 180 (e.g., flexible tubing, hose, etc.) to which the handpiece assembly 100 connects is in fluid communication with a vacuum or other suction source (e.g., pump, other fluid transfer device, etc.). Thus, exfoliated skin, spent fluids and/or other waste materials can be transported away from the tip 130 to a canister (not shown) or other waste source. The rate of transfer of such waste materials can depend on one or more factors, such as, for example, the setting of the vacuum or suction source, the characteristics (e.g., diameter, length, smoothness, etc.) of the various conduits or channels through which the waste materials are conveyed, the viscosity, density and other fluid properties of the waste materials and/or the like.

As discussed herein, in some embodiments, the flow of serums, other fluids and/or any other materials from a vial or cartridge 200 or other source through the handpiece assembly 100 can be regulated by the user using one or more valves or other flow control devices or features.

In some embodiments, a vacuum in fluid communication with the waste conduit 180 can be configured to remove waste materials from the tip 130 and help deliver serums, other fluids and/or any other materials from the vial or cartridge 200 to the tip 130. When the tip 130 is positioned against the subject's skin, suction created by the vacuum source can be transmitted to one or more fluid channels or conduits of the handpiece assembly 100. Such a suction force created within the corresponding channels or conduits of the handpiece assembly can remain intact as long as the tip 130 is maintained against or substantially against the subject's skin. Consequently, the suction force created by the vacuum source can be transferred to one or more fluid delivery channels of the assembly 100, thereby transferring fluids and/or other materials from the vial or other container toward the tip 130.

In some embodiments, serums, other fluids and/or other materials can be delivered to the tip 130 (e.g., from a cartridge, an external source, etc.) through one or more peripheral or other non-centrally located channels, conduits and/or other lines or fittings. For instance, in the handpiece assembly 100 illustrated in FIGS. 1 and 2, such fluids and/or other materials can be routed through one or more internal channels of the assembly and/or waste conduits of the tip. Thus, in some embodiments, one or more of the channels, connectors and/or other hydraulic components may need to be reconfigured to adequately place the non-centrally located delivery openings of the tip in fluid communication with corresponding delivery lines of the handpiece assembly 100.

Figure 3:
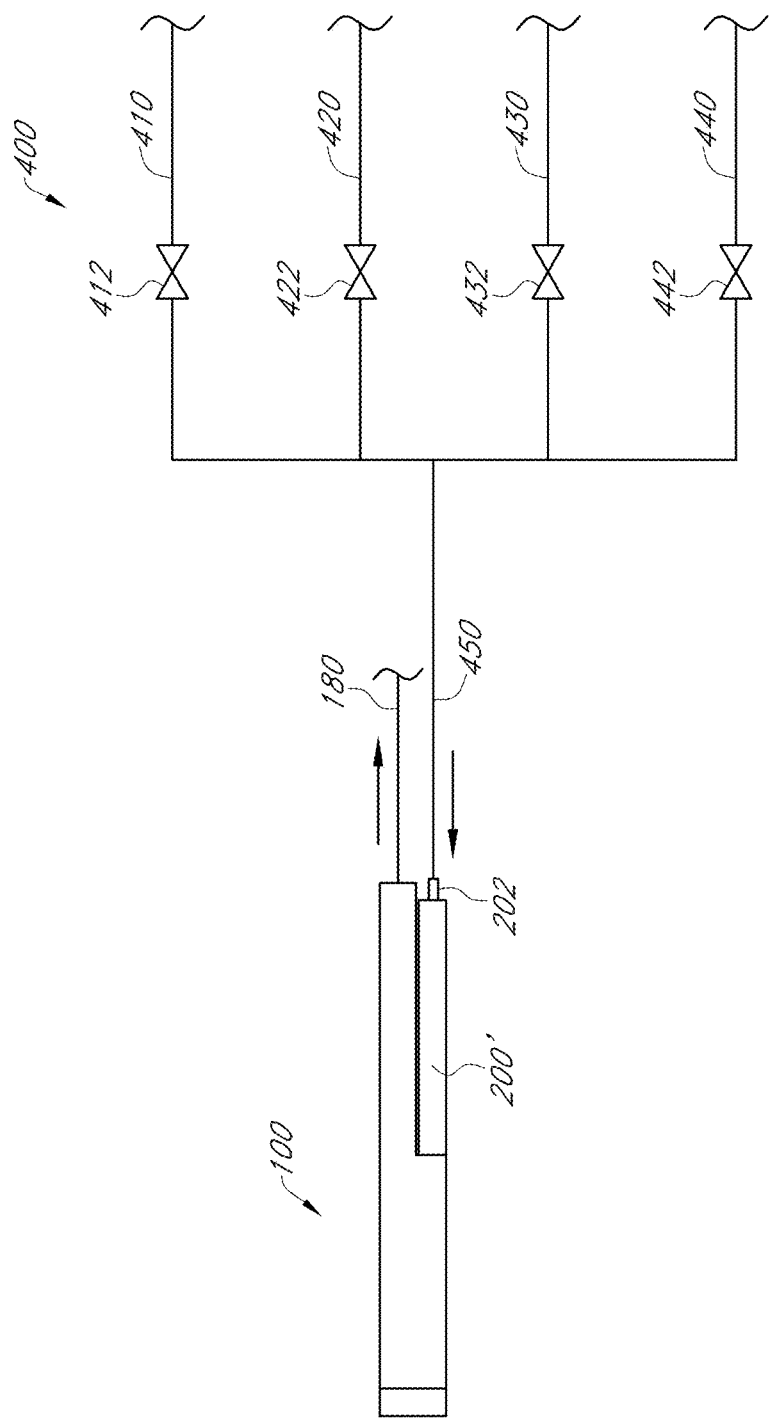
FIG. 3 schematically illustrates a handpiece assembly being in fluid communication with a fluid delivery system or manifold system according to one embodiment.

According to certain embodiments, as illustrated in FIG. 3, a vial, cartridge or other container 200 is placed in fluid communication with a manifold system 400 that may comprise a plurality of individual fluid conduits 410, 420, 430, 440. In turn, one or more of these fluid conduits 410, 420, 430, 440 can be in fluid communication with a separate container (not shown). For example, in some embodiments, such fluid conduits can be in fluid communication with containers of a tower system (see, e.g., FIGS. 9-11). In the illustrated embodiment, the individual fluid lines 410, 420, 430, 440 are in fluid communication with a main fluid conduit 450, which connects to a nozzle 202 along a proximal end of a vial or other container 200 secured within the handpiece assembly 100. One or more of the fluid conduits can comprise a valve 412, 422, 432, 442 or other flow control device or feature to selectively regulate the transfer of fluids and/or other materials to the handpiece assembly 100. In the illustrated arrangement, the manifold system 400 comprises a total of four fluid branches. However, a system can comprise more or fewer fluid branches (e.g., 1, 2, 3, 4, 5, 6, 7, 8, more than 8, etc.), as desired or required by a particular application or use.

According to certain embodiments, one or more of the fluid lines fluid conduits of the manifold system illustrated in FIG. 3 are configured to provide a serum, other treatment fluid and/or the like. Alternatively, however, one or more of the conduits can be configured to receive water (e.g., distilled, tap water, filtered, etc.), saline, other dilutants or dissolvents, other fluids and/or the like to the handpiece assembly 100. As discussed in greater detail herein, such fluids can be adapted to contact and dissolve, dilute, liquefy, soften and/or otherwise mix with one or more solids, gels and/or other materials positioned within or on various surfaces or portions of the handpiece assembly 100 (e.g., tip). This can provide a convenient method of providing one or more materials at the skin-tip interface and/or any other location where such materials are desired or required.

In some embodiments, the vials, cartridges, bottles (e.g., used in towers or other manifold-systems) and/or other fluid sources can include any combination of skin tightening agents, platelet-rich plasma (PRP), exfoliation agents, peptides, bleaching agents, anti-acne agents, human growth factors, serums, salicylic acid, other anti-acne acids and materials, microcapsules, capsules, other time-release products and substances, human growth factors, cytokines, collagen, brightening or lightening agents, peptides, peeling agents, acids, antioxidants, matrix proteins, saline, water (e.g., distilled, tap water, filtered, etc.) and/or other liquids or substances, as desired or required by a particular application or use. In certain embodiments, a treatment protocol may require the use of one, two or more different cartridges for a specific procedure. Thus, vials or cartridges 200 can be removed from or inserted into a handpiece assembly prior to or during a particular procedure. Alternatively, when a manifold system is being used to supply fluids to the handpiece assembly, one or more valves can be actuated (e.g., manually or automatically) to enable the desired fluid and/or other substance to be in fluid communication with the handpiece assembly.

In any of the embodiments disclosed herein, a cartridge or vial 200 or a separate bottle contained within a manifold system can advantageously permit a user to deliver skin tightening agents, platelet-rich plasma (PRP), exfoliation agents, peptides, bleaching agents, anti-acne agents, human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance to a handpiece assembly from one or more external fluid sources. For example, in some embodiments, the conduit 450 can be placed in fluid communication with one or more containers. Such containers can comprise the desired serums, salicylic acid, other anti-acne acids and materials, microcapsules, capsules, other time-release products and substances, human growth factors, cytokines, collagen, antioxidants, matrix proteins, brightening or lightening agents, peptides, peeling agents, acids, medicants, other fluids or substances, combinations thereof and/or the like, as desired or required by a particular treatment. Thus, the handpiece assembly 100 (e.g., the vial or container 200 of the handpiece assembly) can be used as an interface between the handpiece assembly and a relatively larger source of treatment media. For example, a handpiece assembly 100 can be advantageously placed in fluid communication with a multi-container system such as the one disclosed in U.S. patent application Ser. No. 11/392, 348, filed on Mar. 29, 2006 and published on Jul. 5, 2007 as U.S. Publication 2007/0156124, the entirety of which is hereby incorporated by reference herein.

According to certain arrangements, a cartridge 400 includes one or more solids, granular materials, gels, concentrated fluids and/or other substances that are adapted to dissolve, dilute, soften or otherwise mix when contacted by water, saline, other dilutants or dissolvents and/or other fluids. Thus, such materials or other substances can be placed within the cartridge 400 in one or more forms, such as, for example, as powder, granular material, a tablet, a capsule, a pill, other dissolvable solid, a concentrated solution, a gel and/or the like. In other embodiments, such solids, gels and/or other materials can be situated on the tip or other portion of the system (e.g., within a post or recess, adhered to one or more other exposed or hidden surfaces, within a removable cartridge upstream of the handpiece assembly, etc.), impregnated into a foam pad or other member and/or at any other location. Regardless of their exact composition, location and/or other details, such materials and/or other substances can be configured to dissolve, dilute and/or otherwise mix with water, saline and/or other fluids being conveyed through the handpiece assembly 100.

Improved Fluid Penetration and Other Beneficial Effects During Procedures

According to some embodiments, the effectiveness of performing a microdermabrasion procedure can be improved by the delivery of energy, light or air (or other fluid), the delivery of mechanical energy (e.g., acoustic energy, needle penetrations, etc.), the transfer of heat (e.g., to and/or from the skin) and/or the like. This can be conducted concurrently with a microdermabrasion procedure and/or before or after a microdermabrasion as desired or required. In some embodiments, for example, the delivery of energy (e.g., radiofrequency or RF, ultrasound, microwave, etc.), laser, light and/or the like to the skin surface can assist with one or more aspects of the skin treatment process (e.g., its effectiveness, the final result, etc.), healing and recovery. For example, in some embodiments, the application of such ancillary treatments or modalities can improve skin texture and look. In some embodiments, recovery time following a microdermabrasion and/or other skin treatment procedure can be reduced. The application of such treatments or items can also assist with the penetration of the various serums, other liquids and/or other substances used in connection with a skin treatment procedure (e.g., via fluid delivery from a vial or manifold to the tip of the handpiece assembly). The application of energy, mechanical disruption, transfer of heat to or from the skin and/or any other ancillary steps or processes can be used when the microdermabrasion system is being used with or without concurrent (e.g., continuous or intermittent) fluid delivery.

In some embodiments, a handpiece assembly and/or another aspect of a microdermabrasion system is configured to selectively deliver energy, heat (e.g., to or from the skin), air or other fluid, mechanical disruption, light and/or the like to the subject's skin. For example, a handpiece assembly can comprise one or more radiofrequency (RF) electrodes, ultrasound transducers, light, laser or microwave emitters and/or the like. Further, as discussed in greater detail herein, a handpiece assembly can include one or more lumens or passages that are configured to deliver air or other fluids (e.g., continuously, intermittently at a particular time frequency, etc.) to the skin. In other embodiments, however, the delivery of such energy and/or other items is performed using a separate device or system (e.g., a dedicated energy emitter unit, a dedicated fluid pump, etc.).

Air or Other Fluid Delivery

In some embodiments, it may be beneficial to provide air or other fluid to the skin surface being treated. The air can be delivered at a particular flowrate, pressure, intensity, pulsing rate or frequency and/or time duration to help achieve a particular effect on the skin surface. For example, air or other fluid can be pulsed onto the skin during, before and/or after a microdermabrasion procedure to promote and facilitate the transfer of serums, other liquids and/or other materials at least partially into the subject's skin tissue after exfoliation. In some embodiments, air pulsing can comprise square wave pulsing (e.g., having sequential air delivery and no air delivery phases, one after another, etc.).

In any of the embodiments disclosed herein, air pulsing can comprise providing air (e.g., puffs) to the skin surface being treated in accordance with a particular frequency, air flowrate, pressure, intensity and/or the like. For example, is some embodiments, the delivery of air or another gas is provided to the skin between in a pulsed manner. In some embodiments, the pulsing of air can include sequentially switching the delivery of air between a first (higher) pressure and a second (lower) pressure. In some embodiments, both the first and second pressures are positive pressures (e.g., relative to atmospheric). However, in other embodiments, the first (higher) pressure is positive (e.g., relative to atmospheric), while the second (lower) pressure is zero (e.g., no air delivery at all) or a negative pressure (e.g., suction or vacuum), as desired or required.

Figure 4:
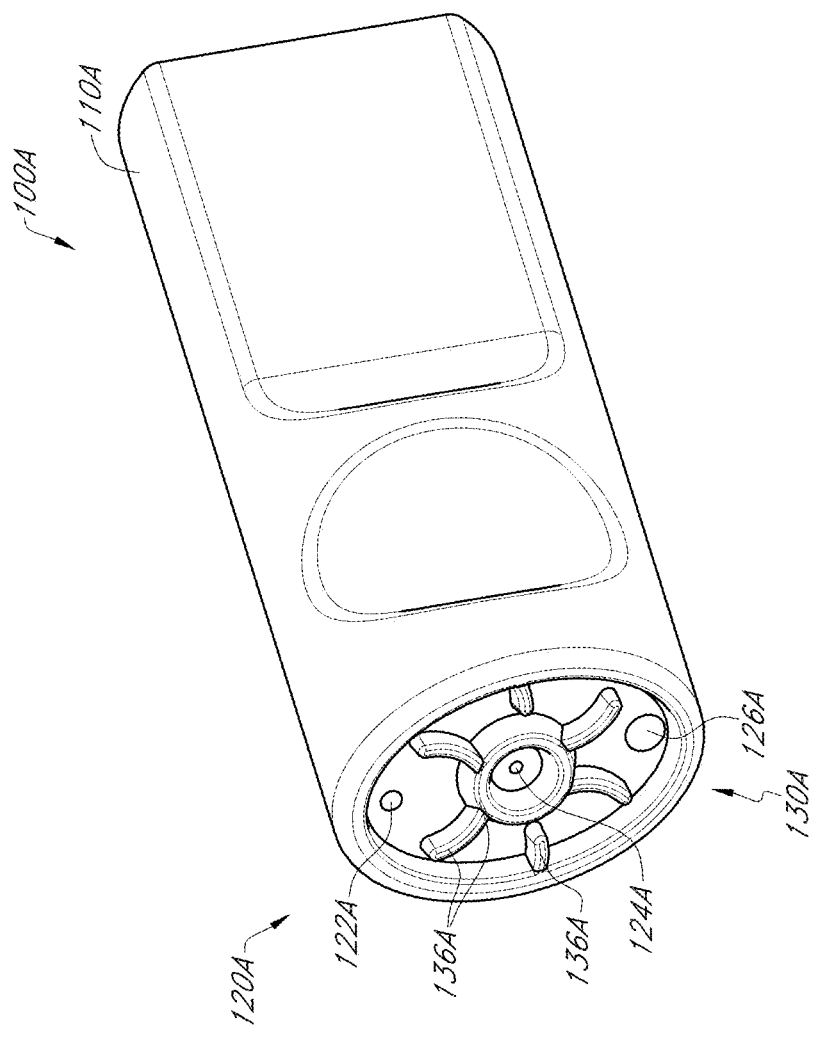
FIG. 4 illustrates a perspective view of one embodiment of a handpiece assembly of a skin treatment device configured to deliver air to the tip.
Figure 5A:
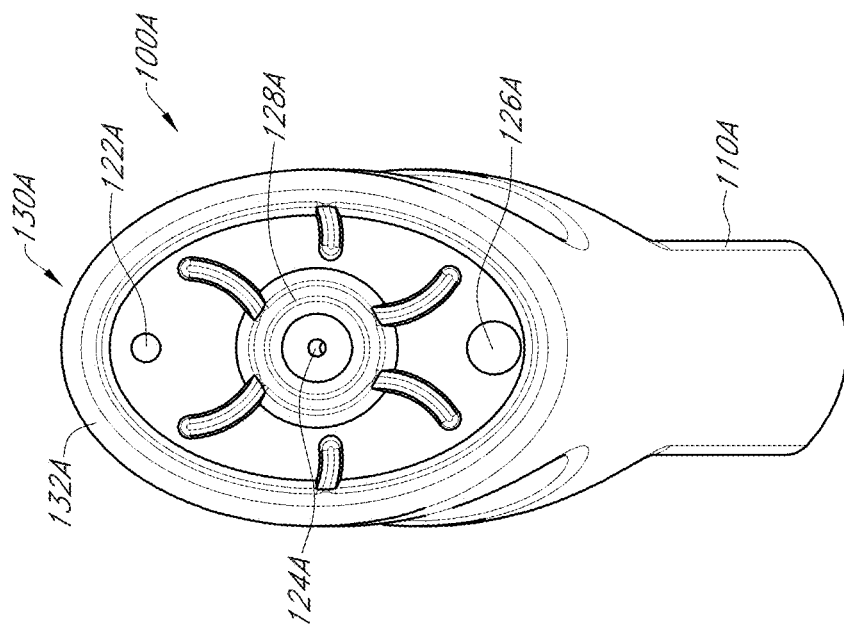

FIG. 4 illustrates one embodiment of a handpiece assembly 100A configured to abrade and/or otherwise treat skin while selectively delivering air (e.g., pulsed air) to the skin surface being treated. As shown, the handpiece assembly 100A can include a main body portion 110A and a distal tip 130A along its distal end 120A. As with other embodiments disclosed herein, the tip 130A can include a peripheral lip or ridge 132A that is configured to engage the subject's skin during use. The tip 130A can comprise one or more skin abrading members, features or portions 136A. Such abrading structures 136A can comprise one or more shapes, designs and the like. For example, in the depicted arrangement, a total of six abrading members 136A are oriented in a generally radial pattern. However, in other embodiments, more or fewer abrading members or structures can be used. For example, in some embodiments, the tip 130A does not include any abrading members. Thus, in such a configuration, the assembly 100A is configured to simply provide pulsed air to the skin of the subject, either alone or in combination with the delivery of one or more fluids and/or other materials. In some embodiments, one or more abrading members or structures included along the tip 130A can vary in type (e.g., posts, abrasive surfaces, ridges, etc.), pattern or layout (e.g., spiral, circular, oval, irregular, etc.), height or other dimensions and/or the like, as desired or required.

With continued reference to FIGS. 4 and 5A-5C, the handpiece assembly 100A can include one or more passages or conduits that extend to or near the tip 130A. For example, as shown, the assembly can include a fluid delivery passage 122A that selectively delivers serums, other liquids and/or other substances to the working surface of the assembly (e.g., from a vial or cartridge secured to the handpiece assembly, from a conduit in fluid communication with a separate tower or manifold system and/or the like). The assembly 100A can also include a vacuum (e.g., negative pressure) or suction passage 126A that is configured to remove spent serums and/or other fluids, together with abraded skin and other debris, when the system is in use and the vacuum source is activated. Additional fluid delivery and/or waste conduit and/or openings can be included in an assembly.

In some embodiments, the handpiece assembly 100A can include one or more air delivery passages 124A that are configured to continuously or intermittently deliver air and/or other fluid to the tip 130A. As illustrated in FIG. 5C, such an air passage 124A can be located along or near the radial center of the assembly and can daylight within an interior lip or ridge 128A along the distal tip. As also shown in the longitudinal sectional view of FIG. 5C, the diameter of the air delivery passage 124A can be decreased or otherwise changed at or near the distal tip 130A. For example, such a narrowing in the diameter can help deliver the air or other fluid at a desired flowrate, velocity and/or pressure.

If, during use, the vacuum source is activated and peripheral lip 132A of the tip 130A is in contact with the subject's skin, the suction passage 126A can create a negative pressure along the distal tip (e.g., along the interior of the peripheral lip), thereby drawing one or more treatment serums or fluids to the tip 130A (e.g., via the fluid delivery passage 122A). Further, in some embodiments, the application of a negative pressure along the tip 130A of the assembly 100A can help draw the subject's skin in contact with the interior lip or ridge 128A. Consequently, in certain embodiments, only the region along the tip between the peripheral lip 132A and the interior lip 128A may be subjected to the suction created by the vacuum source. Thus, air can be selectively transferred through the air delivery passage 124A of the assembly and onto a subject's skin without losing negative pressure along the annular region of the tip defined by the peripheral and inner lips 132A, 128A. In some embodiments, this can advantageously permit the delivery of air to the skin of the subject during a "wet" microdermabrasion process (e.g., one in which treatment fluids are delivered to the working end of the device).

As noted above, in some embodiments, air is delivered through the air delivery passage 124A in individual puffs. Accordingly, depending on their volume, intensity, pressure and/or other properties, such puffs can help exert an intermittent force along the subject's skin. As noted above, such mechanical or pneumatic agitation of the skin can provide one or more benefits. For example, the resulting force or pressure on the skin can help drive or push serums, liquids and/or other substances being delivered to the tip (e.g., via the fluid delivery passage) deeper into the skin tissue. The repetitive agitation created by the air puffs can also help loosen dirt, oils and/or other unwanted materials from the pores along the skin surface being treated.

The handpiece assembly 100A can be configured to allow a user to adjust the manner in which air is delivered through the air delivery passage 124 (e.g., including the specifics related to pulsing, such as, for example, the frequency of pulsing, high and low pressures during pulsing, the flowrate of air being delivered at various times during a pulsing operation, etc.) and/or the amount of negative pressure that is applied by the vacuum source through the suction passage 126A (e.g., or the amount negative pressure that is realized along the tip 130A). In some embodiments, the negative pressure within the suction passage 126A is sufficiently high to maintain contact between the subject's skin and the peripheral and inner lips 132A, 128A of the tip 130A during use. This can help maintain a steady and consistent flow of treatment fluids to the working surface while a skin surface is exfoliated or otherwise treated. A sufficiently high vacuum along the tip can also help ensure that the lips 132A, 128A will not lose contact with the skin surface as air is delivered (e.g. in puffs) to the skin surface. As discussed above, the manner in which pulsing is accomplished can be modified in accordance with a user's desires or expectations. Thus, one or more aspects related to the pulsing can be customized.

Needles and Other Mechanical Penetration and Agitation

According to some embodiments, one or more needles or other piercing members can be used to agitate and/or penetrate certain areas or regions of the subject's skin, before, during or following a microdermabrasion or other skin treatment procedure. The needles or other penetrating members can be moved in and out of adjacent skin tissue over a period of time. Consequently, a plurality of the small diameter passages can be created in the targeted skin tissue, at least temporarily. Such passages can allow serums, other treatment agents and/or other substances that are delivered or otherwise applied to the skin to be advantageously carried deeper into the skin tissue. The use of needles in connection with skin treatment procedures is discussed in greater detail below.

In other embodiments, one or more ultrasonic transducers can be positioned relative to the subject's skin before, during and/or after a microdermabrasion procedure so as to selectively deliver acoustic energy to the skin. In some embodiments, the transducers are configured to deliver a relatively low amount of energy to the subject in order to at least partially agitate (e.g., mechanically) the targeted skin tissue. The delivery of ultrasonic energy to the skin may, in certain circumstances, cause the skin tissue to heat. In other embodiments, one or more cooling devices can be placed on or in proximity with a skin surface, as desired or required.

As with other energy sources disclosed herein, ultrasonic energy can be delivered by a handpiece assembly that comprises one or more transducers. However, in other embodiments, a separate device or component is used to deliver a desired amount of ultrasonic energy to or near the skin tissue.

Other Types of Energy Delivery

In other embodiments, the handpiece assembly and/or a separate (e.g., non-integrated) device or system is configured to selectively deliver energy to the targeted skin tissue of the subject. For example, the types of energy-based modalities that can be directed to the skin surface include radiofrequency (RF), microwave, ultrasound and/or the like. As noted above, such energy delivery can be performed before, during and/or after a microdermabrasion or other skin treatment procedure. In some embodiments, the application of such energy to the skin can provide one or more anatomical responses and/or benefits. For example, if the energy applied to the skin is sufficiently high, the skin tissue can be at least partially heated. Such heating and/or other physiological (e.g., biochemical, biological, chemical, etc.) response or effect can, in some embodiments, facilitate the passage of serums and/or other treatment fluids at least partially within the skin tissue.

Light Treatment

Figure 6B:
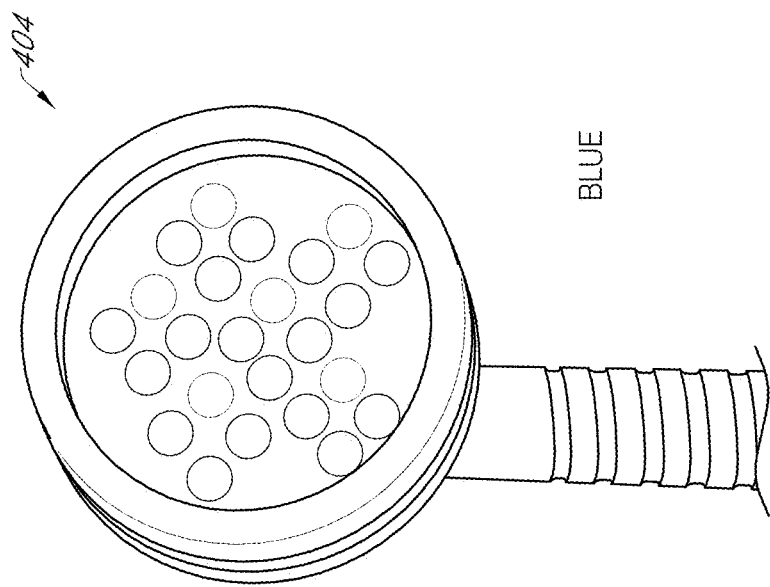
FIGS. 6A and 6B illustrate two different embodiments of a light wand device configured for use with a skin treatment system.
Figure 6A:
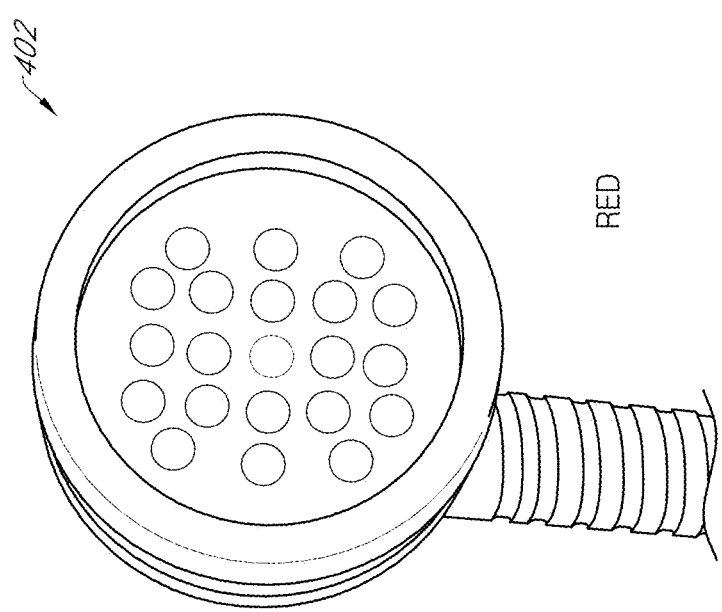

In some embodiments, one or more forms of light can be applied to the skin of the subject, before, during or after a microdermabrasion or other skin treatment procedure. The type of light, its intensity, power, frequency, wavelength, duration of exposure and/or other properties can vary, as desired or required for a particular application or use. In some embodiments, one or more properties of the light source can be varied, during a procedure and/or between procedures. In some embodiments, as illustrated in FIGS. 6A and 6B, the light comprises one or more LEDs or other illumination sources. As with other modalities disclosed herein, the light can be incorporated or attached to a handpiece that is being used for microdermabrasion. However, in other embodiments, the light source is separate and distinct from a microdermabrasion handpiece assembly.

In some embodiments, two or more different types of light sources can be provided as options for the subject or the user performing a procedure on the subject. For example, with reference back to FIGS. 6A and 6B, one of the light wands 402 is configured to emit blue light (e.g., light having a wavelength of approximately 475 nm), while another light wand 404 is configured to emit red light (e.g., light having a wavelength of approximately 650 nm). One or more wands or other light sources can be provided having other target colors. Any other color or light can be emitted, as desired or required. For example, a single light wand can be selected that is adjustable so to select an exact wavelength of light (in addition to or in lieu of selecting intensity, power and/or any other properties).

One or more light sources can be incorporated directly or indirectly into the handpiece assembly that is configured to perform microdermabrasion. For example, an annular light can be positioned along or near (or embedded partially within) the lip at the distal tip of a microdermabrasion handheld assembly. In other embodiments, the light can be removably mounted along an outside surface of the assembly.

In some embodiments, the use of light is configured to chemically or biochemically "activate" one or more treatment fluids and/or other substances have been or are being delivered to the skin surface of the subject. The activation of certain substances can provide one or more therapeutic or otherwise beneficial results. In other embodiments, the use of red, blue and/or other light can provide one or more direct benefits to the targeted skin tissue. In some embodiments, for example, red light therapy can be used to complement other skin care treatments, while blue light treatment can improve the general appearance of oily and/or acne-prone skin.

In some embodiments, light can be used to heat and/or at least partially modify or affect (e.g., at the cellular level) skin and adjacent tissue of the subject. For example, heat-producing or heat-inducing light source can be directed at the skin for a specific time period, before, during or after a skin treatment procedure (e.g., microdermabrasion). Light sources can include bulbs (e.g., incandescent, fluorescent, low-pressure sodium, high-intensity discharge, etc.), LEDs, lasers and/or the like. As discussed in greater detail below, heating of the skin can provide one or more benefits to the subject. For example, heating of skin tissue can enable the pores of the subject to open or dilate (e.g., allowing serums and/or other treatment fluids or substances to penetrate deeper into the skin surface). Heating of the skin can also increase blood circulation in the adjacent vessels (e.g., to help improve healing and recovery following a treatment procedure).

Thermal Treatment

Exposing the skin to hot and/or cold temperature can assist with various aspects associated with microdermabrasion and other skin treatment techniques and procedures. For example, as discussed herein, heating skin can open the skin's pores, thereby allowing serums, other treatment fluids or materials and/or the like to enhance penetration and migration of such materials into the skin. Further, cooling the skin can cause pores to close, at least partially, allowing therapeutic fluids and/or other materials that previously entered the pores to stay within the skin for a longer time period.

Figure 7A:
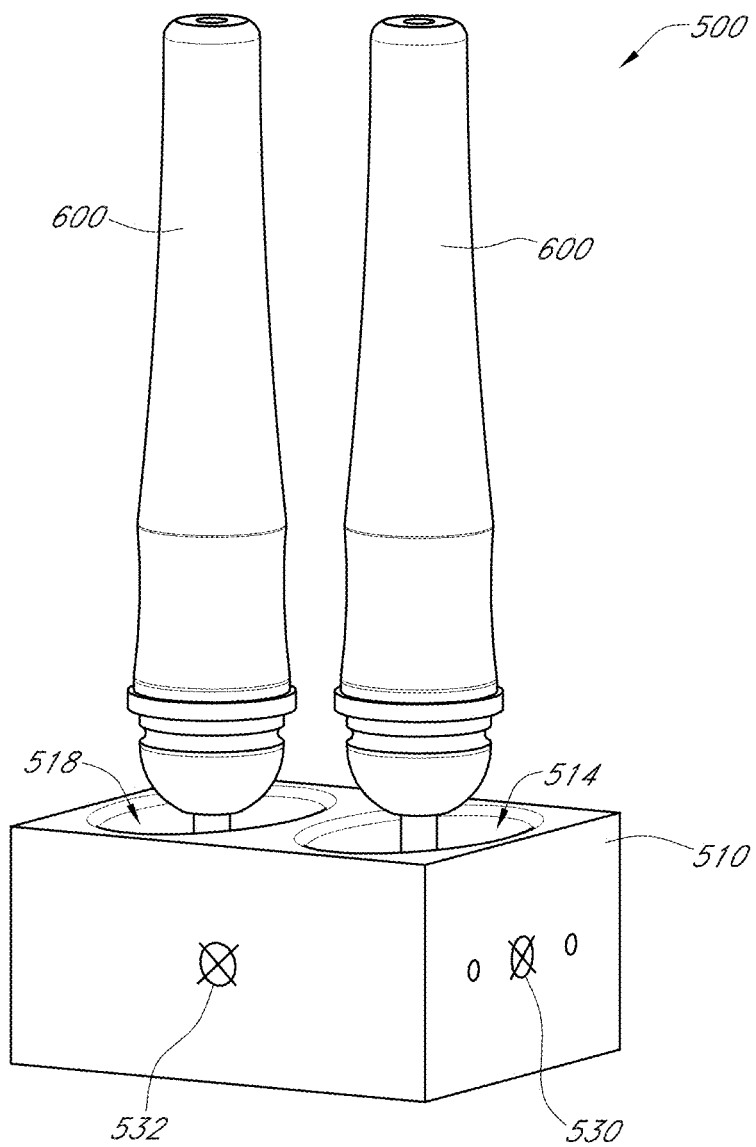
FIGS. 7A and 7B illustrate a station for a skin thermal conditioning system according to one embodiment.
Figure 7B:
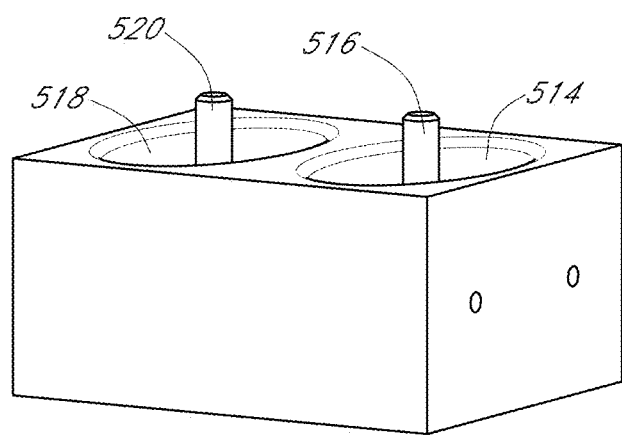

In some embodiments, one or more devices (e.g., handheld devices) can be used to conductively cool and/or heat skin, before, during and/or after a skin treatment procedure (e.g., microdermabrasion). One embodiment of such a heating and cooling system is illustrated in FIGS. 7A and 7B. As shown, the system can include a thermal docking station 510. In some embodiments, the docking station 510 comprises one or more wells, ports or openings 514, 518 for receiving and thermally recharging thermal conditioning handheld assemblies 600.

With continued reference to FIGS. 7A and 7B, the thermal recharging station 510 can be in thermal communication with one or more heating and/or cooling devices (not shown). In some embodiments, one or more thermoelectric devices (e.g., Peltier devices) are positioned along the outside, the inside and/or within the walls of the station 510. However, any other type of heating and/or cooling device can be used. In some embodiments, thermal conditioning devices are positioned along the exterior surfaces of the docking station walls (e.g., as schematically represented by circles 530, 532 in FIG. 7A). Regardless of the quantity, type, location, spacing, orientation and/or configuration of the thermal conditioning devices, the devices can be adapted to conductively heat or cool adjacent portions of the station 510, including the wells 514, 518 that receive the thermal handpiece assemblies 600.

In some embodiments, the station comprises one or more thermally conductive materials, such as, for example, aluminum, copper, other metal or alloys. As illustrated in FIG. 7B, one or more of the wells 514, 518 can include a pin, rod or other protruding member 516, 520. As discussed in greater detail below, the thermal conditioning handheld assemblies 600 can include a central opening. In some embodiments, the assemblies 600 are generally hollow along their centerlines. Accordingly, the assemblies 600 can be conveniently mounted or otherwise positioned on the pins 516, 520 when being placed within the wells 514, 518 of the station 510. Therefore, as illustrated in FIG. 7A, the pins 516, 520 can securely maintain the thermal handheld assemblies in a generally vertical orientation when the assemblies are positioned within the station 510 for thermal recharging.

When the thermoelectric devices and/or other heating and/or cooling devices of the station are activated, the wells of the station can be heated or cooled, in accordance with the desired thermal conditioning effect of that station 510. In some embodiments, if thermoelectric devices are used to heat or cool the station 510, an additional station (not shown) can be positioned on the opposite surface of the thermoelectric device so that the additional station also undergoes heating or cooling (e.g., the opposite thermal effect of the main station).

Figure 8A:
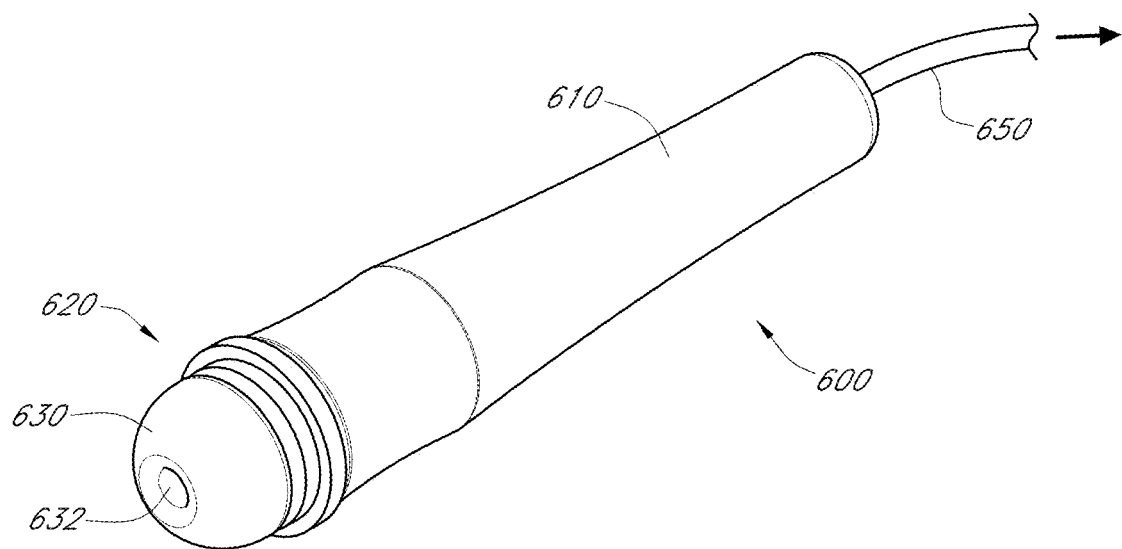
FIGS. 8A and 8B illustrate different views of a thermal conditioning handheld assembly configured for use with the station of FIG. 7A according to one embodiment.
Figure 8B:
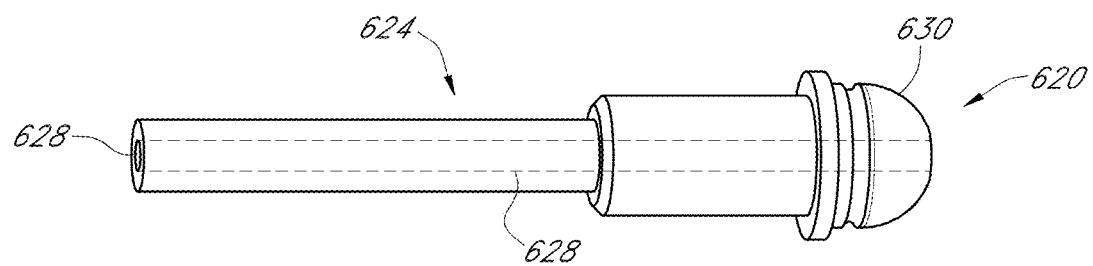

One embodiment of a thermal conditioning handheld assembly 600 is illustrated in FIGS. 8A and 8B. As shown, the assembly 600 can comprise an inner core 620 and an outer housing or shell 610. In some embodiments, the inner core 620 comprises copper, aluminum and/or any other high heat transfer material (e.g., beryllium, other metals or alloys, etc.). In some embodiments, the copper and/or other material can be coated (e.g., plated) with one or more layers of nickel, chrome and/or the like. The outer housing 610 can include ABS, Nylon and/or any other plastic or other material with a relatively low thermal conductivity (e.g., to avoid excessively or uncomfortably hot or cold temperatures being felt by a user who grasps and handles the assembly 600).

As illustrated in FIGS. 8A and 8B and noted above, the thermal handheld assembly 600 can include an interior lumen or opening 628 that extends completely or partially through the assembly. The proximal end of the assembly 600 can be placed in fluid communication with a vacuum conduit 650, if the assembly will be configured for suction. In such arrangements, the conduit 650 is placed in fluid communication with a vacuum or negative pressure source. In some embodiments, however, the heating or cooling system is configured to be used without suction.

With continued reference to FIGS. 8A and 8B, the handheld assembly 600 can comprise a distal head 630. In the illustrated embodiment, the head 630 includes a circular or rounded outer shape, having a generally smooth surface. In some embodiments, the head comprises one or more openings 632 that are in fluid communication with the internal lumen or passage 628 of the assembly 600. As best illustrated in FIG. 8B, in some embodiments, the head 630 forms a unitary structure with and is part of the core 620 of the assembly 600. As such, it advantageously comprises one or more high heat transfer materials (e.g., copper) that can be heated or cooled relatively quickly when placed within a well of the station 510.

Figure 8C:
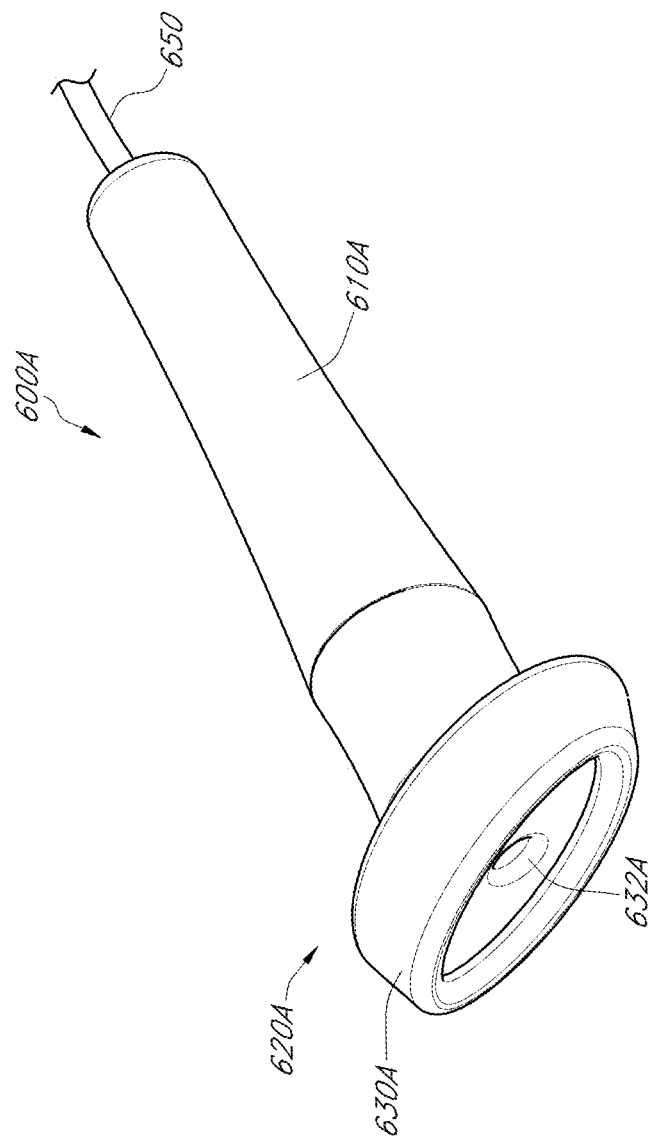
FIG. 8C illustrates a thermal conditioning handheld assembly configured for use with the station of FIG. 7A according to another embodiment.

Another embodiment of a thermal handheld assembly is illustrated in FIG. 8C. As shown, the head 630A of this alternative embodiment is relatively larger than the one illustrated in FIG. 8A. Further, the head 630A is asymmetrical. The head or other portion of a heating or cooling device can be customized (e.g., with respect to size, shape, material, comfort level, etc.) for a particular application or use.

Regardless of their exact shape, size, configuration and/or other properties, the thermal handheld assemblies 600, 600A can be used to selectively heat or cool a subject's skin surface. As noted above, in one embodiment, the surface to be treated (e.g., using microdermabrasion, non-abrasive treatment using fluid and/or energy delivery, etc.) can first be heated to open the skin pores and/or provide one or more other benefits. With the pores open, a fluid delivery process can be performed, either with or without skin abrasion. Accordingly, any serums, other treatment fluids and/or other substances that are delivered to the working end of a skin treatment device (e.g., along the skin surface that was previously heated), could pass deeper and/or with greater ease into the open pores of the skin. Following the treatment protocol (e.g., fluid delivery only, fluid delivery with dermabrasion, etc.), the user can use a cold thermal conditioning assembly 600, 600A to cool the skin surface that was treated. As a result of cooling the skin surface, the pores of the skin can at least partially close, thereby trapping the potentially beneficial serums and/or other components within the skin. Such a treatment method can provide for a quicker recovery time, fewer complications and/or one or more other benefits or advantages.

As noted above, in some embodiments, the thermal conditioning handheld assemblies 600, 600A are configured to create a negative pressure or vacuum along the one or more openings 632, 632A at the assembly head 630, 630A. As illustrated in FIG. 8B, such openings 632 can be placed in fluid communication with an inner lumen or passage 628 of the core 620, which in turn, is in fluid communication with a vacuum conduit 650. Thus, the vacuum source can be activated in order to draw the subject's body toward, and potentially partially into the opening 632, when the vacuum is activated. Accordingly, the vacuum feature allows a user to maintain the distal head 630 of the assembly 600 in constant or substantially constant contact with the subject's skin during use. In some embodiments, the vacuum source is pulsed (e.g., using a square wave scheme, between a high and low value), creating a pulsing effect at the head 630 of the assembly. As discussed herein, the high and low values of pressure provided during a pulsing sequence can include positive air pressure (e.g., relative to atmospheric), negative air pressures (e.g., relative to atmospheric) and/or zero. In some embodiments, the pulsing can be helpful when the thermal conditioning handheld assembly 600, 600A is used to heat or cool sensitive portions of the subject's anatomy (e.g., lymph-rich tissues). In some embodiments, assemblies 600A having larger head (e.g., FIG. 8C) can be used to heat or cool larger portions of the body (e.g., back, torso, thighs, etc.).

According to some embodiments, the level of heating or cooling of the thermal assemblies 600 can be adjusted and controlled (e.g., by modifying the duty cycle of the thermoelectric devices or any other heating or cooling device that is thermally conditioning the station 510). In some embodiments, a thermostat and/or other temperature detection is used to ensure that the operating temperature of the station 510 and the handheld assemblies that the station is configured to heat do not reach dangerous or uncomfortable extremes.

In other embodiments, a skin surface can be heated or cooled using any other method or device. For example, skin can be heated using any of the energy or other modalities discussed herein (e.g., RF, ultrasound, microwave, etc.). In one embodiment, the liquids, serums and/or other treatment fluids delivered to the tip of a microdermabrasion device (e.g., from a vial or cartridge, a bottle of a manifold or tower system, etc.) can be heated or cooled before it reaches the skin surface. Therefore, one or more heating or cooling devices can be incorporated into the microdermabrasion handheld device or the fluid system that is coupled to the handheld device.

Manifold System

Figure 9:
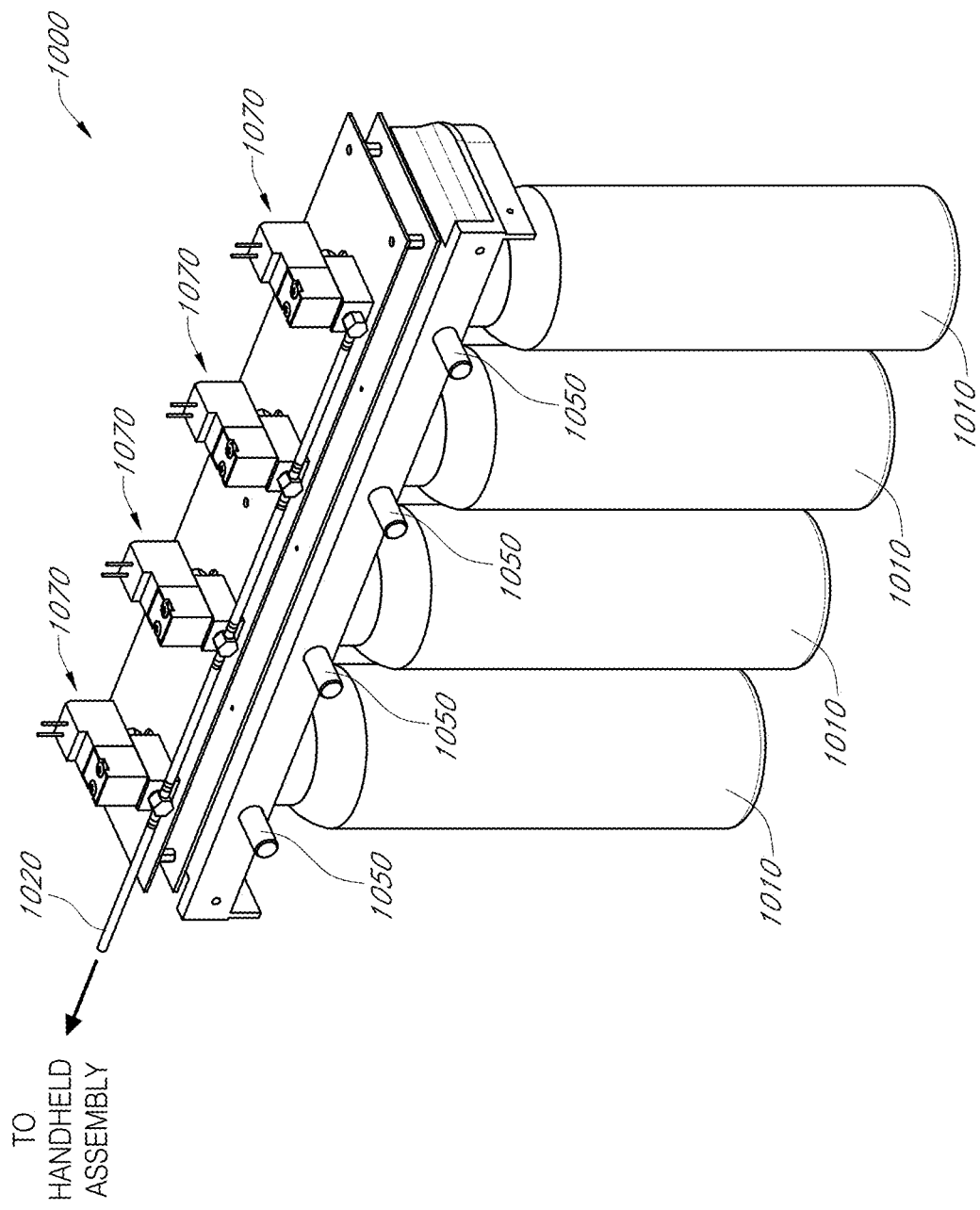
FIG. 9 illustrates a perspective view of one embodiment of a manifold system configured for use in a skin treatment system.

According to some embodiments, as discussed above with reference to the schematic of FIG. 3, a handheld assembly can be in fluid communication with a fluid manifold system (e.g., as opposed to having a vial or other fluid container positioned directly into the handheld assembly). One embodiment of a manifold assembly 1000 configured to receive multiple bottles or containers 1010 of one or more treatment fluids is illustrated in FIG. 9. As shown, the manifold assembly 1000 can include 4 different loading areas, each of which is configured to receive a bottle or other container 1010. Once properly secured to the station, a bottle 1010 can be placed in fluid communication with a main discharge conduit 1020 (e.g., via one or more intermediate conduits, not shown in FIG. 9).

With continued reference to FIG. 9, the manifold system can include a switch 1050 at each station. Therefore, once a bottle 1010 can been properly secured to a station, the corresponding switch can be pressed or otherwise manipulated to activate that station. Accordingly, fluid from the activated container can be used, and the system can deliver a desired volume or amount of that particular liquid to the handpiece assembly during a skin treatment procedure. In other embodiments, however, no switch is necessary. For example, various bottles 1010 can be loaded or otherwise secured to a station, and activation or deactivation of that station can occur automatically or manually.

With continued reference to FIG. 9, each station of the manifold system 1000 can include a solenoid valve or other flow regulating device 1070 that selectively opens or closes to permit fluid from the corresponding bottle or container 1010 from passing to the main discharge conduit 1020.

Figure 10:
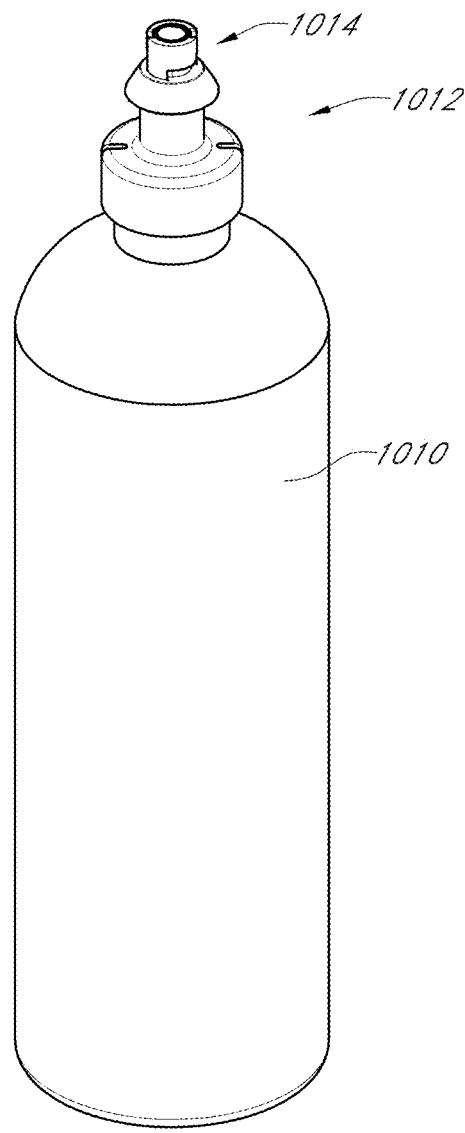
FIG. 10 illustrates a perspective view of one embodiment of a bottle configured for placement within the manifold system of FIG. 9.
Figure 11:
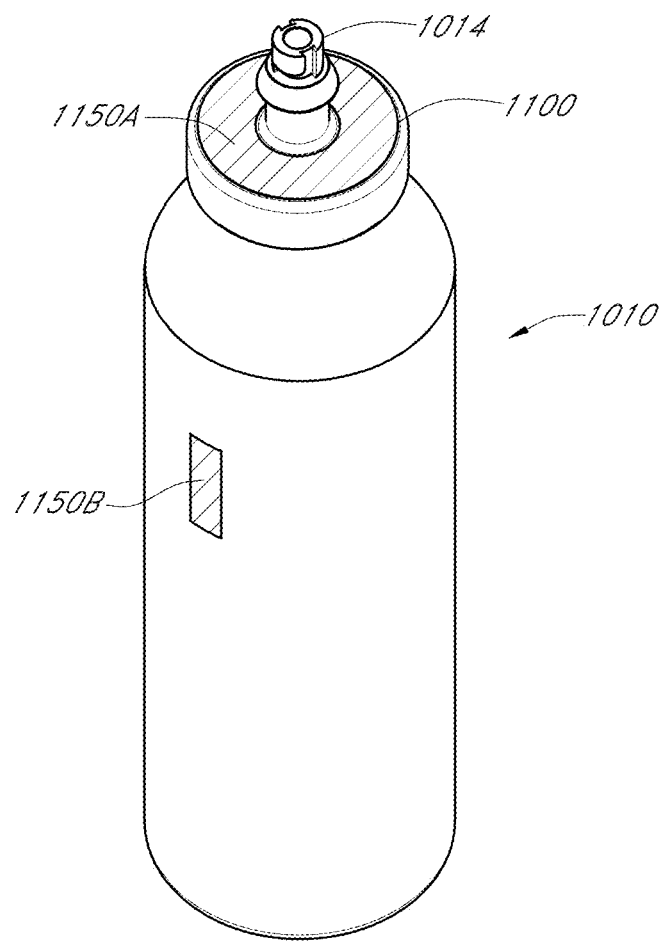
FIG. 11 illustrates the bottle of FIG. 10 comprising automatic identifiers according to one embodiment.
Figure 12:
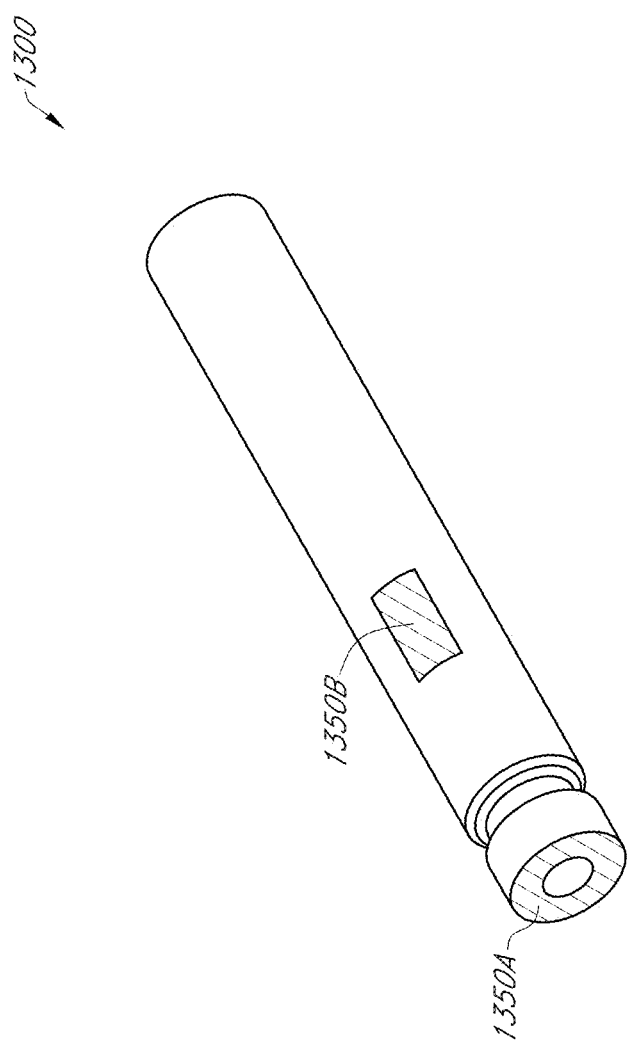
FIG. 12 illustrates a vial configured for placement within a handheld assembly of a skin treatment system according to one embodiment.

One embodiment of a bottle 1010 configured for placement into the manifold system 1000 is illustrated in FIGS. 10 and 11. As shown, the upper end 1012 of the bottle 1010 can include a nozzle fitting 1014 that is shaped, sized and otherwise configured to secure to a corresponding coupling of the manifold system 1000.

RFID and Other Identification Features for the Fluid Containers

In some embodiments, the various bottles or other containers 1010 positioned within a manifold system 1000 and/or vials or cartridges 1300 positioned within a recess of the handheld assembly can comprise an automatic identification tag 1150A, 1150B, 1350A, 1350B, such as, for example, a RFID chip, a barcode, etc. Such tags can be used to advantageously store information regarding the specific bottle, vial or other container. For example, the tag can include information regarding the contents of the container, expiration date, manufacturing date, size, lot number, skin procedure with which the contents are intended to be used, other limitations or restrictions on use (e.g., counter-indications, adverse effects, other fluids with which the contents should not be combined, etc.).

The RFID chip or other identifier can be read or otherwise detected (e.g., automatically, manually, etc.) by one or more readers or detectors of a manifold system 1000, a handheld assembly 100 and/or any other portion of a skin treatment system. For example, in some embodiments, such a reader can be placed at or near each station of a manifold system 1000 (e.g., adjacent the portion of the manifold to which the nozzle 1014 of the bottle 1010 secures). Accordingly, the RFID or other type of reader can detect and identify the RFID chip or other identifier of the bottle or other container. Likewise, a RFID or other type of reader can detect and identify the RFID chip or other identifier 1350 of a vial 1300 when the vial 1300 is properly positioned within the handheld assembly.

Therefore, in circumstances where the detected identifier is inconsistent with the proper, safe, appropriate and/or approved operation of the system, the system can be configured to prevent fluid from that vial or container from being used (e.g., by terminating the vacuum source, by maintaining a solenoid valve or other valve in the closed position, etc.).

The use of the RFID chips or other identifiers on the bottles, vials and/or other containers of the system can provide one or more other advantages or benefits. The collection of data regarding use of the corresponding container (e.g., bottle, vial, etc.) can be collected to generate reports for billing, reordering and/or other purposes. In some embodiments, the number of times that a container can be removed and reinserted within a manifold or handheld assembly can be limited (e.g., 1, 2, 3, 4, etc.), as desired or required. For example, such limits can help prevent or reduce the likelihood of contamination of the fluid. In some embodiments, the automatic identification of the fluid container being secured to the system (e.g., manifold station, handheld assembly, etc.) can allow the system to determine if a rinse, flush and/or other preparatory steps are required before the fluid from that container can be used.

According to some embodiments, the use of RFID chips or other identifiers can facilitate the execution of a particular skin treatment protocol by the system. For instance, the system can include various bottles containing fluids necessary to carry out any one of a number of various skin treatment procedures. For example, in one embodiment, a treatment sequence can be configured as a core or basic fluid delivery sequence (e.g., for use in a periodic or normal wet microdermabrasion procedure). Other possible treatment modes or sequences include, but are not limited to, anti-aging, anti-acne, skin lightening, oily skin treatment and/or the like. Each of the sequences or modes can include the delivery of one, two or more various serums and/or other fluids that are housed in the bottles secured to the manifold system.

In some embodiments, the system comprises a touch-screen and/or other user interface that allows a user to select from a number of several treatment protocols and/or other options. Such options can be pre-programmed (e.g., prior to the delivery of the system to a user). In some embodiments, the user is permitted to create its own customized protocols, as desired or required. Regardless, once a specific treatment protocol is selected by a user, the system's control module can be configured to automatically recognize whether the serums and/or other liquids necessary to complete the desired procedure have been loaded onto the system's manifold system. If the necessary products have been properly loaded onto the various stations of the system, the control module can initiate the treatment process. Alternatively, if the control module determines that one or more fluids are missing (and/or that fluids included in a bottle already loaded onto the manifold system are improper, e.g., because they have expired, they have been recalled, or for any other purpose or reason), the control module can prevent the treatment protocol from being initiated.

In some embodiments, the system (e.g., via a touchscreen or some other interface, visual, audible, etc.) can alert the user that one or more of the required serums and/or other substances necessary or desired for a selected protocol are either missing or should not be used. Accordingly, the system can prompt the user to make the necessary changes in order to resume with the protocol.

In other embodiments, a treatment system is configured to permit a user to manually enter information about the contents of a bottle or other container loaded onto a station of the manifold system.

Specific Treatment Protocols

According to some embodiments, any of the skin treatment systems disclosed herein can be operated under one of several different treatment schemes or modes. For example, the user can select between different preprogrammed and/or customized protocols. In some embodiments, protocols can relate to treatment of certain skin ailments, conditions or types, such as, for example, anti-aging, skin lightening, skin tightening, acne, rosacea, oily skin and/or the like. Based on the selected protocol, one or more serums and/or other liquids can be delivered to the skin during a procedure, either sequentially or concurrently. For example, in some embodiments, one or more of the following can be provided to the skin during treatment: bleaching agents, melanin production inhibiting agents, skin lightening products, vitamins, anesthetics (Lidocaine), human growth factors, non-human growth factors, platelet rich plasma (PRP), acids (e.g., glycolic acid, salicylic acid, etc.) antibiotics, chemical peel agents, antioxidants, exfoliating agents, peptides, stem cells, peroxides (e.g., benzoyl peroxide), retinols, and/or the like.

In some embodiments, one or more of the following can also be provided, either in lieu of or in addition to one or more of the fluids and/or other materials listed above: cytokines, soluble collagen, matrix proteins, other serums, other anti-acne acids and materials, microcapsules, capsules, time-release products and substances, water (e.g., distilled, tap water, filtered, etc.), saline, other dilutants or dissolvents, lotions, soothing agents, brightening or lightening agents, medicants, other non-active or active compounds, other fluids or materials, combination or mixtures thereof and/or any other substance.

In some embodiments, a subject's own PRP can be extracted and delivered to her or his skin using any of the devices and/or methods described herein (e.g., air pulsing devices). Such a procedure can speed up recovery following skin treatments, face lifts and/or the like.

According to some embodiments, a treatment protocol comprises a preliminary preparation phase or step. For example, such a step can include a lavage, cleaning, moisturizing and/or the like. In some embodiments, the preliminary phase or step includes one or more serum and/or other fluid treatments. For example, as discussed above, a treatment protocol can be selected based on the subject's condition (e.g., acne, oily skin, etc.) and/or desired result (e.g., skin lightening, skin tightening, etc.). This serum/fluid exposure step can be done with or without mechanical exfoliation (e.g., microdermabrasion). In some embodiments, a follow-up (e.g., tertiary) step includes the enhanced delivery of additional serums and/or other fluids using needles, air pulsing and/or the like. In such steps, the serums and/or other fluids can be delivered deeper below the subject's skin surface.

Needle-Based Treatment

Figure 13:
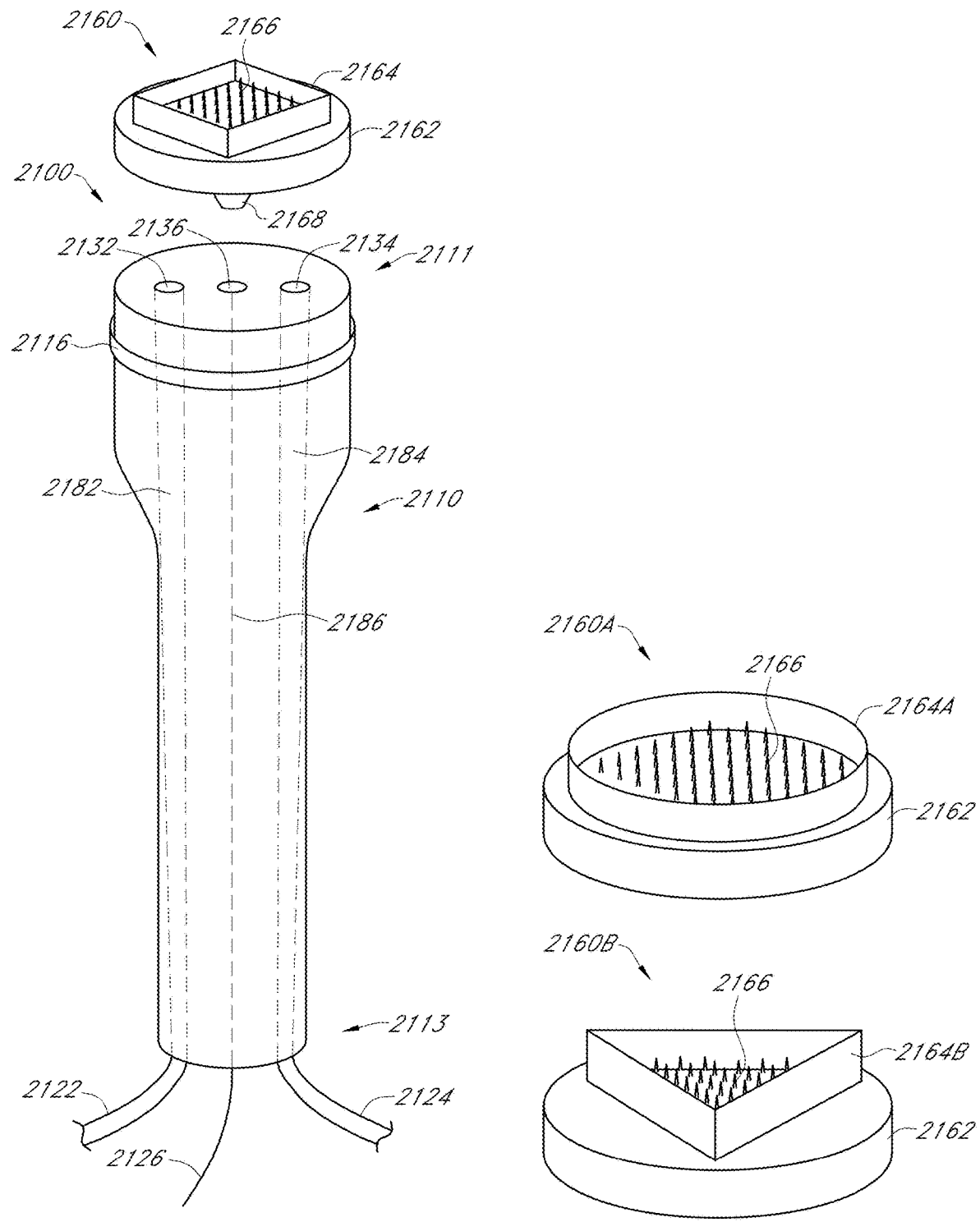
FIG. 13 is a perspective view of an embodiment of the main body portion and tip assembly, as well as additional embodiments of the tip.

FIG. 13 illustrates an embodiment of a handpiece assembly 2100 for treating the skin. As shown, the assembly 2100 can comprise a main body portion 2110 with a distal end 2111 and a proximal end 2113. In some embodiments, the assembly 2100 comprises a tip 2160 configured to engage the distal end 2111 of the main body portion 2110. The tip 2160 can be removable from the main body portion 2110. The tip 2160 and main body portion 2110 can be manufactured as a unitary construction. The distal end 2111 of the main body portion 2110 can include one or more O-rings 2116 or other sealing members. The O-rings 2116 can engage with the tip skirt portion 2162 so as to create a seal between the tip 2160 and the main body portion 2110. The main body portion can include one or more fluid delivery openings 2134 in, along or near the distal end of the main body portion, as well as one or more suction openings 2132 and energy contact points 2136. A fluid delivery opening 2134 can connect to a fluid source 2124 via a fluid delivery conduit 2184 in the main body portion 2110, a suction opening 2132 can connect to a suction source 2122 via a suction conduit 2182 in the main body portion 2110, and an energy contact point 2136 can connect to an energy source 2126 via an energy conduit 2186 in main body portion 2110.

In some embodiments, the tip 2160 comprises a tip skirt portion 2162, a base member 2165, a peripheral lip 2164, a plurality of needles 2166 and one or more tip ports 2168. The needles within the plurality of needles 2166 can be of uniform length and diameter or may vary in length (e.g. 0.5-2.5 mm) and/or diameter. The needles can comprise surgical steel (e.g., stainless steel), plastic and/or any other material suitable for penetrating the skin. The one or more tip ports 2168 can engage with the fluid delivery openings 2134, suction openings 2132 and/or the contact points 2136 along or near the distal end 2111 of the main body portion 2110. The peripheral lip 2164 can have many shapes, as shown in the embodiments 2160A, 2160B of the tip 2160 in FIG. 13. The tip 2160 can have a rectangular peripheral lip 2164, a rounded or oval peripheral lip 2164A, a triangular peripheral lip 2164B or any other shaped lip.

Figure 14:
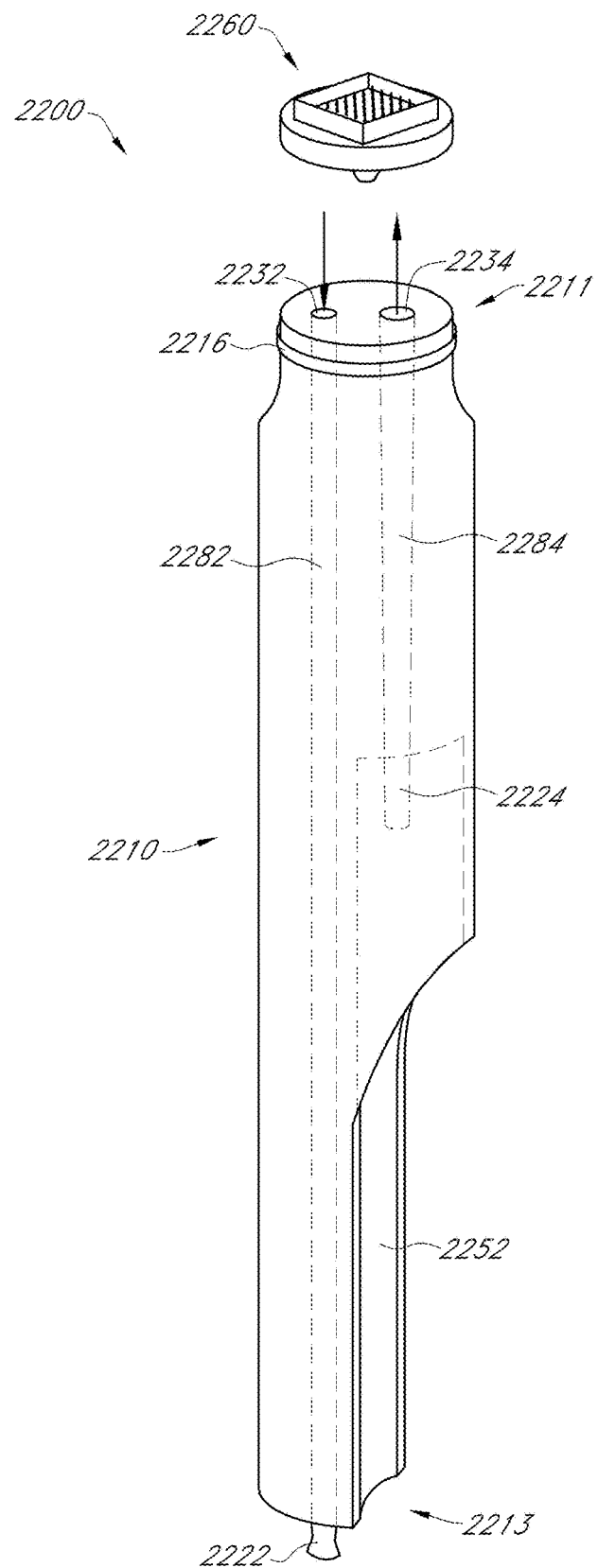
FIG. 14 is a perspective view of an embodiment of the main body portion and tip assembly showing a fluid delivery conduit positioned within a recess in the main body portion.

FIG. 14 shows an embodiment of a handpiece assembly 2200 for treating the skin where the handpiece assembly 2200 generally comprises a main body portion 2210 and a tip 2260. A fluid source point 2224 can be located within a hollowed out portion 2252 of the main body portion 2210 and is connected to a fluid delivery opening 2234 via a fluid delivery conduit 2284. This embodiment could allow for the use of a fluid cartridge as a fluid source. For example, the fluid cartridge could fit into the hollowed-out portion 2252 of the main body portion 2210 and could engage with the fluid source point 2224. The main body portion 210 could also comprise one or more O-rings 2216 or other sealing members that can engage with the tip 2260 to provide a seal between the tip 2260 and the main body portion 2210. The tip 2260 can be removable from the main body portion 2210. Alternatively, the main body portion 2210 and tip 2260 can be manufactured as a single unitary part.

Figure 15:
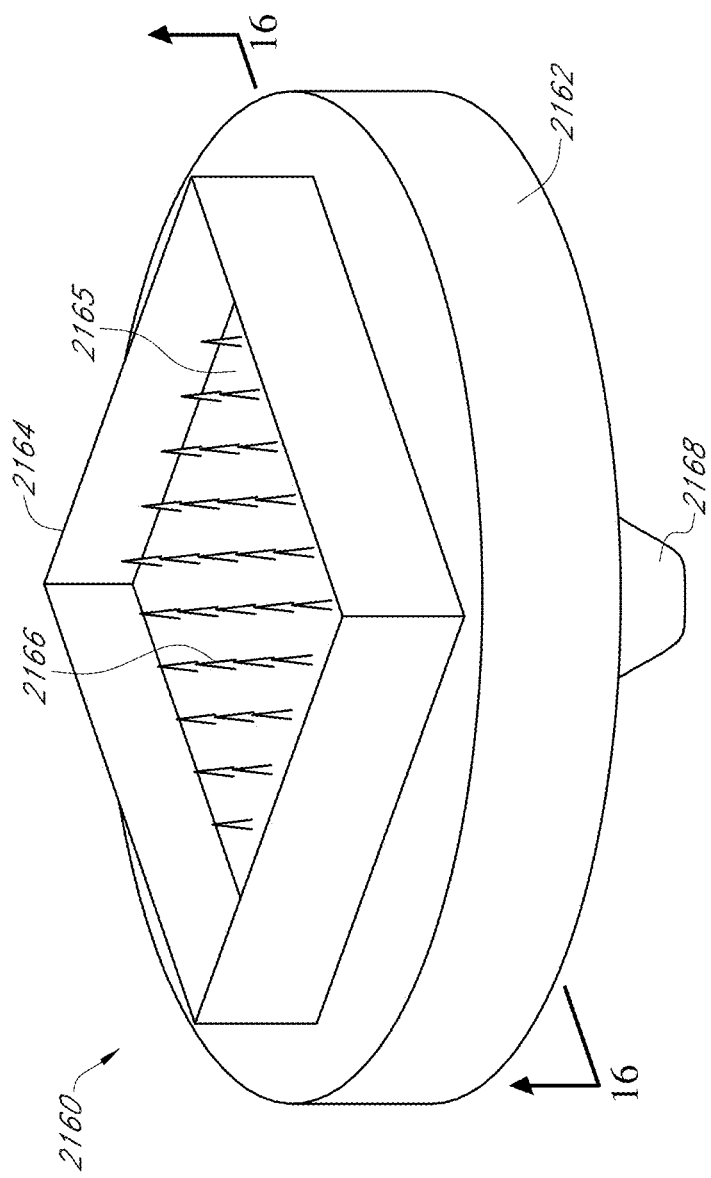
FIG. 15 is a close-up perspective view of an embodiment of the tip.
Figure 16:
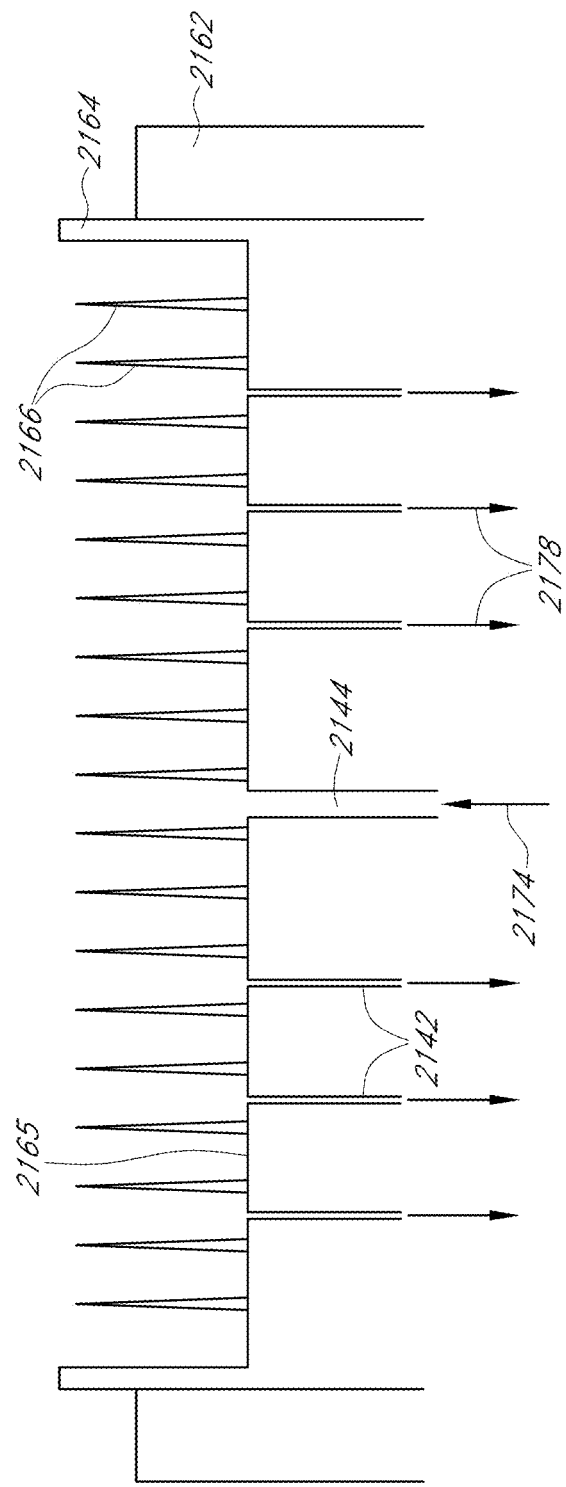
FIG. 16 is a cross-section view of an embodiment of the tip along cutting plane A-A of FIG. 15 showing a tip having multiple openings in fluid communication with a suction conduit.
Figure 16A:
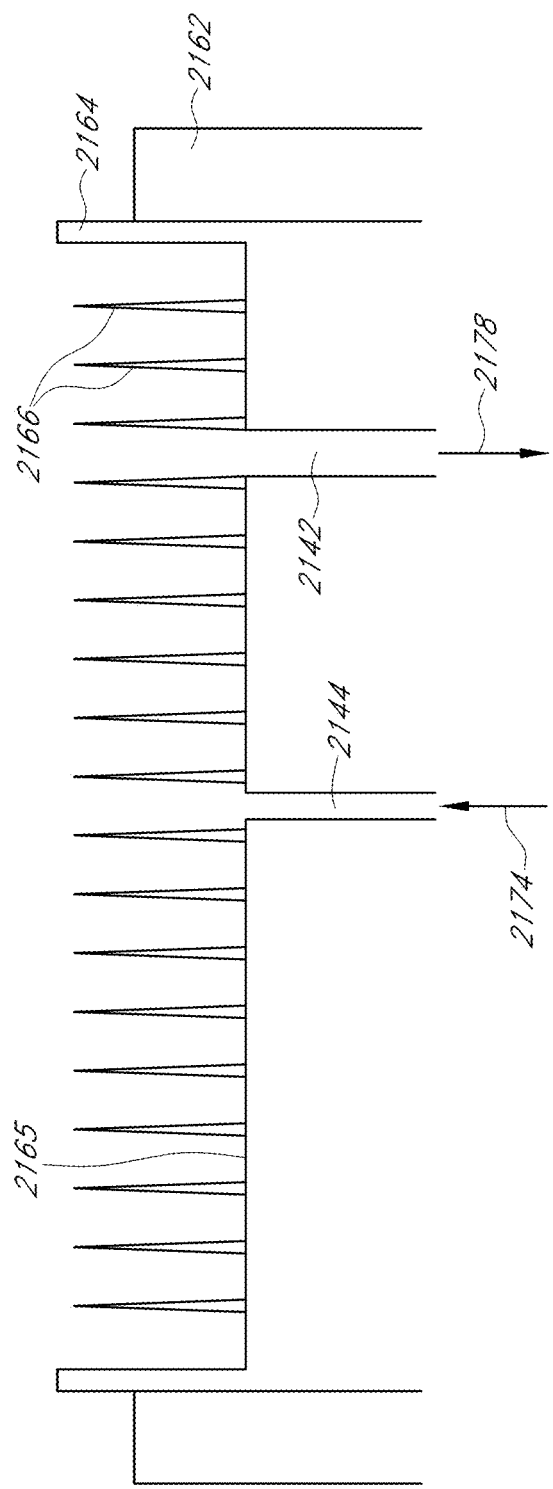
FIG. 16A is a cross-section view of an embodiment of the tip along cutting plane A-A of FIG. 15 showing tip having one opening in fluid communication with a suction conduit.

As shown in FIG. 15, a tip 2160 can comprise a peripheral lip 2164, a plurality of needles 2166, a base member 2165 and one or more tip ports 2168. In some embodiments, the tip additionally comprises a tip skirt portion 2162. In one embodiment, the tip skirt portion 2162, the base member 2165 and the peripheral lip 2164 can be adjustable with respect to each other or can be constructed as a unitary part. The plurality of needles 2166 can be coated with anti-oxidant or other skin nutrient. Additionally, a liquid-soluble material could be embedded in the surface of the needles 2166. As shown in FIG. 16, an embodiment of the tip 2160 can have one or more fluid delivery points 2144 and one or more suction points 2142. FIG. 16A shows an embodiment of the tip 2160 where there is a single fluid delivery point 2144 and a single suction point 2142.

Figure 17:
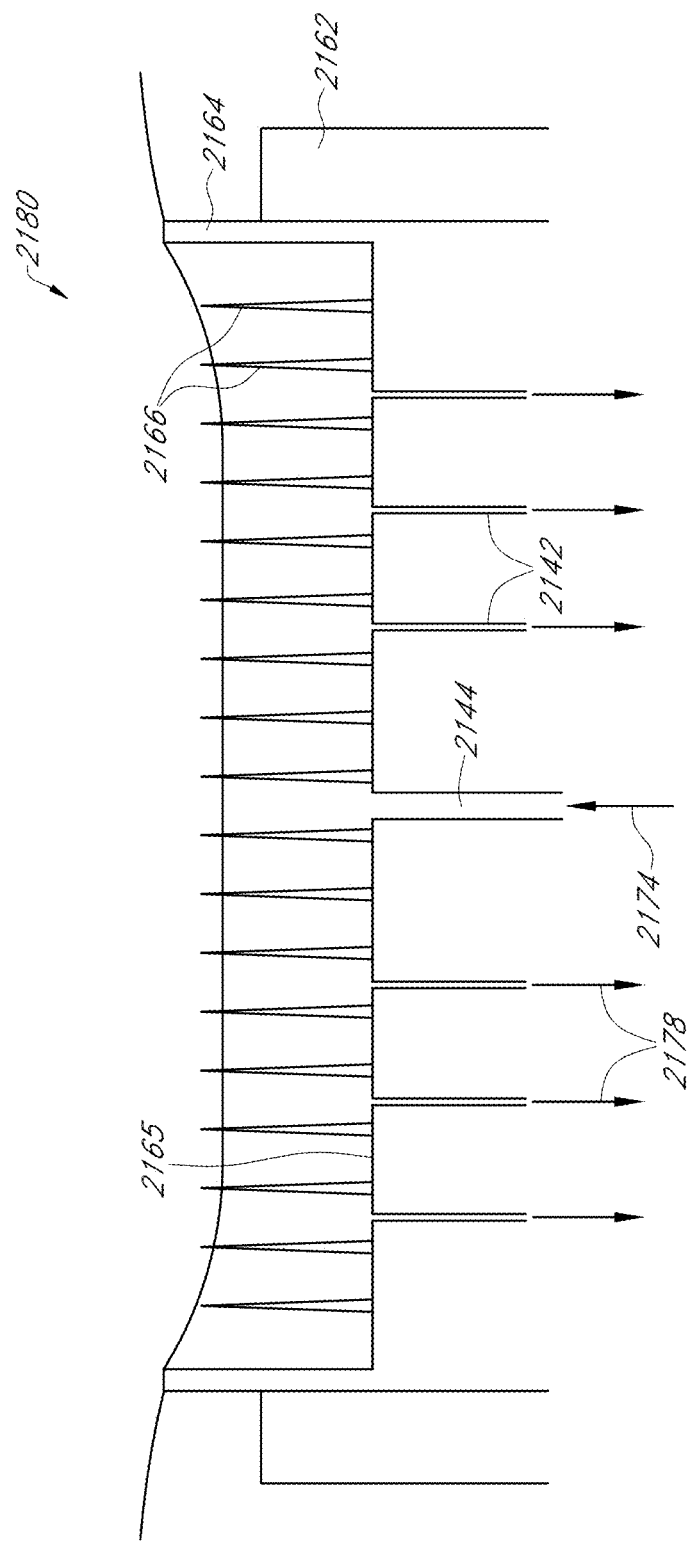
FIG. 17 is the same view from FIG. 16 where the needles are penetrating the skin of a patient.

In some embodiments, when the tip 2160 is applied to the skin 2180 of a patient, suction 2178 generated though one or more suction points 2142 on the tip can pull the skin 2180 onto the plurality of needles 2166, as shown in FIG. 17. Contact between the skin 2180 and the peripheral lip 2164 can create a seal around the treated area of skin 2180. The plurality of needles 2166 can be sized and the suction 2178 can be applied in such a way that the needles 2166 penetrate the epidermal layer of the skin 2180. During treatment, treatment fluids 2174 can be delivered to the skin via one or more fluid delivery points 2144. Waste and excess fluids can be removed from the treated area of skin 2180 via the one or suction points 2142. This treatment could occur before, during, after or in lieu of other microdermabrasion or other skin treatment procedures.

Figure 18:
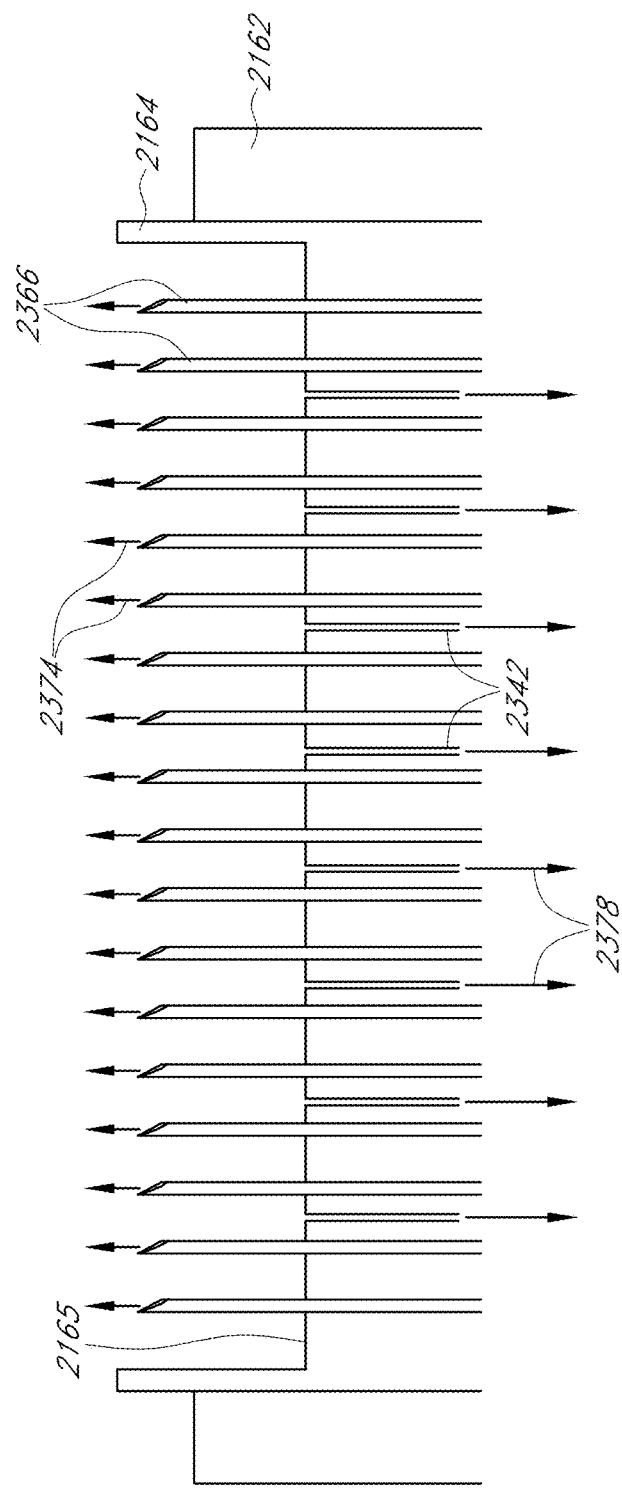
FIG. 18 is a cross-section view of an embodiment of the tip along cutting plane A-A of FIG. 15 showing hollow needles in fluid communication with a fluid delivery conduit.
Figure 18A:
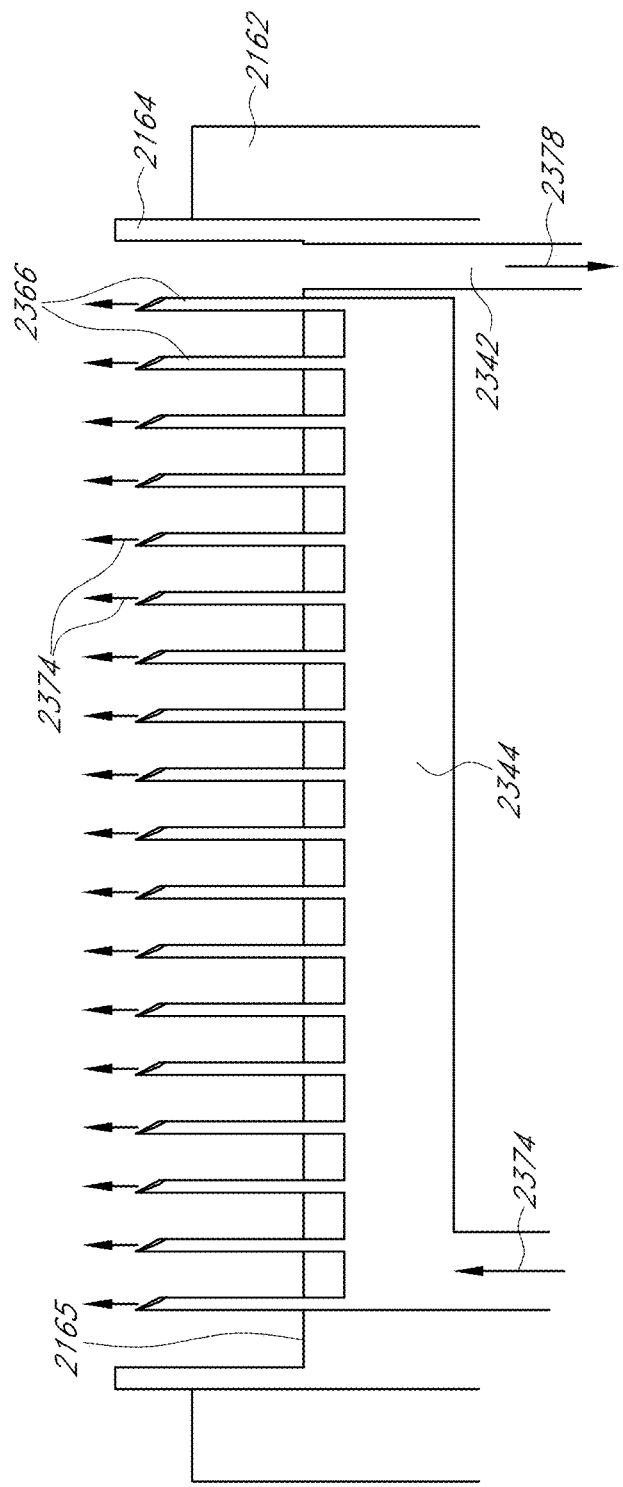
FIG. 18A is the same view as FIG. 18 showing a single fluid delivery conduit in fluid communication with the hollow needles.
Figure 19:
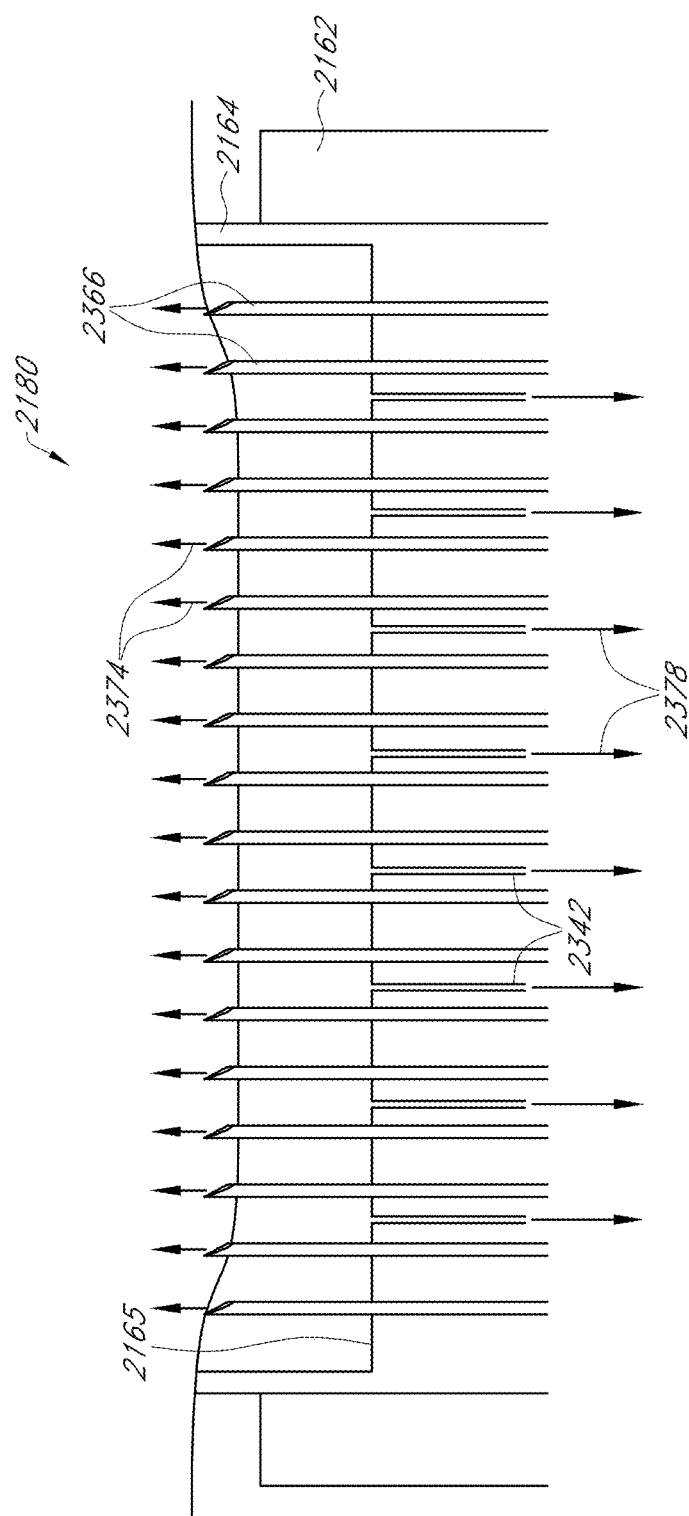
FIG. 19 is the same view from FIG. 18 where the needles are penetrating the skin of a patient.
Figure 20:
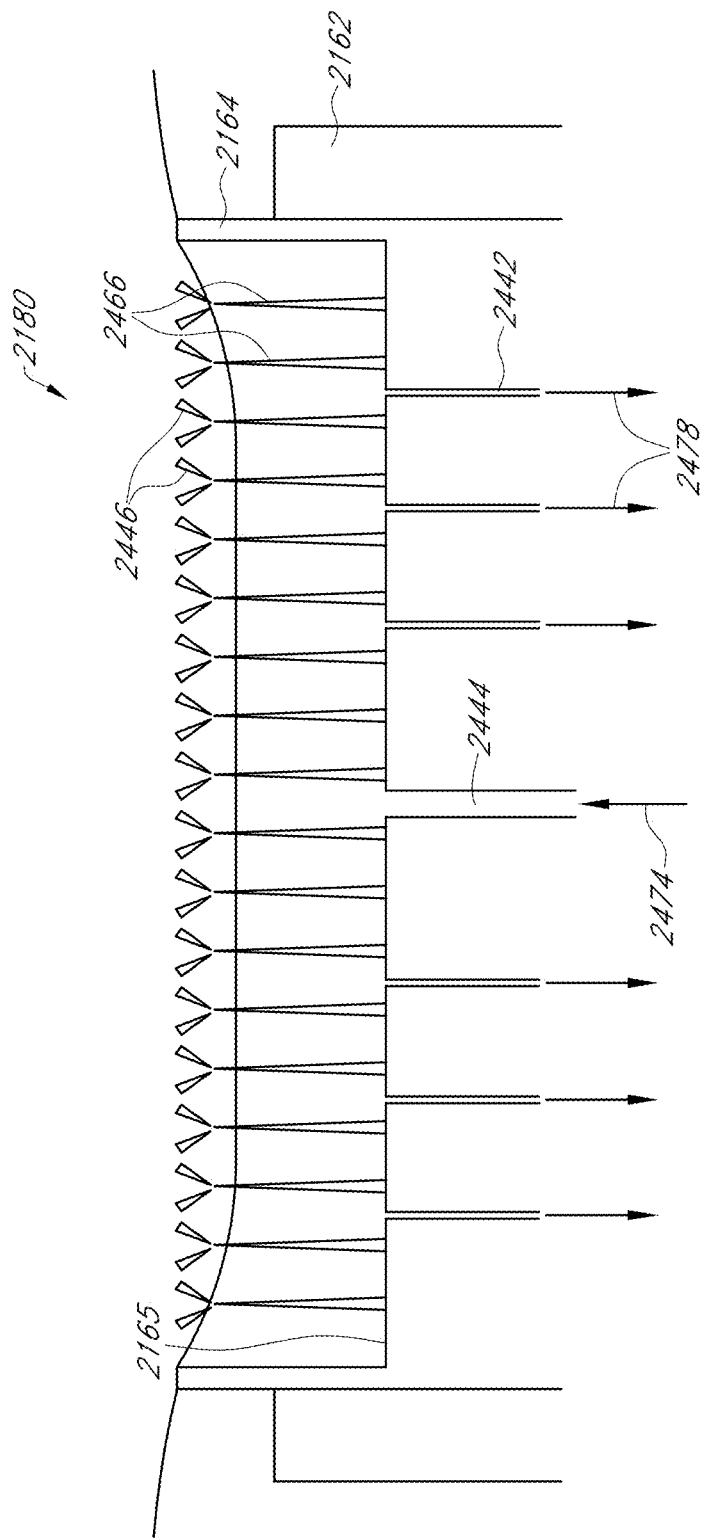
FIG. 20 is a cross-section view of an embodiment of the tip along cutting plane A-A of FIG. 15 showing the needles penetrating the skin of a patient and showing the needles emitting energy to the skin.

Hollow needles 2366 can also be utilized for treatment of the skin, as shown in the embodiment of FIGS. 18-20. In a hollow needle embodiment, for example, treatment fluids 2374 can be delivered at least partially into the skin 2180 via hollow needles 2366. The plurality of needles 2366 can be coated with anti-oxidant or other skin nutrient. Additionally, a fluid-soluble material could be embedded in the surface of the needles 2366. In some embodiments, one or more suction conduits 2342 can provide suction 2378 to assist in pulling the skin 2180 onto the needles 2366 and removing waste and/or excess fluids from the skin and/or the treatment surface. In addition, one or more fluid delivery points 2344 can be placed in fluid communication with one or more of the hollow needles 2366. Treatment fluids 2374 can include, without limitation, liquids, dermal fillers, hot or cold vapors, gases and/or the like. By way of example, when delivering vapors and/or gases to the skin 2180, one or more of the hollow needles 2366 can be configured to penetrate into the secondary layer of the epidermis of the skin 2180. The use of hollow needles 2366 to treat the skin 2180 can occur before, during, after or in lieu of other skin treatments, as desired or required.

The plurality of needles 2466 can also be used to delivery energy 2446 and/or heat to the skin 2180, as illustrated in FIG. 20. In some embodiments, energy 2446 is delivered via hollow needles and/or solid needles. When delivering energy to the skin 2180, one or more of the plurality of needles 2466 can be configured to penetrate into the secondary layer of the epidermis of the skin 2180. The source of the energy 2446 can be radiofrequency (e.g. RF energy), microwave, ultrasound and/or any other source of energy 2126 appropriate for treating the skin 2180. Using energy 2446 can at least partially damage the skin 2180 and help trigger a beneficial healing or tissue repair response. Use of energy 2446 to treat the skin 180 can be performed before, during, after or in lieu of other skin treatments.

Figure 21:
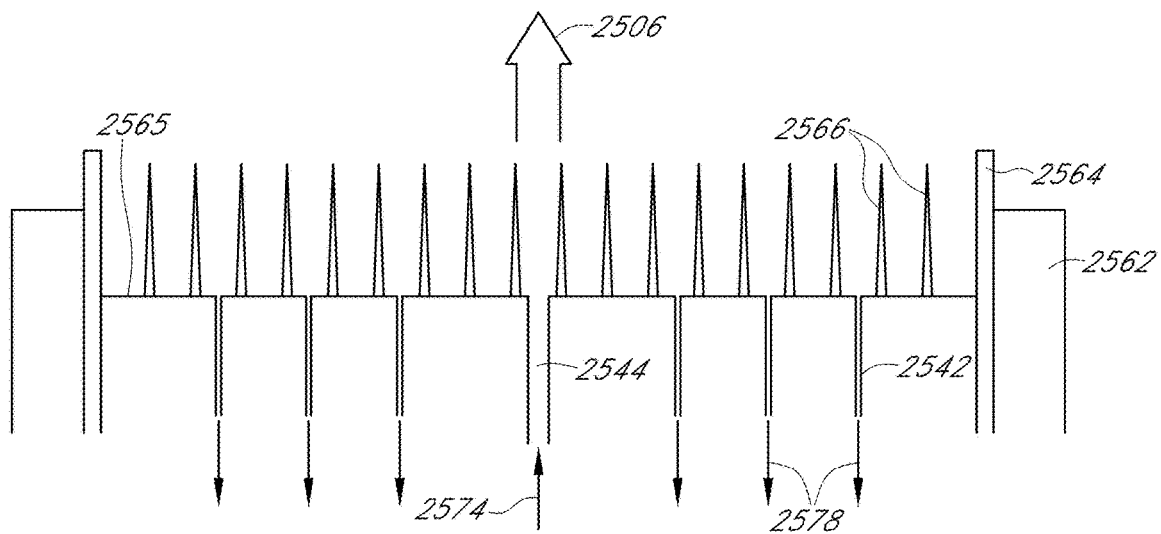
FIG. 21 is a cross-section view of an embodiment of the tip along cutting plane A-A of FIG. 15 showing a movable interior tip portion in two positions with respect to the peripheral lip of the tip.
Figure 21:
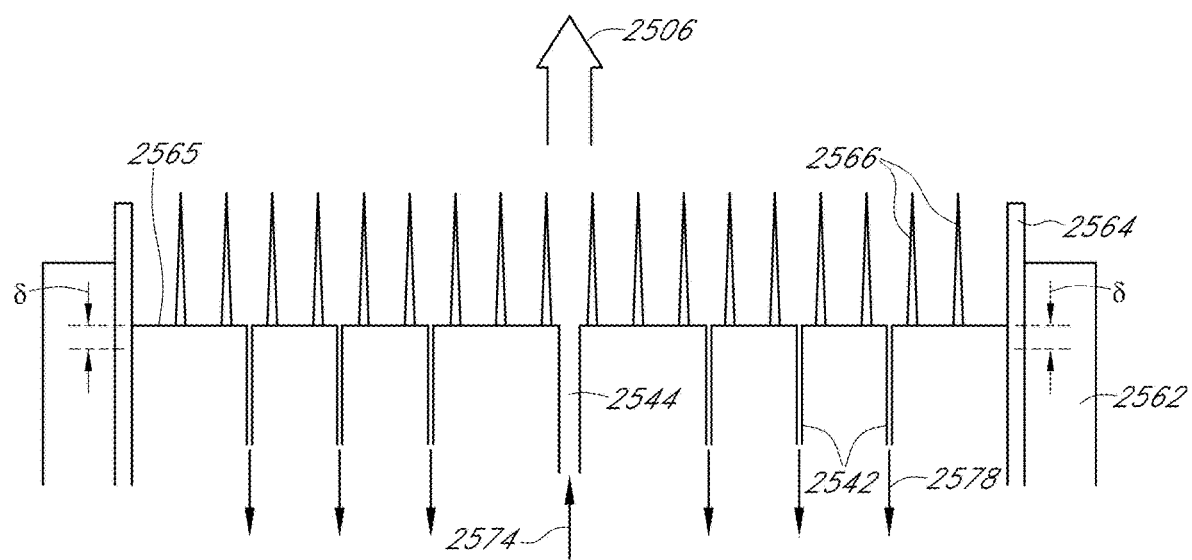

In addition to or in lieu of the use of suction 2578 to pull the skin 2180 onto a plurality of needles 2566, the plurality of needles 2566 and/or base member 2565 can be moved with respect to the peripheral lip 2564, as shown in FIG. 21. In an embodiment, a force 2506 (e.g. pneumatic, mechanical, etc.) is used to move the plurality of needles 2566 and/or base member 2565 a distance δ with respect to the peripheral lip 2564. The distance δ could be varied in order to achieve an optimal, adequate and/or preferred depth of penetration of the skin 2180 by the needles 2566. The force 2506 can be used in combination with or instead of suction 2578, and may be used with embodiments having hollow and/or solid needles 2566. The force 2506 can also be used in embodiments where energy 2446 is delivered to the skin 2180 via the plurality of needles 2566.

In any of the embodiments disclosed herein, the tip, the handpiece assembly and/or any other component or device can include rigid and/or semi-rigid materials. For example, the tips can comprise one or more thermoplastics, other polymeric materials, rubbers, metals and/or the like. Accordingly, the tips can be manufactured using any suitable method, such as, for example, injection or compression molding, thermoforming, other molding methods, casting and/or the like. The tips can be disposable so that they are used once or only for a limited number of times. Alternatively, the tips can be reused. Therefore, in such embodiments, the tips are preferably configured to withstand the required cleaning, sterilizing and/or disinfecting procedures to which they may be exposed. In addition, any of the tips disclosed herein, either directly or by reference, can be used in wet and/or dry systems. In general, wet systems include skin treatment devices, assemblies or systems in which serums, other fluids and/or other materials are conveyed to the tip during the procedure. On the other hand, dry systems include skin treatment devices, assemblies or systems in which serums, other fluids and/or other materials are generally not conveyed to the tip during the procedure.

As discussed herein, one or more fluids or other substances can be delivered to the tip of a handpiece assembly during a skin treatment procedure. In some embodiments, such fluids and/or other materials can be stored within a cartridge that is secured to the handpiece assembly. Alternatively, these fluids and/or other materials can be stored in a canister or other container that is separate from the handpiece assembly. In such arrangements, as discussed herein, the handpiece assembly can be placed in fluid communication with one or more containers using conduits or other fluid lines.

In any of the embodiments described and/or illustrated herein, or variations thereof, treatment fluids and/or other materials can be delivered to the tip of a handpiece assembly using one or more ways. For example, in some embodiments, serums or other substances can be delivered through a vial, cartridge, supply canister, fluid bottle (e.g., included in a larger manifold or multiple fluid distribution system) and/or the like. Such serums, compositions, other fluids or substances can be pre-mixed so that they are delivered to the tip and the skin unmodified or substantially unmodified.

In other embodiments, serums, fluids, gels or other materials can be in the form of a pack container dry granular material, viscous gels and/or the like. Such packs can be mixed with water or some other fluid by a user to a desired concentration. In other embodiments, one or more treatment materials can be impregnated or otherwise embedded into the tips of the handpiece assemblies. Thus, such materials (e.g., powers, solids, gels, etc.) can advantageously dissolve when they contact water, saline or some other liquid. In still other embodiments, the treatment materials can be contained within a capsule, tablet or other enclosure. Such enclosures can be configured to dissolve when placed in water or some other fluid. Therefore, a user may be required to place a capsule, the contents of a pack or some other materials into a cartridge, canister or other container and add water, saline or other fluid before use.

In some embodiments, one or more serums or other substances can be delivered to the treatment surface of a handpiece assembly to treat a particular skin condition. For example, the system can be used to treat acne, dry or oily skin, fine lines, sun-damaged skin, other skin diseases or disorders and/or like.

In some embodiments, the serums, other materials and/or a combination of such serums or other materials can be utilized for the treatment of substantially most or all skin types. For example, such serums and/or other materials can be used when the handpiece assembly exfoliates skin.

In another embodiment, the serums, other materials and/or a combination of such serums or other materials can be used during a follow-up (e.g., secondary, tertiary, etc.) or finish treatment step. For example, such serums and/or other materials can be used to hydrate the skin and/or lighten treat skin damage, either in lieu of or in addition to exfoliating skin. In such embodiments, the serums and/or other materials can comprise human growth factors, cytokines, soluble collagen, matrix proteins, other proteins, anti-oxidants, hyaluronic acid and/or the like.

In yet other embodiments, the serums, other materials and/or a combination of such serums or other materials can be used to target acne or oily skin conditions. Other serums, other materials and/or combinations of such serums or other materials can be used to target one or more types of skin conditions or treatments. Further, a particular treatment procedure can include or use one, two or more of such serums or other materials during various treatment phases (e.g., exfoliation, finish or polishing treatment, post-treatment, etc.).

In some embodiments, one or more kits can be developed that target a specific type of user, skin condition, desired result and/or the like. For example, such a kit can comprise serums and/or other materials that target teenage acne. As discussed, the serums and/or other materials contained in such kits can be in one or more different forms, such as, for example, liquids, gels, other fluids, powders, solids and/or the like. In some embodiments, such serums and/or other materials can be configured for immediate use. Alternatively, a particular amount of water, saline or other liquids, other dilution or dissolving agents and/or the like may need to be added to the serums and/or other materials to get them to a usable state. Kits can include one or more cartridges or other containers that are configured to be placed onto and removed from a handpiece assembly as discussed herein.

In addition, depending on who the target user is (e.g., teenagers, adults, etc.) and/or how severe a particular condition is, the concentration or strength of the serums and/or other materials can be varied. For example, for younger users, a kit directed at acne treatment can comprise lower concentrations of serums and/or other materials. By way of another example, kits comprising higher concentrations or strengths of serums and/or other materials can be used to treat oily skin or acne in adults. In another embodiment, a kit can be developed to target users whose skin is generally typical (e.g., the users' skin is not abnormally dry or oily, the users do not have excessive amount of acne or scarring, etc.).

As discussed, the kits can include one, two or more different types of treatment combinations. For example, a kit can comprise a first combination of serum(s) and/or other material(s) that is intended to target the exfoliation of skin. The same kit may include a second treatment combination that can be used in a follow-up treatment to treat oily skin or the like. In other embodiments, however, a kit can comprise more or fewer treatment combinations, as desired or required by a particular skin treatment procedure.

For any of the embodiments disclosed herein that incorporate the use of needles to at least partially penetrate skin, one or more of the needles or needle assembly incorporated into such designs can be configured to be selectively thermally-conditioned (e.g., heated, cooled). For example, in some embodiments, the heating or cooling of the needles can occur prior to the commencement of a needle penetrating procedure. In some embodiments, for example, the needles or needle assembly can be heated using the delivery of electrical energy thereto. In other embodiments, the needles or needle assembly can be selectively heated or cooled using one or more heating and/or cooling device (e.g., thermoelectric devices), convective heaters or coolers, fluid baths, ovens, refrigeration and/or freezing storage/housing units and/or the like.

Improved Fluid Penetration and Other Beneficial Effects During Procedures

According to some embodiments, as discussed above, the effectiveness of performing a treatment procedure can be enhanced by the delivery of mechanical agitation to the skin surface being treated. For example, air or other fluid can be selectively pulsed or otherwise delivered to the skin surface at the same time that exfoliation and/or treatment fluid delivery occurs. In other embodiments, other forms of mechanical energy (e.g., acoustic energy, needle penetrations, etc.) can be used, either in lieu of or in addition to fluid delivery. This can be conducted concurrently with a skin treatment procedure and/or before or after a skin treatment procedure as desired or required. As noted above, in some embodiments, it may be beneficial to provide air or other fluid to the skin surface being treated. The air can be delivered at a particular flowrate, pressure, intensity, pulsing rate or frequency and/or time duration to help achieve a particular effect on the skin surface. For example, air or other fluid can be pulsed onto the skin during, before and/or after a microdermabrasion procedure to promote and facilitate the transfer of serums, other liquids and/or other materials at least partially into the subject's skin tissue after exfoliation. In some embodiments, air pulsing can comprise square wave pulsing (e.g., having sequential air delivery and no air delivery phases, one after another, etc.).

In some embodiments, air is delivered through the air delivery passage 124A in individual puffs. Accordingly, depending on their volume, intensity, pressure and/or other properties, such puffs can help exert an intermittent force along the subject's skin. As noted above, such mechanical or pneumatic agitation of the skin can provide one or more benefits. For example, the resulting force or pressure on the skin can help drive serums, liquids and/or other substances being delivered to the tip (e.g., via the fluid delivery passage) deeper into the skin tissue. The repetitive agitation created by the air puffs can also help loosen dirt, oils and/or other unwanted materials from the pores along the skin surface being treated.

A handpiece assembly configured to deliver air or other gas during a skin treatment procedure can be configured to allow a user to adjust the manner in which air is delivered through one or more air delivery passages and/or the amount of negative pressure that is applied by the vacuum source through the suction passage (e.g., or the amount negative pressure that is realized along the tip). In some embodiments, the negative pressure within the suction passage is sufficiently high to maintain contact between the subject's skin and the peripheral and inner lips during use. This can help maintain a steady and consistent flow of treatment fluids to the working surface while a skin surface is exfoliated or otherwise treated. A sufficiently high vacuum along the tip can also help ensure that the lips will not lose contact with the skin surface as air is delivered (e.g. in puffs) to the skin surface.

According to some embodiments, one or more needles or other piercing members can be used to agitate and/or penetrate certain areas or regions of the subject's skin, before, during or following a microdermabrasion or other skin treatment procedure. The needles or other penetrating members can be moved in and out of adjacent skin tissue over a period of time. Consequently, a plurality of the small diameter passages can be created in the targeted skin tissue, at least temporarily. Such passages can allow serums, other treatment agents and/or other substances that are delivered or otherwise applied to the skin to be advantageously carried deeper into the skin tissue.

FIGS. 22A-22E illustrate various views of another embodiment of a skin treatment device 3200 comprising a main body 3210 and a tip 3240 positioned along the distal end of the main body. In some embodiments, the tip 3240 can be removably secured to the main body 3210. As illustrated in frontal view of FIG. 22B, the tip 3240 can comprise an outer or peripheral lip 3260 that is configured to contact the skin surface when the device 3200 is properly positioned relative to the subject's skin. The tip 3240 can additionally include an interior lip or ridge 3252 that is also configured to contact the skin surface being treated (e.g., simultaneously with the outer or peripheral lip or ridge 3260.

Figure 22A:
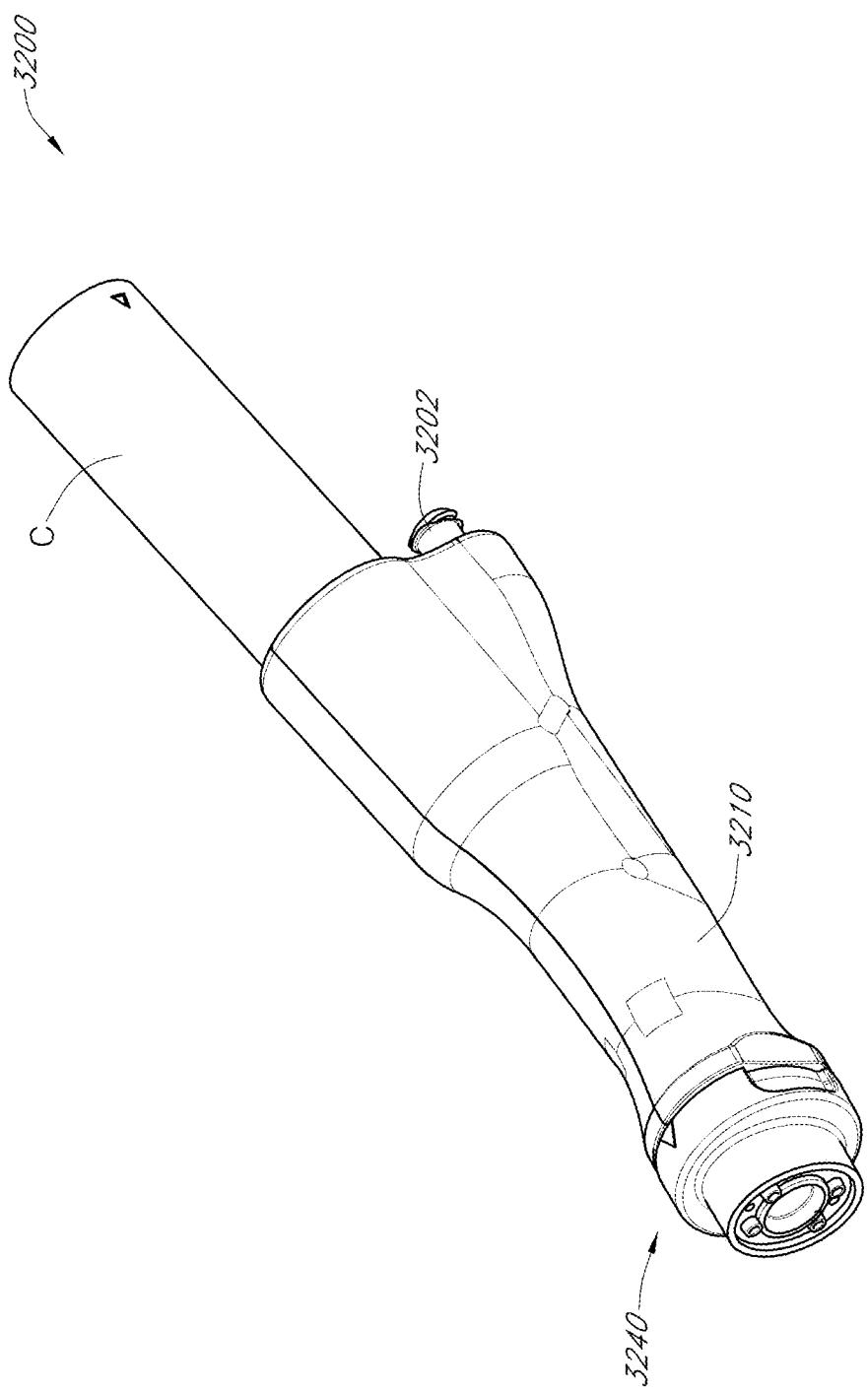
FIGS. 22A-22E illustrate various views of a skin treatment system comprising air pulsing, according to one embodiment.
Figure 22B:
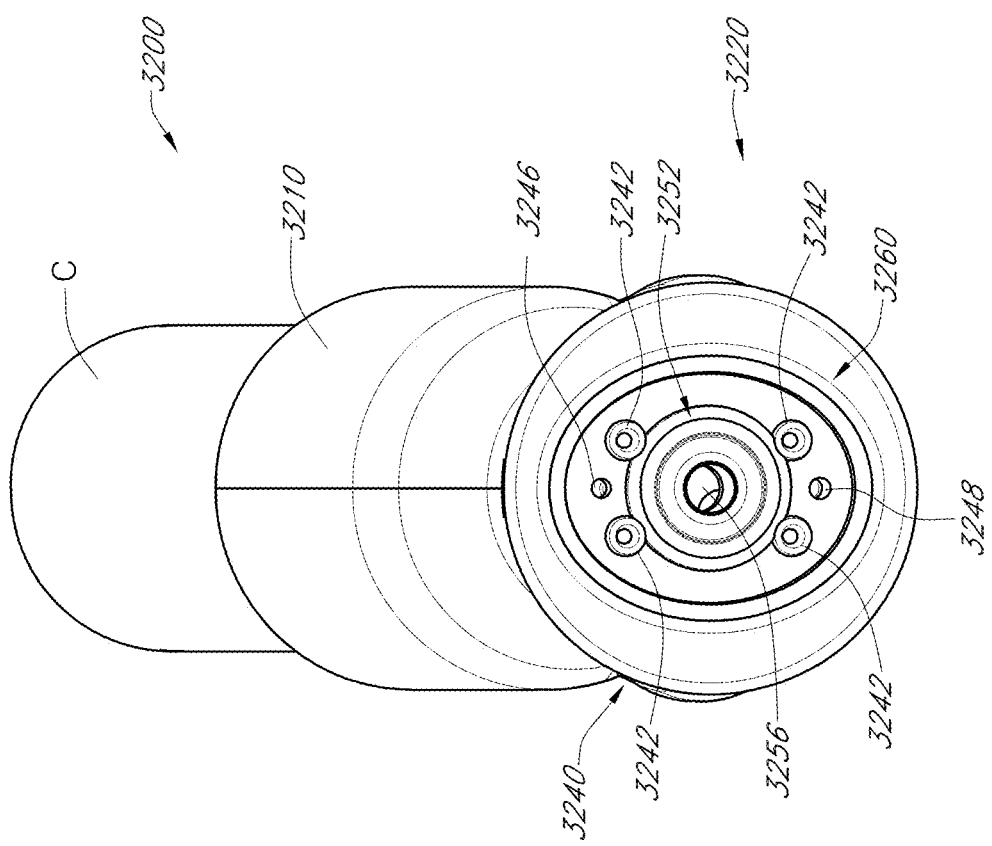

With continued reference to FIG. 22B, the generally annular area defined between the outer and inner lips or ridges 3260, 3252 can include one or more openings or ports. For example, as shown, the annular area can include one or more vacuum or suction ports 3242. In some embodiments, such ports 3242 comprise posts or other members that extend above the bottom surface of the annular region. As shown in FIG. 22B, the vacuum or suction ports 3241 can be strategically positioned adjacent or near (e.g., immediately surrounding) the inner ridge 3252. Such a configuration can assist to maintain contact between the lips or ridges 3260, 3252 and the subject's skin surface when the device 3200 is in use. The ability to consistently and adequately maintain contact between the tip and the subject's skin can be challenging when air or other fluid is being pulsed through the central opening 3256 of the tip, during use. As can be appreciated, the delivery of positive air pressure during pulsing can urge the tip (e.g., especially the inner lip 3252 and surrounding structures) to lose contact with the skin. Therefore, the system can be configured to provide sufficient suction or vacuum along, near or adjacent the pulsing port 3256 to ensure that proper skin contact is maintained during use of the device. In other configurations, the suction ports or openings 3242 can be flush, generally flush and/or recessed relative to the bottom surface of the annular region of the tip. Further, the shape, size, orientation, spacing, location, quantity and/or other characteristics of the ports or openings 3242 can be different than illustrated in FIG. 22B, as desired or required.

As illustrated in FIG. 22B, the annular region defined between the two lips or ridges 3260, 3252 can also include one or more fluid delivery ports 3246 and/or additional vacuum or suction ports 3248. In one embodiment, as illustrated in FIG. 22B, a single fluid delivery port 3246 is generally opposite of a vacuum or suction port 3248, facilitating in the delivery of a treatment fluid across a larger surface area of the skin being treated. In other embodiments, the quantity, orientation, location, size, shape and/or other details about fluid delivery ports and/or additional suction ports can vary.

With continued reference to FIG. 22B, the region defined within the interior of the inner lip 3252 includes an opening 3256 that is in fluid communication with one or more passages that extend through an interior of the device 3200. As discussed in greater detail herein, such an opening 3256 can be used to selectively provide pulsed air or other fluid to the skin during a treatment procedure.

Figure 22C:
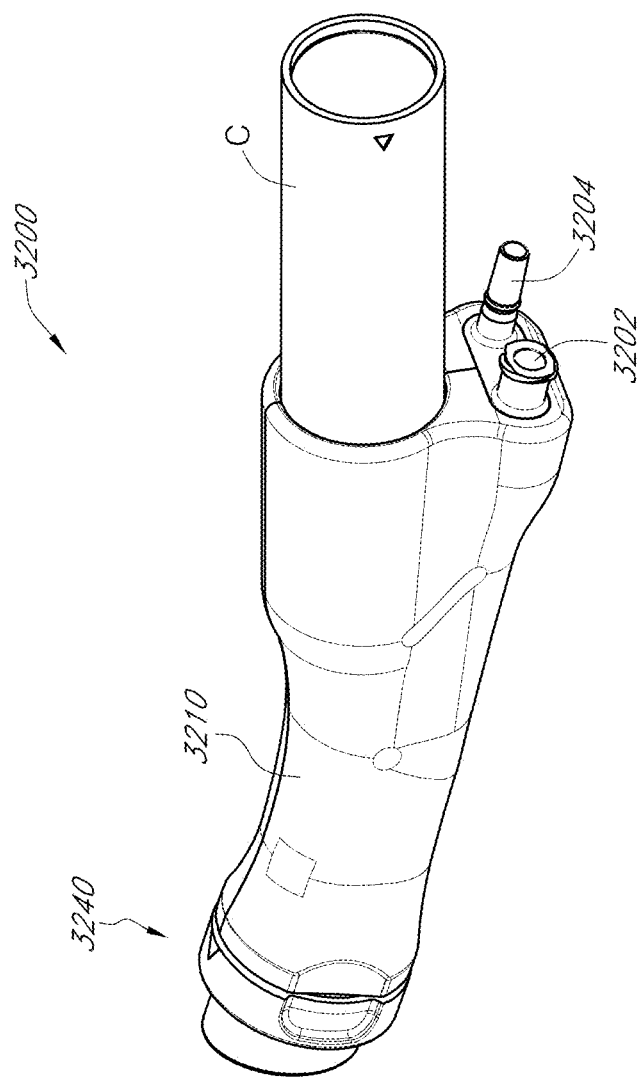
Figure 22D:
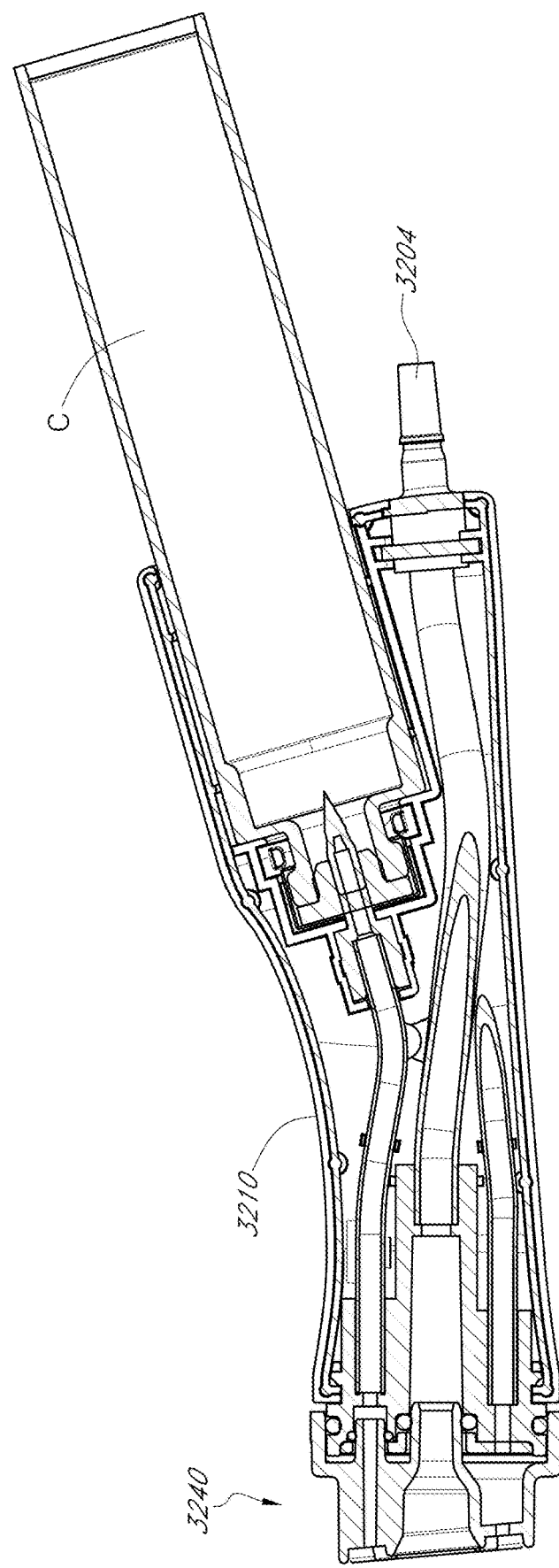
Figure 22E:
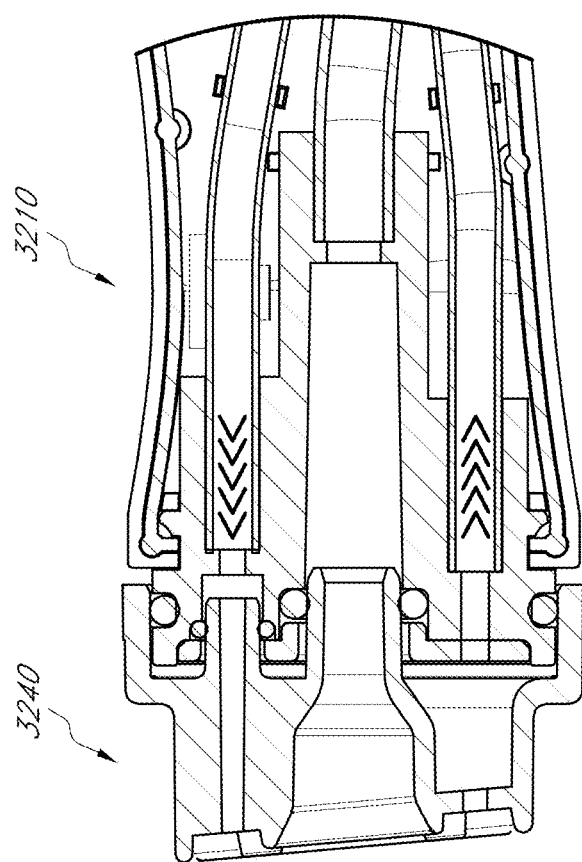

As shown in FIGS. 22B and 22C, the pulsing opening 3256 of the tip can be placed in fluid communication with a pulsing fluid connector 3204 toward the distal or rear portion of the device 3200 (e.g., via one or more interior lumens, conduits or other passages). Such a connector 3204 can be coupled to a pulsed air source, either directly or indirectly, to selectively deliver air to the tip and the skin surface at a desired frequency, duty cycle, volume and/or the like. As discussed, the delivery of such pulsed air or other fluid can assist with a deeper penetration of treatment fluids into the skin surface, thereby enhancing a skin treatment procedure. For example, in some embodiments, the mechanical agitation of the pulsing of air can drive, push or otherwise force treatment fluids that have been delivered to the skin surface deeper into the skin.

According to some embodiments, one or more parameters related to the pulsing of air or gases in the device 3200 can be adjusted by a user, as desired or required. For example, in some embodiments, the high and low pressure levels during a pulsing sequence can be modified. As noted above, the low pressure level can be zero, positive or above zero, or negative or below zero (e.g., with respect to atmospheric pressure). Thus, in some embodiments, air is pulsed between positive and negative (e.g., suction) pressures during a specific cycle. In other embodiments, both high and low pressure levels can be above atmospheric. Thus, a pulsing cycle does not need to include a vacuum or suction phase. In other embodiments, the low pressure level is zero or around zero. These pulsing options can be applied to any embodiments disclosed herein that are configured or can be configured to be used with pulsed air delivery to the skin interface (e.g., for improved serum penetration into the targeted skin surface).

Although not illustrated in the embodiment of FIGS. 22A-22E, a tip 3240 that is configured to permit the pulsing of air along a skin interface can additionally comprise one or more abrading members (e.g., posts, spiral, ridges, brushes, sharp edges, roughened surfaces, etc.). Thus, in some embodiments, while the device 3200 is activated (e.g., during the delivery of pulsed air and/or during the maintenance of suction through corresponding vacuum ports, etc.), the user can selectively translate or move the tip of the device relative to the targeted skin surface to at least partially abrade and/or otherwise treat the skin.

However, in other embodiments, the device 3200 comprises a non-abrading tip 3240 for the purpose of driving serums and/or other fluids deeper into the skin. This can be performed as part of a preliminary, intermediate (e.g., secondary) or follow-up (e.g., tertiary) step in a treatment process or protocol, as desired or required. For example, in some embodiments, such a non-abrading device is used (and the corresponding method is utilized) following an abrading or preparatory procedure, step or phase.

With continued reference to FIGS. 22A-22E, device 3200 can be configured to be placed in fluid communication with one or more serums and/or other treatment fluids contained in a cartridge C. As shown, such a cartridge can be secured within a corresponding recess of the handheld device 3200, which in the depicted arrangement is located along the distal end of the device. In other embodiments, however, the device can include a port along its distal end (or along any other portion). Such a port (not shown in the illustrated arrangement) can be placed in fluid communication with a main fluid delivery line. In some embodiments, for example, such a main fluid delivery line or conduit can be configured to deliver serums and/or other fluids from a manifold system, such as those disclosed herein with reference to FIGS. 3 and 9.

As shown in FIG. 22C, the handheld device 3200 can include additional ports 3202, 3204 for connecting to a vacuum source and/or a pulsed air source. Such fluid sources can be separate from the treatment system or may be at least partially incorporated into the system, as desired or required. In some embodiments, at a minimum, the vacuum and pulsed air sources are in data communication with a control module or other controller to permit a user of the device to advantageously regulate the level of suction and/or the level of pulsing during use.

According to some embodiments, the pulsed air concepts can be combined with a movable needle assembly that is configured to selectively penetrate skin. A system that combined needle penetrations with pulsed air delivery can provide more enhanced (e.g., deeper) infusion or penetration of serums and/or other liquids being delivered to the skin surface being treated. One embodiment of a combination needle penetration and pulsed air delivery device 3300 is illustrated in FIGS. 23A-23E. As discussed above with reference to FIGS. 22A-22E, the device 3300 can include an inner lip or ridge 3352 and an outer lip or ridge 3360. Such lips or ridges 3352, 3360 can be shaped, sized and otherwise configured to contact a skin surface when tip 3340 of the device 3300 is properly positioned against a subject.

Figure 23A:
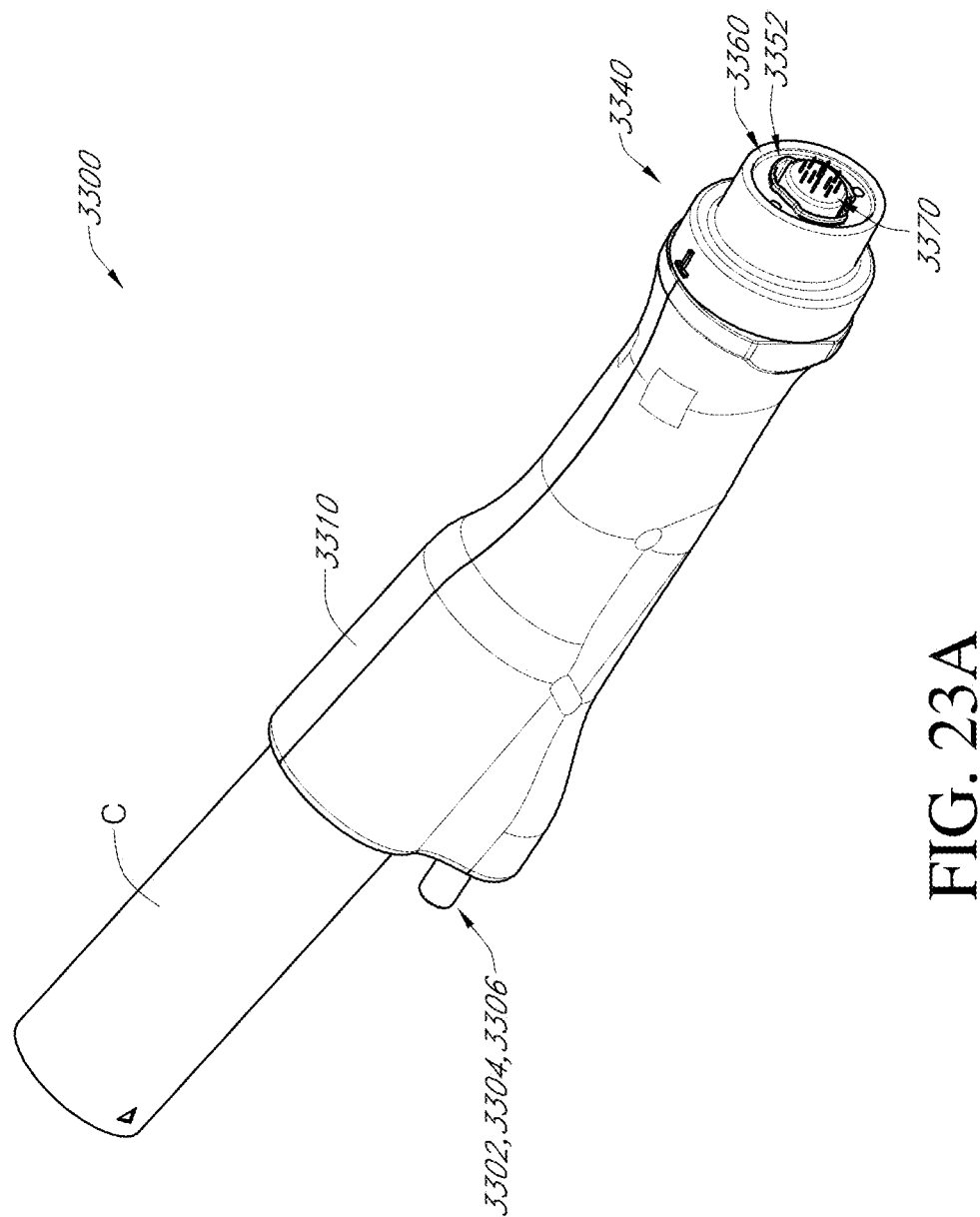
FIGS. 23A-23E illustrate various views of a skin treatment system comprising air pulsing and needle penetration, according to one embodiment.
Figure 23B:
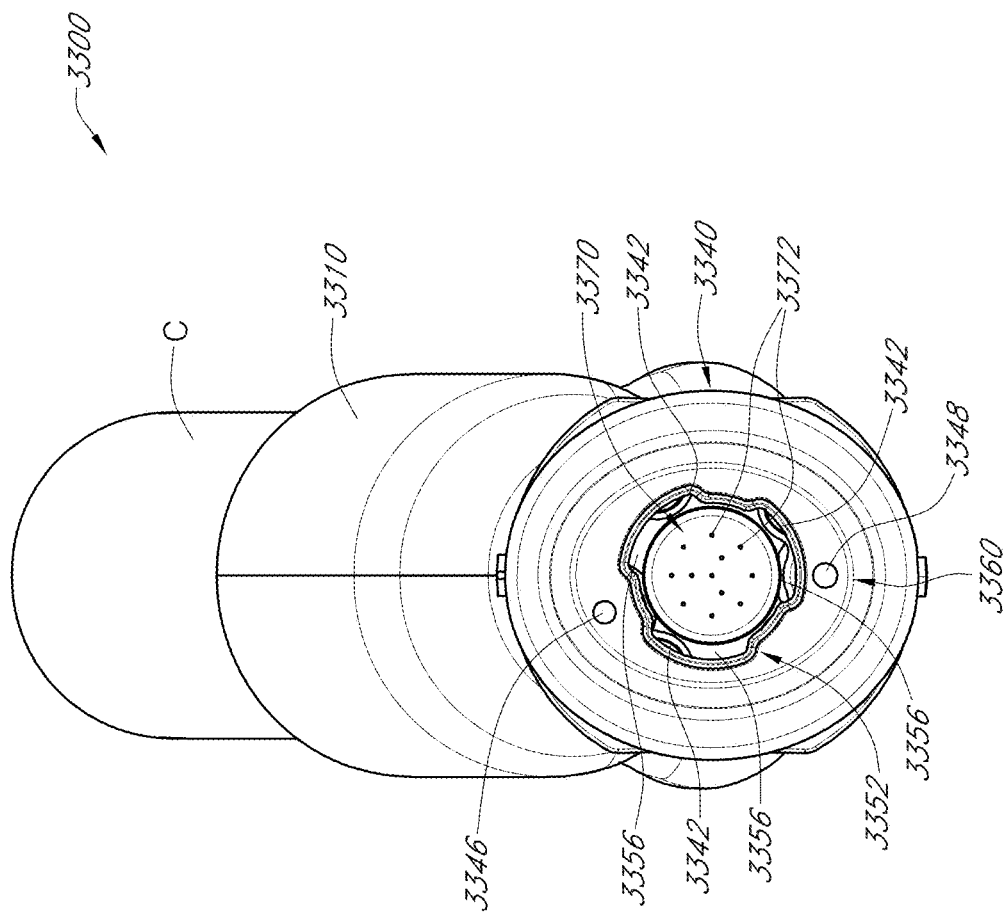

With reference to front view of the tip in FIG. 23B, as with other device embodiments disclosed herein, the area or space extending between the inner and outer lips or ridges 3352, 3360 can be configured to receive one or more treatment fluids when the device is in use. For example, when the lips or ridges 3352, 3360 contact a skin surface and a vacuum or suction source is activated, serum and/or other liquid from a fluid source (e.g., a cartridge C, as illustrated in FIGS. 23A-23E, a main fluid conduit that is coupled to a manifold system, etc.) can be delivered through one or more fluid delivery ports 3346 located between the ridges 3352, 3360. Spent fluid and/or other debris can be removed from the tip and the skin/device interface through a vacuum opening 3348, which, in the illustrated arrangement, is also located between the ridges 3352, 3360. As discussed above with reference to the device of FIGS. 22A-22E, the fluid delivery port 3346 and the suction or vacuum port 3348 can be spaced apart from each other by a desired separation distance, which can help ensure that the serums and/or other fluids that are delivered to the skin pass along at least a portion of the tip before being removed. In some embodiments, this can provide for longer contact time between the serums and/or other liquids and the skin, which can result in a better treatment outcome.

With continued reference to FIG. 23B, the inner ridge or lip 3352 can include one or more openings or passages 3356 that are adapted to provide pulsed air to the region defined by the ridge 3352. In the depicted embodiment, there are three separate openings or opening sections 3356 contained within an interior of the inner ridge or lip 3352. However, in other embodiments, the inner ridge can include more or fewer openings or opening sections, as desired or required. Pulsed air or other gas can be selectively provided through such openings 3356 to create a desired puffing or air-driven effect on the skin, as discussed in greater detail herein with reference to other air pulsing arrangements. In some embodiments, in order to maintain proper contact between the inner and outer ridges 3352, 3360 and the skin surface of the subject during use, one or more vacuum or suction ports 3342 can be strategically positioned along or near the inner ridge. Thus, the use of such suction can help prevent or reduce the likelihood of disengagement between the inner ridge 3352 and the skin surface being treated during use.

As shown in FIGS. 23A-23E, the device can additionally include a movable needle assembly 3370 within an interior portion of the tip 3340. In the illustrated embodiment, a single movable needle assembly is positioned along a central portion of the tip (e.g., within an interior of the inner ridge or lip 3352. However, in other embodiments, the size, shape, location, quantity and/or the details regarding the movable needle assembly 3370 can vary, as desired or required. The needle assembly can include a plurality of needles 3372 that extent outwardly (e.g., in a distal direction).

According to some embodiments, the needle assembly 3370 can be configured to reciprocate between proximal and distal positions during use. In some embodiments, the reciprocation or other movement of the needle assembly 3370 is accomplished pneumatically or mechanically. For example, in one embodiment, an air or other fluid line is coupled, at least partially, with a receptacle or housing in which the needle assembly 3370 is positioned. The delivery of positive and/or negative fluid pressure relative to the movable needle assembly 3370 (e.g., and/or a related receptacle or housing) can be used to move the needle assembly 3370 in a desired manner. In some embodiments, the movable needle assembly 3370 can be spring loaded (e.g., using a spring or other resilient member or assembly S located within the handpiece. Thus, in such configurations, the needle assembly 3370 can be resiliently biased in a retracted (or proximal) orientation by the spring or other resilient force. The exertion of a pressure or force on the needle assembly 3370 (e.g., using the selective delivery of air relative to the assembly 3370) can help displace the needle assembly 3370 away from its resiliently retracted position to a more distal orientation against the spring or biasing force. Once the force on the movable needle assembly is terminated, the needle can assume its retracted, proximal position.

According to some embodiments, the extent to which the needle assembly is moved distally can be precisely controlled. For example, the degree to which the needle assembly is advanced can depend on the spring force of the spring or other resilient member, the amount of force that is applied to the assembly 3370 and/or the like. Accordingly, such parameters can help control the depth of needle penetration into the skin caused by the needle assembly 3370. Depth of needle penetration and the resulting effect on the subject's skin tissue can also be altered using other methods. For example, the device 3300 can be provided to a user with a variety of tip options, each of which has a different maximum penetration distance (e.g., by varying the length, diameter, sharpness and/or other characteristics of the needles 3372 included in the assembly 3370). In some embodiments, the user is permitted to alter the maximum needle penetration distance by manipulation the tip and/or needle assembly. For example, in some embodiments, the height of the lips or ridges can be adjusted. In other arrangements, the user can change the orientation (e.g., depth) of the needle assembly within the handpiece to effectively modify the penetration depth.

In some embodiments, a user presses a button or manipulates one or more other controllers or features (e.g., switch, foot pedal, etc.) to selectively deploy the needle assembly 3370 distally (e.g., toward the skin surface). For example, in a pneumatically-controlled needle assembly configuration, the user can press a button to permit pressurized air to enter into the corresponding conduit of the handpiece so as to exert a force on the needle assembly. As a result, the needle assembly can be moved toward the skin. If sufficient force is applied to the needle assembly, the needle assembly may move sufficiently far (e.g., in the distal direction) to engage and at least penetrate an adjacent skin surface of the subject.

In other embodiments, the manipulation of a button or other controller can actuate a mechanically-generated force on the needle assembly 3370 to move the assembly distally against a spring or other resilient force. In yet other arrangements, the needle assembly is not resiliently biased (e.g., does not include a spring or other resilient member). For example, the movable assembly can moved between a proximal and a distal position using a motor, gear and/or the like. Regardless of the manner in which the needle assembly is moved toward and away from the skin surface of the subject, in some arrangements, the assembly can be moved along several different proximal/distal positions. In some embodiments, available positions can be distinct (e.g., only at certain distances) or continuous (e.g., along any position between fully retracted and fully extended), as desired or required.

In some embodiments, during use, the movable needle assembly 3370 can be actuated (e.g., to move distally to and through a skin surface) only when the treatment device 3300 is not being translated or moved relative to the subject's skin. Such a method of using these devices can help avoid undesirable harm to the subject. The use of needles to create passages within the one or more layers of skin being treated can provide additional benefits to the subject. For example, serums and/or other fluids delivered and/or otherwise located along the tip of the device can penetrate the subject's skin to a deeper extent. Such advantages and benefits can be further enhanced by the simultaneous air pulsing on the skin tissue.

Figure 23C:
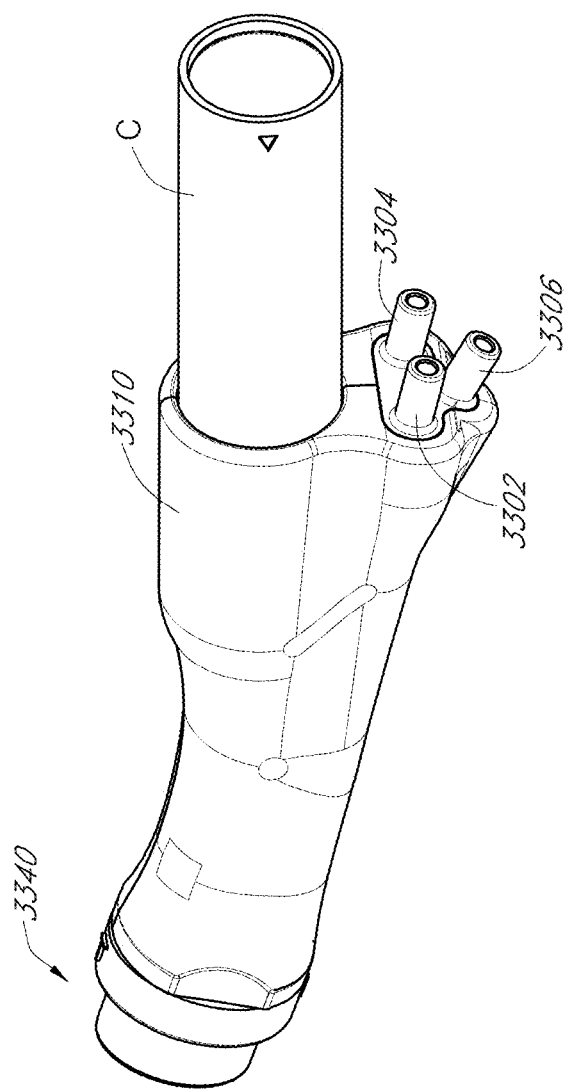
Figure 23D:
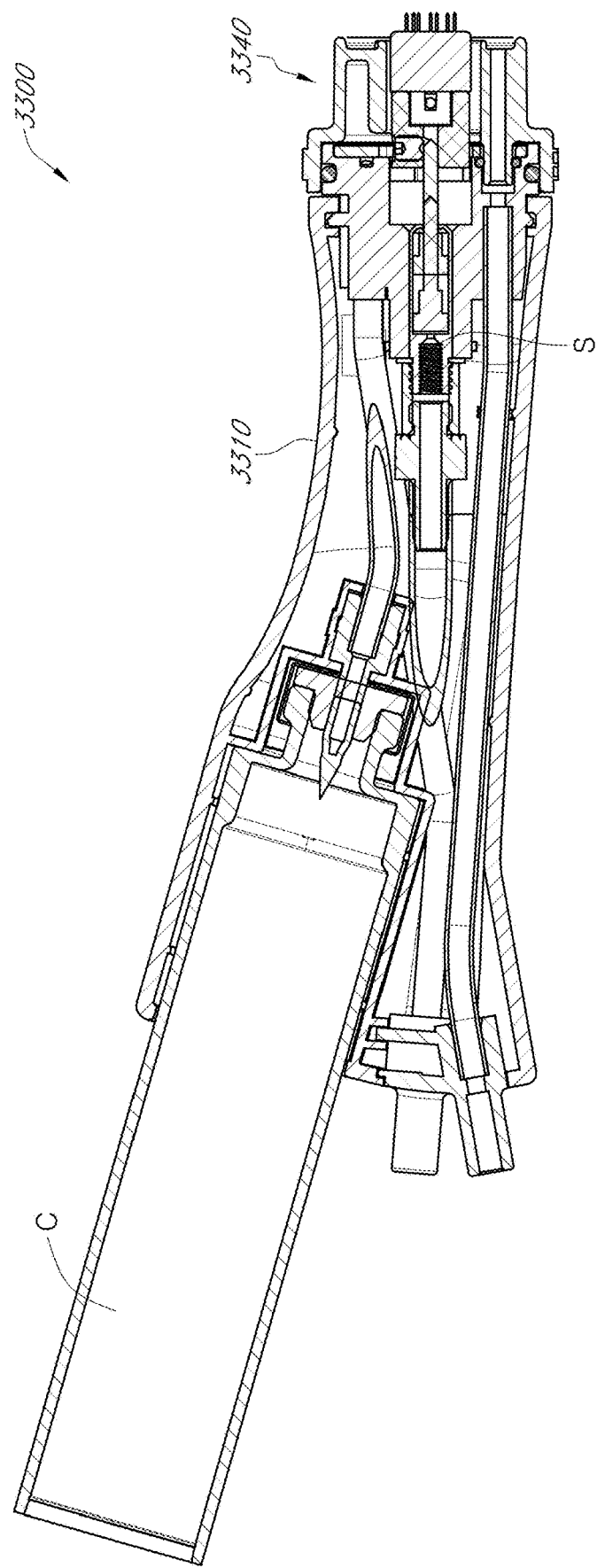
Figure 23E:
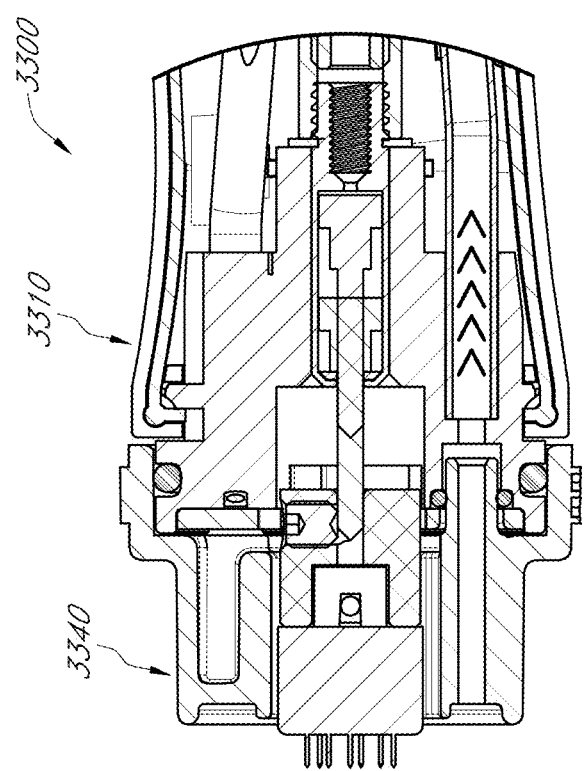

As shown in FIG. 23C, the device 3300 can include additional ports 3302, 3304, 3306 for connecting to a vacuum source (e.g., to the suction port), an air supply line (e.g., to the movable needle assembly; for selectively pneumatically actuating the assembly) and/or a pulsed air source (e.g., for providing pulsed air to the tip of the device). Such fluid sources can be separate from the treatment system or may be at least partially incorporated into the system, as desired or required. In some embodiments, at a minimum, the vacuum, air supply and pulsed air sources are in data communication with a control module or other controller to permit a user of the device to advantageously regulate the level of suction, position of the needle assembly and/or the level of pulsing during use. In some embodiments, the button or other controller associate with movement of the movable needle assembly can be coupled or incorporated into a valve structure in order to regulate the delivery of air or another gas to the assembly.

According to some embodiments, the needles 3372 of the needle assembly 3370 can be solid or hollow. In some embodiments, the needle diameter is 0.001-0.050 inches (e.g., 0.010 inches, 0.001-0.005, 0.005-0.010, 0.010-0.020, 0.020-0.030, 0.030-0.040, 0.040-0.050 inches, diameters between the foregoing ranges, etc.). In other embodiments, the needle diameter is less than 0.001 inches or greater than 0.050 inches (e.g., 0.050-0.060, 0.060-0.070, 0.070-0.080, 0.080-0.090, 0.090-0.100 inches, diameters between the foregoing ranges, greater than 0.100 inches, etc.). In some embodiments, the needle length is 0.05-5 mm (e.g., 0.5-2.5, 0.05-0.1, 0.1-0.2, 0.2-0.3, 0.3-0.4, 0.4-0.5, 0.5-0.6, 0.6-0.7, 0.7-0.8, 0.8-0.9, 0.9-1.0, 1-2, 2-3, 3-4, 4-5 mm, lengths between the foregoing ranges, greater than 5 mm, etc.).

In any of the embodiments disclosed herein that incorporate a needle assembly specially or any needle penetration technologies generally, the needles can be solid and/or hollow. In some embodiments, the needles can be configured to be selectively heated or cooled. For example, in one embodiment, the needles can be heated using resistive heating (e.g., via electrical energy, radiofrequency energy, etc.), using vapor (e.g., hot vapor) or similar techniques, thermoelectric devices and/or the like.

In any of the treatment embodiments disclosed herein, one or more pulsing parameters can be modified to create a desired effect on the subject's skin. For example, as noted above, the high and low pulse pressures can be adjusted. Further, in some embodiments, the duty cycle, frequency, air flowrate and/or other properties can be modified, as desired or required. For example, the duty cycle can be modified between 20 and 60% (e.g., 20-25, 25-30, 30-35, 35-40, 40-45, 45-50, 50-55, 55-60%, duty cycles between the foregoing ranges, etc.). In other embodiments, the duty cycle for the pulsed air system is greater than 60% (e.g., 60-70, 70-80, 80-90, 90-95%, duty cycles between the foregoing, greater than 95%, etc.) or less than 20% (e.g., 0-5, 5-10, 10-15, 15-20%, duty cycles between the foregoing ranges, etc.).

According to some embodiments, for any of the arrangements disclosed herein, the frequency of the pulsed air can vary between 2 and 15 Hz (e.g., 2-3, 3-4, 4-5, 5-6, 6-7, 7-8, 8-9, 9-10, 10-11, 11-12, 12-13, 13-14, 14-15 Hz, frequencies between the foregoing ranges, etc.). In other embodiments, however, the frequency of pulsed air can be less than 2 Hz (e.g., 0-0.5, 0.5-1, 1-1.5, 1.5-2 Hz, frequencies between the foregoing ranges, etc.) or greater than 15 Hz (e.g., 15-20, 20-25, 25-30, 30-40, 40-50 Hz, frequencies between the foregoing ranges, greater than 50 Hz, etc.).

To assist in the description of the disclosed embodiments, words such as upward, upper, bottom, downward, lower, rear, front, vertical, horizontal, upstream, downstream have been used above to describe different embodiments and/or the accompanying figures. It will be appreciated, however, that the different embodiments, whether illustrated or not, can be located and oriented in a variety of desired positions.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the inventions are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods summarized above and set forth in further detail below describe certain actions taken by a practitioner; however, it should be understood that they can also include the instruction of those actions by another party. The methods summarized above and set forth in further detail below describe certain actions taken by a user (e.g., a professional in some instances); however, it should be understood that they can also include the instruction of those actions by another party. Thus, actions such as "moving a handpiece" or "delivering a fluid" include "instructing moving a handpiece" and "instructing delivering a fluid." The ranges disclosed herein also encompass any and all overlap, sub-ranges, and combinations thereof. Language such as "up to," "at least," "greater than," "less than," "between," and the like includes the number recited. Numbers proceeded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A method of performing a skin treatment procedure, comprising:
    receiving a first container in a first station of a manifold assembly of a skin treatment system;
    receiving a second container in a second station of the manifold assembly;
    wherein fluid from the first container received in the first station and fluid from the second container received in the second station are configured to be placed in fluid communication with a handpiece assembly; and
    wherein each of the first and second containers comprises an identification tag;
    detecting the identification tag of the first container using a first reader positioned at or near the first station;
    detecting the identification tag of the second container using a second reader positioned at or near the second station; and
    processing data related to the detected identification tag of the first container and the second container using a control module of the skin treatment system;
    wherein, based on the data processed using the control module, the skin treatment system is configured to prevent fluid contained in at least one of the first and second containers from being delivered to the handpiece assembly.

2. The method of claim 1, comprising processing data related to the detected identification tags of the first container and the second container using a control module of the skin treatment system and, if the data related to the detected identification tag matches a predefined condition, preventing fluid contained in the respective first and/or second container from being delivered to the handpiece assembly.

3. The method of claim 1, wherein the manifold assembly is included in a tower system of the skin treatment system.

4. The method of claim 1, wherein each of the identification tags comprises an RFID tag and wherein each of the first and second readers comprises an RFID reader.

5. The method of claim 1, wherein the identification tags are configured to be detected by the first and second readers automatically once the first and second containers are positioned in the first and second stations.

6. The method of claim 1, wherein each of the first and second containers comprises a bottle.

7. The method of claim 6, wherein each bottle comprises the identification tag along an upper portion of the bottle.

8. The method of claim 1, wherein each of the identification tags includes information regarding contents of the container, an expiration date, a manufacturing date, and/or a lot number.

9. The method of claim 1, wherein the control module is configured to determine whether it is safe or appropriate to perform a skin treatment procedure based, at least in part, on the data related to the detected identification tags.

10. The method of claim 1, further comprising collecting the data obtained from the detected identification tags.

11. The method of claim 1, further comprising receiving information from a user of the skin treatment system related to fluid contained in at least one of the first and second containers.

12. A method of performing a skin treatment procedure, comprising:
    receiving a container in at least one station of a manifold assembly of a skin treatment system;
    wherein the manifold assembly is configured to place fluid from the container received in the at least one station in fluid communication with the manifold assembly; and
    wherein the container comprises an identification tag;
    detecting the identification tag of the container using a reader positioned at or near the at least one station; and
    processing data related to the detected identification tag using a control module of the skin treatment system;
    wherein, based on the data processed using the control module, the skin treatment system is configured to prevent fluid contained in the container from being delivered to the handpiece assembly.

13. The method of claim 12, wherein the manifold assembly is included in a tower system of the skin treatment system.

14. The method of claim 12, wherein the identification tag comprises an RFID tag, and wherein the reader comprises an RFID reader.

15. The method of claim 12, wherein the identification tag is configured to be detected by the reader automatically once the container is positioned in the at least one station.

16. The method of claim 12, wherein the container comprises a bottle.

17. The method of claim 16, wherein the bottle comprises the identification tag along an upper portion of the bottle.

18. The method of claim 12, wherein the identification tag includes data regarding contents of the container, an expiration date, a manufacturing date, and/or a lot number.

19. The method of claim 12, wherein the control module is configured to determine whether it is safe or appropriate to perform a skin treatment procedure based, at least in part, on the data related to the detected identification tag.

20. The method of claim 12, further comprising collecting the data obtained from the detected identification tag.

21. The method of claim 12, wherein the at least one station comprises at least two stations, wherein each of the at least two stations comprises a reader.

* * * * *